US006436642B1

(12) United States Patent
Gould-Rothberg et al.

(10) Patent No.: US 6,436,642 B1
(45) Date of Patent: Aug. 20, 2002

(54) METHOD OF CLASSIFYING A THYROID CARCINOMA USING DIFFERENTIAL GENE EXPRESSION

(75) Inventors: Bonnie E. Gould-Rothberg; Luca Rastelli, both of Guilford, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/552,322

(22) Filed: Apr. 19, 2000

Related U.S. Application Data

(60) Provisional application No. 60/130,123, filed on Apr. 20, 1999, and provisional application No. 60/193,203, filed on Mar. 30, 2000.

(51) Int. Cl.$^7$ .......................... C12Q 1/68; C12P 21/06; C12N 15/00
(52) U.S. Cl. ...................... 435/6; 435/69.1; 435/320.1
(58) Field of Search ........................ 435/6, 69.1, 320.1

(56) References Cited

U.S. PATENT DOCUMENTS 5,871,697 A   2/1999   Rothberg et al.

FOREIGN PATENT DOCUMENTS

| WO | WO 94/2118  | 9/1994 |
| WO | WO 99/14328 | 3/1999 |

OTHER PUBLICATIONS

Scheumman et al. Clinical significance of E–cadherin as a prognostic marker in thyroid carcinomas. J Clin Endocrinol Metab., 80(7): 2168–2172, 1995.

Alhonen, L., et al. (1999). "Transgenic Mice with Activated Polyamine Catabolism due to Overexpression of Spermidine/Spermine N$^1$–Acetyltransferase Show Enhanced Sensitivity to the Polyamine Analog, N$^1$, N$^{11}$–Diethylnorspermine." *Mol Pharmacol* 55(4): 693–98.

Banerjee, S. K, et al. (2000). "Overexpression of vascular endothelial growth factor164 and its co–receptor neuropilin–1 in estrogen–induced rat pituitary tumors and GH3 rat pituitary tumor cells." *Int J Oncol* 16(2): 253–60.

Banfi, P., et al. (1994). "The Daunorubicin–Binding Protein of M$_r$ 54,000 Is an Aldehyde Dehydrogenase and Is Down–Regulated in Mouse Liver Tumors and in Tumor Cell Lines." *Mol Pharmacol* 46(5): 896–900.

Saverio, B., et al. (2000). "Tumor Progression is Accompanied by Significant Changes in the Levels of Expression of Polyamine Metabolism Regulatory Genes and Clusterin (Sulfated Glycoprotein 2) in Human Prostate Cancer Specimens [published erratum appears in Cancer Res (2000 Mar. 1);60(5):1472]." *Cancer Res* 60(1): 28–34.

Braun, C., et al. (1999). "Expression of calpain I messenger RNA in human renal cell carcinoma: correlation with lymph node metastasis and histological type." *Int J Cancer* 84 (Pred. Oncol.) (1): 6–9.

Chung, C. Y., et al. (1996) "Mitogenesis, Cell Migration, and Loss of Focal Adhesions Induced by Tenascin–C Interacting with Its Cell Surface Receptor, Annexin II." *Mol Biol Cell* 7(6): 883–92.

Cui, X., et al. (1998). "Association of SET domain and myotubularin–related proteins modulates growth control." *Nat Genet* 18(4): 331–37.

Frolova, E., et al. (2000). "The expression pattern of a novel Deltex homologue during chicken embryogenesis." *Mech Dev* 92(2): 285–89.

Furukawa, T., et al. (1998). "Genomic analysis of DUSP6, a dual specificity MAP kinase phosphatase, in pancreatic cancer." *Cytogenet Cell Genet* 82(3–4): 156–59.

Garver, R. I., et al. (1994). "Strategy for achieving selective killing of carcinomas." *Gene Ther* 1(1): 46–50.

Iwase, K., et al. (1993). "Localization of Cu/Zn and Mn superoxide dismutase in various thyroid disorders." *Acta Endocrinol (Copenh)* 129(6): 573–78.

Kiljanski, J., et al. (1996). "Significance of tissue specific and tissue non specific autoimmune reactions of Graves' disease." *Clin Exp Rheumatol* 14 Suppl 15: S69–76.

Kitaura, Y., et al. (1999). "Peflin, a Novel Member of the Five–EF–Hand–Protein Family, is Similar to the Apoptosis–Linked Gene 2 (ALG–2) Protein But Possesses Nonapeptide Repeats in the N–Terminal Hydrophobic Region." *Biochem Biophys Res Commun* 263(1): 68–75.

Koivunen, E., et al. (1999). "Tumor targeting with a selective gelatinase inhibitor." *Nat Biotechnol* 17(8): 768–74.

Kos, J., et al. (2000). "Cysteine Proteinase Inhibitors Stefin A, Stefin B, and Cystatin C in Sera from Patients with Colorectal Cancer: Relation to Prognosis." *Clin Cancer Res* 6(2):505–11.

Lacana, E., et al. (1997). "Dissociation of Apoptosis and Activation of IL–1beta–Converting Enzyme/Ced–3 Proteases by ALG–2 and the Truncated Alzheimer's Gene ALG–3." *J Immunol* 158(11): 5129–35.

Mao, M., et al. (1998). "Identification of genes expressed in human CD34(+) hematopoietic stem/progenitor cells by expressed sequence tags and efficient full– length cDNA cloning." *Proc Natl Acad Sci USA* 95(14): 8175–80.

Masaki, T., et al. (1996). "Enhanced Expression of the Protein Kinase Substrate Annexin in Human Hepatocellular Carcinoma." *Hepatology* 24(1): 72–81.

Matsuo, K., et al. (1996). "Immunohistochemical Localization of Cathepsins D and E in Human Gastric Cancer: a Possible Correlation with Local Invasive and Metastatic Activities of Carcinoma Cells." *Hum Pathol* 27(2): 184–90.

(List continued on next page.)

*Primary Examiner*—Jeffrey Fredman
*Assistant Examiner*—Suryaprabha Chunduru
(74) *Attorney, Agent, or Firm*—Mintz, Levin, Cohn, Ferris, Glovsky and Popeo, P.C.; Ivor R. Elrifi, Esq.; Christina V. Karnakis, Esq.

(57) ABSTRACT

Disclosed are methods of diagnosing and treating carcinomas, including metastatic thyroid carcinomas using differential gene expression. Also disclosed are novel nucleic acid sequences whose expression is differentially regulated in metastatic and non-metastatic thyroid carcinomas.

7 Claims, 5 Drawing Sheets

OTHER PUBLICATIONS

Onda, H., et al. (1999). "Tsc2(+/−) mice develop tumors in multiple sites that express gelsolin and are influenced by genetic background." *J Clin Invest* 104(6): 687–95.

Poblete, M. T., et al. (1996). "Alpha $_2$ 2–Antitrypsin Expression in Human Thyroid Papillary Carcinoma." *Am J Surg Pathol* 20(8): 956–63.

Ree, A. H., et al. (1999). "Expression of a Novel Factor in Human Breast Cancer Cells with Metastatic Potential." *Cancer Res* 59(18): 4675–80.

Scheumman, G. F., et al. (1995). "Clinical Significance of E–Cadherin as a Prognostic Marker in Thyroid Carcinomas." *J Clin Endocrinol Metab* 80(7): 2168–72.

Serru, V., et al. (2000). "Sequence and expression of seven new tetraspans." *Biochim Biophys Acta* 1478(1): 159–63.

Shimkets, R. A., et al. (1999). "Gene expression analysis by transcript profiling coupled to a gene database query." *Nat Biotechnol* 17(8): 798–803.

Sogawa, K., et al. (1996). "Role of protein phosphatase in malignant osteogenic and soft tissue tumors." *Res Commun Mol Pathol Pharmacol* 93(1):33–42.

Srikanth, S., et al. (1999). "Human DU145 prostate cancer cells overexpressing mitogen–activated protein kinase phosphatase–1 are resistant to Fas ligand–induced mitochondrial perturbations and cellular apoptosis." *Mol Cell Biochem* 199(1–2): 169–78.

Takano, T., et al. (2000). "Expression of Oncofetal Fibronectin Messenger Ribonucleic Acid in Fibroblasts in the Thyroid: A Possible Cause of False Positive Results in Molecular–Based Diagnosis of Thyroid Carcinomas." *J Clin Endocrinol Metab* 85(2): 765–68.

Tanaka, M., et al., (1995). "Human calgizzarin; one colorectal cancer–related gene selected by a large scale random cDNA sequencing and northern blot analysis." *Cancer Lett* 89(2): 195–200.

Tissot, C., et al. (1995). "Molecular Cloning of a New Interferon–Induced Factor That Represses Human Immunodeficiency Virus Type 1 Long Terminal Repeat Expression." *J Biol Chem* 270(25): 14891–98.

Vasseur, S., et al. (1999). "Cloning and expression of the human p8, a nuclear protein with mitogenic activity." *Eur J Biochem* 259(3): 670–75.

Wegrowski, Y., et al. (1999). "Transforming Growth Factor beta–1 Up–Regulates Clusterin Synthesis in Thyroid Epithelial Cells." *Exp Cell Res* 247(2): 475–83.

Williams, A., et al. (1999). "The expression of genes in the ubiquitin–proteasome proteolytic pathway is increased in skeletal muscle from patients with cancer." *Surgery* 126(4): 744–49; discussion 749–50.

Zhou, T. H., et al. (2000). "Identification of a Human Brain–specific Isoform of Mammalian STE20–like Kinase 3 That is Regulated by cAMP–dependent Protein Kinase." *J Biol Chem* 275(4):2513–19.

Zimmermann, A. G., et al. (1997). "Regulation of Inosine–5'–monophosphate Dehydrogenase Type II Gene Expression in Human T Cells. Role for a novel 5' palindromic octamer sequence." *J Biol Chem* 272(36): 22913–23.

METHOD OF CLASSIFYING A THYROID CARCINOMA USING DIFFERENTIAL GENE EXPRESSION

RELATED APPLICATIONS

This application claims priority to U.S. Ser. No. 60/130,123, filed Apr. 20, 1999, and U.S. Ser. No. 60/193,203, filed Mar. 30, 2000.

FIELD OF THE INVENTION

The invention relates in general to nucleic acids and more particularly to the use of genes differentially expressed in metastatic thyroid carcinomas and non-metastatic thyroid carcinomas.

BACKGROUND OF THE INVENTION

The thyroid is an endocrine gland involved in the homeostatic regulation of bodily functions. Its basic morphologic unit is the follicle, which contains two major parenchymal cell types: the follicular cells and the parafollicular cells.

The diseases affecting the thyroid gland can be classified as benign and malignant. Benign diseases can include diffuse goiter, such as Graves' disease, and nodular goiter, such as nodular hyperplastic goiter. Other benign thyroid disorders include thyroiditis and benign neoplasms, such as adenomas.

Thyroid cancer is a common endocrine tumor. The reported incidence of thyroid cancer is about 4 per 100,000, with the number of afflicted males and females occurring at a relative ratio of 2:1. It is possible that the actual incidence of thyroid cancer is higher, as thyroid cancers, like prostate malignancies, are most typically found as occult tumors during autopsy.

Thyroid cancers are typically classified according to their cellular origin and level of differentiation. For example, follicular cells produce well-differentiated carcinomas and anaplastic carcinomas, while parafollicular cells produce medullary thyroid carcinomas. Other cancers associated with the thyroid gland include sarcomas, originating from stromal cells of the thyroid, and lymphomas, which originate from immune cells associated with the thyroid A majority of thyroid malignancies are well-differentiated, slow-growing, and remain local to the thyroid gland. Removal of the thyroid, followed by $^{125}$I gamma irradiation of any remaining thyroid tissue, typically elicits a good response and prognosis for patients whose cancer has not spread beyond the thyroid gland. Extension of tumors into adjacent neck structures or more distant sites from the thyroid is associated with a significantly worse prognosis. The prognostic significance of local metastases to lymph nodes in the region of the lymph node is less clear.

The mechanisms by which thyroid cancers metastasize to distant sites in the body are not completely understood. For example, not all the genes whose expression levels change in response to a thyroid metastasis have been identified. In addition to providing potential targets in metastatic tissue that could be used for treat metastasized genes, such genes could also be used to diagnose metastatic tissues.

SUMMARY OF THE INVENTION

The invention is based in part on the discovery of genes whose expression levels can be correlated to one or more metastatic cancerous states in a thyroid cell. Measuring expression levels of these genes in a sample cell population allows for the type and tumor stage of the cells in the sample to be determined.

Accordingly, in one aspect the invention relates to genes that are differentially expressed in metastatic versus non-metastatic thyroid cancer. These differentially expressed genes are collectively referred to herein as "Metastatic Thyroid Cancer" genes ("MTC genes"). The corresponding gene products are referred to as "MTC products" and/or "MTC proteins". The MTC genes include E-cadherin, alpha-1-antitrypsin, manganese superoxide dismutase, thyroglobulin, fibronectin, CD18, calpain, clusterin, cathepsin E, cystatin B, RIG-E, p8=candidate of metastasis 1, periplakin, neuropilin, proteasome subunit HC5, NET-1, ras GTPase-activating-like protein (IQGAP1), DUSP6 dual specificity MAP kinase phosphatase, SET binding factor (SBF), 5-lipoxygenase, lipocortin I, lipocortin II, annexin II, calgizzarin, spernmidine/spermine N1-acetyltransferase (SSAT), daunorubicin-binding protein=aldehyde dehydrogenase 2, gelsolin, integrin alpha-3, Type IV collagenase, antileukoprotease, STE20-like protein kinase 3 (STK3), peflin, and kinectin.

In various aspects, the invention includes methods of categorizing thyroid neoplasms, diagnosing thyroid carcinomas, assessing the efficacy of a treatment of a thyroid carcinoma in a subject, and assessing the prognosis of a subject with a thyroid carcinoma. Each of these methods involves providing a test cell population from a subject capable of expressing one or more metastatic thyroid carcinoma nucleic acid sequences, termed MTC sequences, measuring the expression of these MTC sequences in the test cell population, and comparing the levels of expression in the test cell population with the expression levels in a reference cell population whose thyroid carcinoma stage is known.

In a further aspect, the invention includes a method of selecting an individualized therapeutic agent appropriate for a particular subject. This method includes providing from the subject, a test cell population comprising a cell capable of expressing one or more MTC sequences, contacting the test cell population with the therapeutic agent, and comparing the expression of the MTC sequences in the test cell population to the expression levels in a reference cell population whose thyroid carcinoma stage is known.

In another aspect, the invention provides a method of identifying a candidate therapeutic agent for treating thyroid carcinomas. This method includes providing a test cell population capable of expressing one or more MTC sequences, contacting the test cell population with a candidate therapeutic agent, and comparing the expression of the MTC sequences to the expression in a reference cell population whose thyroid carcinoma stage is known.

The invention further provides a method of treating metastatic cancer. In one embodiment, this method includes administering to a patient suffering from or at risk for developing metastatic cancer, an agent that increases the expression of one or more MTC sequences that are down-regulated in metastatic versus non-metastatic cancer. In another embodiment, this method involves administering an agent that decreases the expression of one or more MTC sequences that are up-regulated in metastatic versus non-metastatic cancer.

Further provided is a kit comprising one or more reagents for detecting the presence of two or more MTC nucleic acid sequences and an array of probe nucleic acids capable of detecting two or more MTC nucleic acid sequences. Also provided are isolated nucleic acid molecules that are differentially expressed in metastatic vs. non-metastatic thyroid cancer, as well as single nucleotide polymorphisms in MTC sequences, and methods of using the MTC single nucleotide polymorphisms.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

Other features and advantages of the invention will be apparent from the following detailed description and from the claims.

BRIEF DESCRIPTION OF THE DRAWINGS

FIG. 1 is a representation of the sequence homology between a mouse MTC48 amino acid sequence according to the invention and a human MTC48 amino acid sequence according to the invention.

Figure 3:
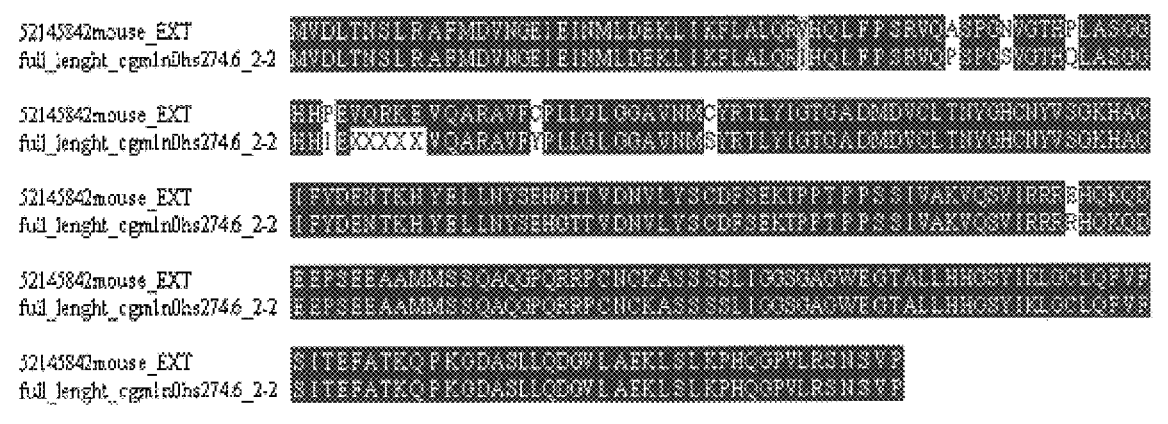

FIG. 3 is a representation of the sequence homology between mouse MTC49 amino acid sequence according to the invention and a human MTC49 amino acid sequence according to the invention.

FIG. 4 is an illustration of the sequence homology between a nucleic acid encoding protein Q9Y3Z0 and a MTC50 nucleic acid according to the invention.

FIG. 5 is an illustration of the sequence homology between the rat gene E3-3 (AAB54063) and a MTC50 nucleic acid according to the invention.

DETAILED DESCRIPTION OF THE INVENTION

Figure 2:
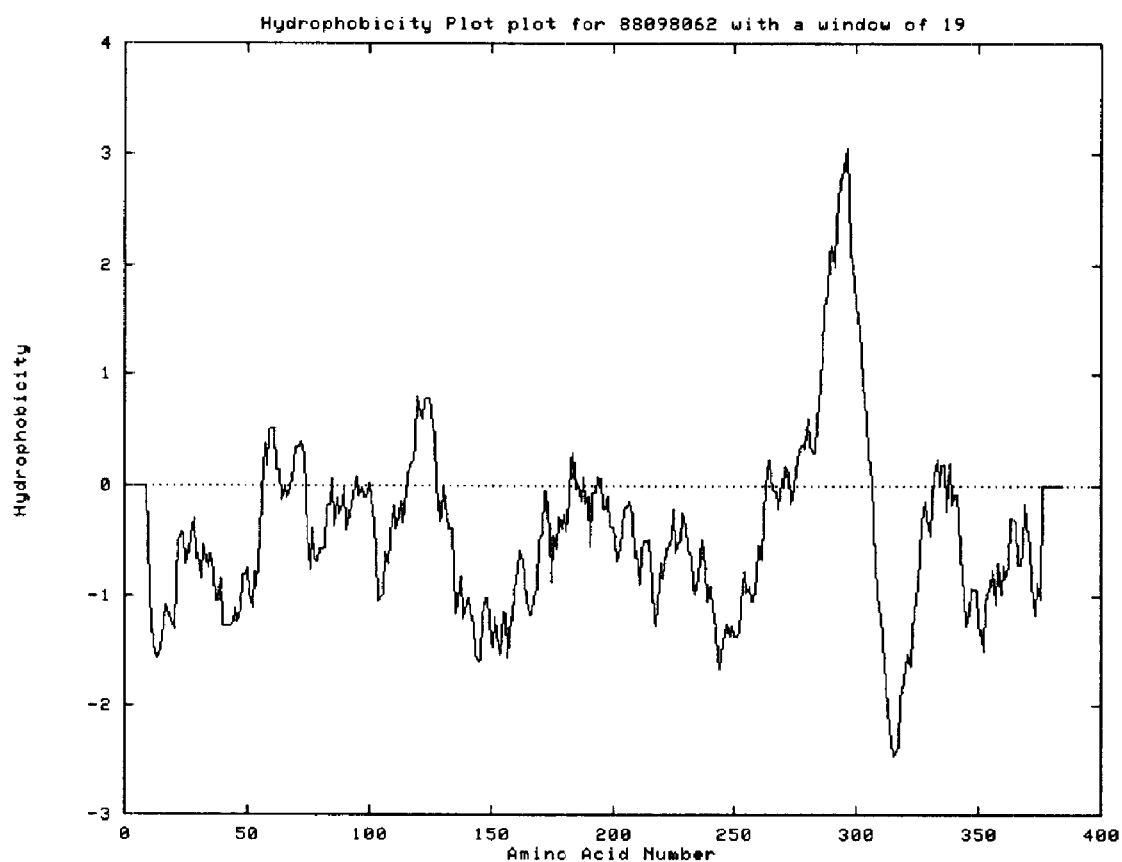
FIG. 2 is a representation of a hydrophobicity plot for a MTC48 nucleic acid according to the invention.

The present invention is based in part on the discovery of changes in expression patterns of multiple nucleic acid sequences in metastatic papillary thyroid carcinomas versus in non-metastatic thyroid follicular adenomas. Changes in expression have been observed in both heretofore undescribed nucleic acid sequences as well as in previously identified nucleic acid sequences. By measuring the expression of one or more of these nucleic acid sequences in response to various agents, agents for treating cancer can be identified. In addition, the measurement of the expression profiles of one or more of these sequences can be used, for example, to diagnose a neoplasm, to categorize a neoplasm, to assess prognosis, and to monitor the efficacy of neoplasm treatment.

To identify differentially expressed genes according to the invention, fresh frozen surgical specimens were obtained from three thyroid follicular adenomas and three metastatic papillary thyroid carcinomas. These samples were processed through GENECALLING™ differential expression analysis, as described in U.S. Pat. No. 5,871,697 and in Shimkets et al., Nature Biotechnology 17:798–803 (1999). GENECALLING™ technology relies on Quantitative Expression Analysis to generate a gene expression profile of a given sample and then generates differential expression analysis of pairwise comparison of these profiles to controls containing no additions. Polynucleotides exhibiting differential expression are confirmed by conducting a PCR reaction according to the GENECALLING™ protocol with the addition of a competing unlabeled primer that prevents the amplification from being detected.

Comparing any two samples with each other (either between or across treatment groups) revealed a 10% difference rate between samples. This difference highlights both the highly variable nature of neoplastic growths and the high level of individual variation. To identify those genes that are differentially expressed between the hyperplastic adenamatous state and the metastatic carcinomous state, all three follicular adenomas were compared as a group to all three papillary carcinomas as a group. Differences were confirmed if they exhibited consistent behavior across all adenomas and were significantly different from all carcinomas. This strategy reduced the number to significant difference to 80 (0.5%). Fifty-one genes were confirmed as being differentially expressed. For convenience and ease of reference, these genes have been designated as MTC:1-51.

A summary of the differentially expressed sequences is presented in Table 1. The first three columns of this Table provide descriptive information for these sequences. Specifically, Column 1 provides the common names of each of the genes, Column 2 lists the sequence database reference number for previously known sequences, and Column 3 provides the SEQ ID NOs for the newly discovered nucleic acid sequences. Column 4 displays the change in expression level of each sequence that was observed in metastatic thyroid carcinomas as compared to nonmetastatic thyroid carcinomas. Column 5 provides the MTCX number assigned to each of the differentially expressed genes for ease of reference.

The differentially expressed genes are subdivided into groups in Table 1 as follows: genes whose expression is previously correlated with metastatic thyroid cancer; genes whose expression is newly correlated with metastatic thyroid cancer; and nucleic acid sequences newly described herein.

One of ordinary skill in this art will recognize that the information in Table 1 can be used to identify a particular MTC sequence. For example, where the sequence database reference number of a particular nucleic acid sequence is known, this reference number can be used to identify a particular MTC sequence. For a given MTC sequence, its expression can be measured by using any methods commonly known in the art. Based on all of this, one of ordinary skill in the art will be able to deduce the information necessary for detecting and measuring the expression of each MTC nucleic acid sequence, as required by each of the methods described herein.

TABLE 1

| Description of Sequence | Sequence Database Reference | SEQ ID NO: | Change in Expression Level in Metastatic vs. Non-Metastatic Cells | MTCX Assignment |
|---|---|---|---|---|
| Genes Whose Expression Is Previously Correlated with Metastatic Thyroid Cancer | | | | |
| Fibronectin | X02761 K00055 K00799 K02273 X00307 X00739 | | +19.8 | MTC1 |
| Thyroglobulin | X05615 | | −4.6 | MTC2 |
| Alpha-1-antitrypsin | M11465 | | +7.1 | MTC3 |
| E-cadherin | CAA79356, Z18923 | | −4.2 | MTC4 |
| Manganese superoxide dismutase (MnSOD) | X65965 | | +2.8 | MTC5 |
| Integrin beta-2, CD18 (ITGB2) (LFA-1/CR3/P150, 95) | M15395 | | +2.5 | MTC6 |
| Nebulin | X83957 | | +7.1 | MTC7 |
| Genes Whose Expression Is Newly Correlated with Metastatic Thyroid Cancer | | | | |
| Type IV collagenase | J03210 | | +3.7 | MTC8 |
| Neuropilin I | NM_003873 | | +11.8 | MTC9 |
| Ca2-activated neutral protease large subunit | M23254 | | +2.5 | MTC10 |
| Clusterin (apolipoprotein J) | NP_001822 | | +5.4 | MTC11 |
| Cathepsin E | J05036 | | +3.1 | MTC12 |
| Cystatin B | U46692 | | +1.6 | MTC13 |
| Lipocortin I | X05908 | | +3.1 | MTC14 |
| Lipocortin II | D00017 | | +4.5 | MTC15 |
| Retinoic acid induced RIG-E precursor (RIG-E) | U42376 | | +3.7 | MTC16 |
| p8 (candidate of metastasis 1) | AF069073 NM_012385 | | −2.3 | MTC17 |
| protein phosphatase-1 gamma 1 | L07395 | | +1.5 | MTC18 |
| Tetraspan NET-1 | AF065388 | | +7.3 | MTC19 |
| Periplakin | AF013717 | | +2.7 | MTC20 |
| Proteasome subunit HC5 | D00761 | | +2.1 | MTC21 |
| ras GTPase-activating-like protein (IQGAP1) | NP_003861 L33075 | | +2.7 | MTC22 |
| DUSP6 dual specificity MAP kinase phosphatase | AB013382 | | +3.2 | MTC23 |
| SET binding factor (SBF1) | U93181 | | −4.5 | MTC24 |
| 5-lipoxygenase | J03571 | | +3.7 | MTC25 |
| Calgizzarin | D38583 | | +2.2 | MTC26 |
| Spermidine/spermine N1-acetyltransferase (SSAT) | M77693 | | +2.1 | MTC27 |
| Aldehyde dehydrogenase 2 (ALDH-2) | K03001 | | −2.7 | MTC28 |
| Gelsolin | X04412 | | +2.7 | MTC29 |
| Integrin alpha-3 | AAA3612 | | +2.9 | MTC30 |
| KIAA0937 | AB023154 | | +3.5 | MTC31 |
| KIAA1131 | AB032957 | | −2 | MTC32 |
| Antileukoprotease | X04470 | | +11.1 | MTC33 |
| DAP12 | AF019562 | | +3.5 | MTC34 |
| brain-specific STE20-like protein kinase 3 (MST-3b) | AAD42039 | | +3.5 | MTC35 |
| Peflin | BAA85163 | | −1.8 | MTC36 |
| Kinectin | NM_004986 | | +3.5 | MTC37 |
| Prostaglandin transporter hPGT | U70867 | | −4.9 | MTC38 |
| Ribophorin II | Y00282 | | +2.5 | MTC39 |
| PRO302 | X25445 X52258 (Patent Database) | | −2 | MTC40 |
| Stimulated trans-acting factor (50 kDa) | X82200 | | +3.6 | MTC41 |
| Iduronate 2-sulfatase | M58342 | | +1.7 | MTC42 |
| Mitochondrial proteolipid 68 MP | AF054175 | | −1.7 | MTC43 |
| Growth arrest specific transcript 5 gene | AF141346 | | +2 | MTC44 |
| lactate dehydrogenase-A | X02152 | | +1.5 | MTC45 |
| 26-kDa surface protein TAPA-1 mRNA, complete cds; CD81 | M33680 | | −2.9 | MTC46 |
| Sodium dependent phosphate transporter isoform NaPi-3b | AF111856 | | +11.8 | MTC47 |

TABLE 1-continued

| Description of Sequence | Sequence Database Reference | SEQ ID NO: | Change in Expression Level in Metastatic vs. Non-Metastatic Cells | MTCX Assignment |
|---|---|---|---|---|
| Nucleic Acid Sequences Newly Described Herein | | | | |
| Novel human d010 – 145.3 = 88098062 | | SEQ ID NO: 1 | +6.6 | MTC48 |
| Cghs mln0274.6_2 | | SEQ ID NO: 5 | −2.1 | MTC49 |
| Human E3 – 3 = 95199195 | | SEQ ID NO: 10 | +2.7 | MTC50 |
| Cghs 10n0102.3_1 | | SEQ ID NO: 12 | −2 | MTC51 |

Below follows a brief description of some sequences whose expression level changes between metastatic and non-metastatic thyroid carcinomas. For some sequences, a summary of SAGE expression analysis is also presented below. Using this information, one of ordinary skill in the art will recognize that MTC sequences can be used to detect nucleic acid sequence expression in cells or tissues in which they are expressed.

Genes Whose Expression is Previously Correlated with Metastatic Thyroid Cancer

Genes identified as being differentially expressed in studies leading to the invention include fibronectin, E-cadherin, alpha-1-antitrypsin, manganese superoxide, thyroglobulin, and CD18. These genes have been previously described as being differentially expressed in metastatic and non-metastatic thyroid cancers. These genes are briefly discussed below.

Fibronectin (MTC1)

Fibronectin (genBank#X02761 K00055 K00799 K02273 X00307 X00739) is a 430,000 dalton dimeric glycoprotein that exists in two forms, which are named cellular and plasma fibronectin. Cellular fibronectin is the major cell surface glycoprotein of many cells. A major function of the fibronectins is to facilitate the adhesion of cells to extracellular materials, such as solid substrata and matrices. While there is agreement that fibronectin is up-regulated in metastatic thyroid cancer, it is not yet completely understood whether this is due to the tumor cells or to the infiltrating fibroblast (See Takano et al., J Clin Endocrinol Metab 85(2):765–8) (2000). GENECALLING™ analysis reveals that fibronectin is up-regulated in metastatic vs. non-metastatic thyroid cancer.

Thyroglobulin (MTC2)

Thyroglobulin (genBank#X05615) is the glycoprotein precursor of the thyroid hormones thyroxine (T4) and tri-iodothyronine (T3). Newly synthesized thyroglobulin is folded and homodimerized in the endoplasmic reticulum (ER) prior to its export to the site of iodination, where it serves as the precursor for thyroid hormone synthesis. Thyroglobulin is a reliable tumor marker in patients with well-differentiated thyroid cancer ("WDTC"). Low levels of thyroglobulin correlate with clinical stage and metastatic potential. GENECALLING™ analysis reveals that thyroglobulin is down-regulated in metastatic vs. non-metastatic thyroid cancer.

Alpha-1-antitrypsin (MTC3)

Alpha-1-antitrypsin (GenBank#M11465) is a major plasma serine protease inhibitor. Previous reports indicate that alpha-1-antitrypsin is present in 9 out of 10 thyroid papillary carcinomas while the normal thyroid tissue present in the vicinity of each tumor showed no staining (See Poblete et al., Am J Surg Pathol 20(8):956–63 (1996)). GENECALLING™ analysis reveals that alpha-1-antitrypsin is up-regulated in metastatic vs. non-metastatic thyroid cancer.

E-cadherin (MTC4)

Loss of E-cadherin (uvomorulin) (genBank#CAA79356, Z18923), a Ca(2+)-dependent cell adhesion molecule that is required for normal epithelial function has been attributed a pathogenetic role in tumor invasion. Previous reports indicate that steady-state E-cadherin mRNA levels and immunostaining were either reduced or lost in thyroid cancers. E-cadherin was greatly reduced upon progression to primary tumor stage 4 (pT4) tumors, and this reduction correlates with metastatic potential. (See Scheumman et al., J Clin Endocrinol Metab 80(7):2168–72 (1995)). GENECALLING™ analysis reveals that E-cadherin is down-regulated in metastatic vs. non-metastatic thyroid cancer.

Manganese Superoxide Dismutase (MnSOD) (MTC5)

Manganese superoxide dismutase (GenBank#X65965) is a member of a family of metalloenzymes that catalyze the dismutation of the superoxide anion to $H_2O_2$. MnSOD is encoded by nuclear chromatin, synthesized in the cytosol, and imported posttranslationally into the mitochondrial matrix. The MnSOD concentration is increased in papillary carcinoma or papillary-growing cells. (See Iwase et al., Acta Endocrinol (Copenh) 129(6):573–8 (1993)). GENECALLING™ analysis reveals that MnSOD is up-regulated in metastatic vs. non-metastatic thyroid cancer.

Integrin Beta-2, CD18 (ITGB2) (MTC6)

Integrin beta-2 is also known as human cell surface adhesion glycoprotein LFA-1 /CR3/P150,95 beta-subunit (genBank#M1 5395). This leukocyte cell adhesion molecule belongs to the class of cell membrane glycoproteins known as integrins, which are alpha-beta heterodimers. The alpha subunits vary in size from 120 to 180 kD, and each is noncovalently associated with a beta subunit (90 to 110 kD). Expression is increased in infiltrating lymphocytes and vascular endothelium in thyroid glands from patients with autoimmune thyroid disorders, Graves' disease (GD), and Hashimoto's thyroiditis (HT). GENECALLING™ analysis reveals that ITGB2 is up-regulated in metastatic vs. non-metastatic thyroid cancer. These cancers have high levels of infiltrating lymphocytes.

Nebulin (MTC7)

Nebulin (genBank#X83957) is a giant protein component of the cytoskeletal matrix that coexists with the thick and thin filaments within the sarcomeres of skeletal muscle. In most vertebrates, nebulin accounts for 3 to 4% of the total myofibrillar protein. Its size varies from 600 to 800 kD in a manner that is tissue-, species-, and developmental stage-specific. GENECALLING™ analysis reveals that nebulin is up-regulated in metastatic vs. non-metastatic thyroid cancer.

Nebulin is one of the autoantigens present in the peripheral blood of patients with Graves' disease. (See Kiljanski et al., Clin Exp Rheumatol 14 Suppl 15:S69–76 (1996)). It is possible that the overexpression of nebulin is a general feature of thyroid diseases associated with immune responses.

Genes Whose Expression is Newly Correlated with Metastatic Thyroid Cancer

Additional genes identified as being differentially expressed in studies leading to the invention include Type IV collagenase, neuropilin 1, calpain, clusterin, cathepsin E, cystatin B, lipocortin I, RIG-E, p8=candidate of metastasis 1, and protein phosphatase-1 gamma 1.

Their identification with the correct modulation indicates that metastatic tumor cells from different tissues or sites in the body might have an underlying common molecular pathway of gene expression. The discovery of such a common pathway has important implications for the diagnosis and treatment of metastatic carcinomas of all origins. The diagnostic, screening, and therapeutic applications are discussed in detail below. Moreover, these genes and treatments developed based on this list, including recombinant protein drugs, antibody drugs, and small molecule drugs may have a diagnostic role in metastatic carcinomas other than thyroid cancer.

Type IV Collagenase (MTC8)

Type IV collagenase (genBank#J03210) is a metalloproteinase that specifically cleaves type IV collagen, the major structural component of basement membranes. It is also known as matrix metalloproteinase-2 and gelatinase A. Degradation of type IV collagen in the basement membrane is an essential step in the invasive/metastatic behavior of tumor cells. Therefore the enhanced expression of the type IV collagenases, MMP-2 and MMP-9, or the lack of their inhibitors, TIMP-1 and TIMP-2, has been associated with tumor invasion and metastatic potential in several experimental models as well as in human tumors. Inhibitors of MMP-2 and MMP-9 prevent tumor growth and invasion in animal models. (See Koivunen et al., Nat Biotechnol 17(8):768–74 (1999)). GENECALLING™ analysis reveals that type IV collagenase is up-regulated in metastatic vs. non-metastatic thyroid cancer.

Neuropilin 1 (MTC9)

Neuropilin 1 (genBank#NM_003873) is a receptor for the axonal chemorepellent Semaphorin III in neurons. In endothelial and tumor cells, it is an isoform-specific receptor for vascular endothelial growth factor ("VEGF"). It acts by modulating VEGF binding to its receptor KDR and subsequent bioactivity. (See Soker et al., Int J Oncol 16(2):253–60 (2000)). A naturally-occurring soluble form acts as a powerful VEGF antagonist and has anti-tumor activity. GENECALLING™ analysis reveals that Neuropilin I is up-regulated in metastatic vs. non-metastatic thyroid cancer.

Ca2-activated neutral protease large subunit (CANP) (MTC10)

Ca2-activated neutral protease large subunit is also known as calpain (genBank#M23254). It is an intracellular cytoplasmatic non-lysosomal cysteine endopeptidase that requires calcium ions for activity. Many substrates of the calpain isoenzymes, such as the transcription factors c-Fos and c-Jun, the tumor supressor protein p53, protein kinase C, pp60c-src, and the adhesion molecule integrin, have been implicated in the pathogenesis of different human tumors. This suggests an important role for the calpains in malignant diseases. In renal cell carcinomas, there is a correlation of higher calpain I expression with increased malignancy. Within the clear cell carcinoma subset, tumor samples with advanced nodal status (N1 and N2) showed a significantly higher level of calpain I expression than did tumors without metastasis to regional lymph nodes. (See Braun et al., Int J Cancer 84(1):6–9 (1999)). An inhibitor of calpain was selectively cytotoxic to human tumor cells from chronic myeloid leukemia tissues, in a dose-dependent manner, and was also cytotoxic to Walker rat tumor cells. GENECALLING™ analysis reveals that calpain is up-regulated in metastatic vs. non-metastatic thyroid cancer.

Clusterin (MTC11)

Clusterin is also known as complement lysis inhibitor, SP-40,40, sulfated glycoprotein 2, testosterone-repressed prostate message 2, and apolipoprotein J (genBank#NP_001822). Sulfated glycoprotein-2 (SGP-2) is the major secreted product of Sertoli cells. It probably plays a critical role in spermatogenesis. Clusterin acts as a control mechanism of the complement cascade. Specifically, it prevents the binding of a C5b-C7 complex to the membrane of the target cell and, in this way, inhibits complement-mediated cytolysis. Apolipoprotein J is synthesized at high levels in degenerating hippocampus from individuals with Alzheimer's disease or Pick disease.

Clusterin may be a suicide gene active in programmed cell death. Transforming growth factor beta-1 up-regulates clusterin synthesis in thyroid epithelial cells and may be a marker of TGFbeta-mediated thyrocyte dedifferentiation. (See Wegrowski et al., Exp Cell Res 247(2):475–83 (1999)). Clusterin expression correlates with prostate cancer malignancy. Specifically, cells expressing clusterin are more resistant to androgen ablation and apoptotic stimuli.

GENECALLING™ analysis reveals that clusterin is up-regulated in metastatic vs. non-metastatic thyroid cancer.

Cathepsin E (MTC12)

Cathepsin E (genBank#J05036) is an immunologically discrete aspartic protease found in the gastrointestinal tract. It is overexpressed in pancreatic cancer and is associated with cellular dedifferentiation in cervical intraepithelial neoplasia. Cathepsin-positive inflammatory cells are infiltrated in and around the carcinoma tissue. Intensely stained inflammatory cells were often located in the stroma at the border of the carcinoma tissue. The incidence of this peculiar localization of intensely stained carcinoma cells significantly correlated with the progression of the carcinoma tissue. (See Matsuo et al., Hum Pathol 27(2):184–90 (1996)).

GENECALLING™ analysis reveals that cathepsin E is up-regulated in metastatic vs. non-metastatic thyroid cancer.

Cystatin B (MTC13)

Cystatin B, also known as Stefin B, (genBank#U46692) is a member of the superfamily of cysteine protease inhibitors, mainly inhibiting cathepsin L. An imbalance between the cathepsins and the cystatins has been observed at various levels in malignant human tumor tissue as compared to normal and benign tissue counterparts. These changes are highly predictive for the length of survival and may be used for the assessment of risk of relapse and death for breast, lung, brain, head and neck, ovarian, uterine, melanoma and colorecta cancers. Specifically, overexpression of cystatin B in colorectal cancer correlates significantly with Dukes' stage. Its level is the highest in stage D. (See Kos et al., Clin Cancer Res 6(2):505–11 (2000)). GENECALLING™ analysis reveals that cystatin B is up-regulated in metastatic vs. non-metastatic thyroid cancer.

Lipocortin I (MTC14)

Lipocortins are a family of calcium-dependent phospholipid-binding proteins with phospholipase A2 inhibitory activity. They are also known as annexins because they undergo Ca(2+)-dependent binding to phospholipids that are preferentially located on the cytosolic face of the plasma membrane. Lipocortin I (genBank#x05908) is overexpressed in human hepatocellular carcinoma (HCC). (See Masaki et al., Hepatology 24(1):72–81 (1997)). It is also overexpressed in breast tumors, where it might correlate with malignancy. (See Ahn et al., Clin Exp Metastasis 15(2):151–6 (1997)). GENECALLING™ analysis reveals that Lipocortin I is up-regulated in metastatic vs. non-metastatic thyroid cancer.

Lipocortin II (MTC15)

Lipocortins are a family of calcium-dependent phospholipid-binding proteins with phospholipase A2 inhibitory activity. They are also known as annexins because they undergo Ca(2+)-dependent binding to phospholipids that are preferentially located on the cytosolic face of the plasma membrane. Annexin II ( genBank#d00017) is a major cellular substrate of the tyrosine kinase encoded by the SRC oncogene. When it is exposed on the membrane, it is the receptor for tissue-type plasminogen activator and tenascin in endothelial cells where it mediates mitogenesis, cell migration, and loss of focal adhesions. (See Chung et al., Mol Biol Cell 7(6):883–92 (1996)). Increased levels of annexin II are observed in various cancer cells and tissues, and the molecule has been proposed as a marker of malignancy in vivo. GENECALLING™ analysis reveals that Lipocortin II is up-regulated in metastatic vs. non-metastatic thyroid cancer.

Retinoic acid induced RIG-E precursor (RIG-E) (MTC16)

Retinoic acid induced RIG-E precursor (genBank#U42376). The Ly-6 Ag family consists of glycosyl-phosphatidylinositol-anchored surface proteins with a molecular mass of about 15 kDa. Expression of RIG-E is not restricted to myeloid differentiation, as with other Ly-6 family member, but it is also present in thymocytes and in a number of other tissues at different levels. Low expression of RIG-E was correlated with the malignant potential human hepatocellular carcinoma. (See Kondoh et al., Cancer Res 9(19):4990–6 (1999)). GENECALLING™ analysis reveals that while RIG-E is up-regulated in metastatic vs. non-metastatic thyroid cancer when samples are compared group by goup, it is down-regulated when samples are compared one by one in the poisoning reaction.

P8 (Candidate of Metastasis I) (MTC17)

P8 (genBank#AF069073 or NM_012385) encodes a putative DNA-binding protein of the helix-turn-helix type. It is up-regulated in an animal model of breast tumor metastasis. In this model, constitutive expression of candidate of metastasis 1 seemed to distinguish breast cancer cells with metastatic potential from cells without metastatic potential. (See Ree et al., Cancer Res 59(18):4675–80 (1999)). It is induced by serum starvation and is mitogenic. (See Vasseur et al., Eur J Biochem 259(3):670–5 (1999)).

GENECALLING™ analysis reveals that P8 is down-regulated in metastatic vs. non-metastatic thyroid cancer.

Protein Phosphatase-1 Gamma 1 (MTC18)

Protein phosphatase-1 gamma 1 (genBank#L07395) was increased in about 50% in rat ascites hepatoma. It is significantly higher in malignant liposarcoma than in lipoma and in tumorous regions than in non-tumorous regions of malignant fibrous histiocytomas. (See Sogawa et al, Res Commun Mol Pathol Pharmacol 93(1):33–42 (1996)). The percentage of cells that stained positively with antiserum against PP1 catalytic subunit isoform PP1 gamma 1, was significantly higher in malignant osteogenic tumors (chondrosarcoma, osteosarcoma, and Ewing's sarcoma) and in malignant soft tissue tumors (liposarcoma and malignant fibrous histiocytoma (MFH)) than in benign tumors (osteochondroma, osteoblastoma, ossifying fibroma, enchondroma and lipoma). It is down-regulated by GA3P an extracellular polysaccharide that induces apoptosis in lymphoid and myeloid cell lines and it has a potential role in survival. GENECALLING™ analysis reveals that protein phosphatase-1 gamma 1 is up-regulated in metastatic vs. non-metastatic thyroid cancer.

In addition to the preceding genes, genes whose expression is newly correlated with metastatic thyroid cancer and which have not been previously associated with any type of cancer metastasis, were also differentially expressed in metastatic vs. non-metastatic thyroid cancer. These genes include tetraspan NET-1, periplakin, proteasome subunit HC5, ras GTPase-activating-like protein (IQGAP1), DUSP6 dual specficity MAP kinase phosphatase, SET binding factor (SBF1e), 5-lipoxygenase, calgizzarin, spermidine/spermine N1-acetyltransferase (SSAT), aldehyde dehydrogenase 2, gelsolin, integrin alpha-3, KIAA0937, KIAA 1131, antileukoprotease, DAP12, brain-specific STE20-like protein kinase 3 (MST-3b), peflin, kinectin, prostaglandin transporter hPCT, ribophorin II, PRO302, stimulated trans-acting factor, iduronate 2-sulfatase, mitochondrial proteolipid 68 MP, growth arrest specific transcript 5 gene, lactate dehydrogenase-A, 26-kDa surface protein TAPA-1 mRNA, and sodium dependent phosphate transporter isoform NaPi-3b.

These genes have been shown to be differentially expressed in tumor tissues, in animal models of human tumors, or in cell lines derived from human tumors, but the available literature does not describe a correlation between this expression and cancer progression and/or metastatic potential. It is likely that these genes contribute to the molecular phenotype of metastatic thyroid cancer and, as discussed above, to the phenotype of metastatic carcinomas in general. Genes in this group may have a diagnostic role in all metastatic carcinomas. Treatments may be useful in the treatment of all metastatic carcinomas.

Tetraspan NET-1 (MTC19)

Tetraspanins such as tetraspan NET-1, (genBank#AF065388) encode cell-surface proteins that span the membrane four times, forming two extracellular loops. They act as "molecular facilitators" by grouping specific cell-surface proteins and thus increasing the formation and stability of functional signaling complexes. NET-1 has been described by Serru et al., Biochim Biophys Acta 1478(l):159–163 (2000). This sequence is patented and the patent describes that it is expressed by prostate cancer and immunogenic in these patients. GENECALLING™ analysis reveals that tetraspan NET-1 is up-regulated in metastatic vs. non-metastatic thyroid cancer.

Periplakin (MTC20)

The cornified envelope is a layer of transglutaminase cross-linked protein that is assembled under the plasma membrane of keratinocytes in the outermost layers of the epidermis. The intermediate filament cytoskeleton of keratinocytes, composed of keratins that are expressed in specific expression pairs according to tissue and differentiation state, are interconnected through transmembrane protein complexes called desmosomes. They connect with the basement membrane via hemidesmosomes. The proteins that are thought to make contact with the intermediate filaments of keratinocytes belong to a family of proteins known as plakins. Paraneoplastic pemphigus is an rare autoimmune bullous skin disease and sera from these patients recognize periplakin (genBank#AF013717) and envoplakin. Cancers associated with paraneoplastic pemphigus are hematologic diseases such as non-Hodgkin's lymphomas and chronic lymphoid leukemia. GENECALLING™ analysis reveals that periplakin is up-regulated in metastatic vs. non-metastatic thyroid cancer.

Proteasome Subunit HC5 (MTC21)

Proteasome subunit HC5 (genBank#D00761) is part of the 20S proteasome. Proteasomes are multicatalytic proteinase complexes consisting of a set of non-identical polypeptide components. The 20S proteasome is increased in skeletal muscle from patients with cancer. (See Williams et al., Surgery 126(4):744–9 (1999)). GENECALLING™ analysis reveals that proteasome subunit HC5 is up-regulated in metastatic vs. non-metastatic thyroid cancer.

Ras GTPase-activating-like Protein (IQGAP1) (MTC22)

RasGTPase-activating-like protein (IQ GAP1) (genBank#NP_003861) inhibited the GTPase activity of cdc42Hs and rac, whereas no interaction with ras was detected. It interacts with the cytoskeleton and binds to actin, to members of the Rho family, and to E-cadherin. Calmodulin binds to IQGAP1 and regulates its association with Cdc42 and actin. Disruption of the binding of calmodulin to IQGAP1 enhances the association of IQGAP1 with components of the cadherin-catenin complex at cell-cell junctions, resulting in impaired E-cadherin function. Mutant IQGAP1 mice exhibit a significant (P<0.0001) increase in late-onset gastric hyperplasia relative to wild-type animals of the same genetic background. GENECALLING™ analysis reveals that IQ GAP 1 is up-regulated in metastatic vs. non-metastatic thyroid cancer.

DUSP6 Dual Specificity MAP Kinase Phosphatase (MTC23)

DUSP6 is also known as PYST1 (genBank#AB013382). Members of the mitogen-activated protein (MAP) kinase family play a pivotal role in cellular signal transduction. The dual-specificity phosphatases can reverse MAP kinase activation by dephosphorylating critical phosphotyrosine and phosphothreonine residues. DUSP6 is localized on 12q21, one of the regions of frequent allelic loss in pancreatic cancer. Reduced expression of the full-length transcripts was observed in some pancreatic cancer cell lines. (See Furukawa et al., Cytogenet Cell Genet 82(3–4):156–9 (1998)). GENECALLING™ analysis reveals that DUSP6 is up-regulated in metastatic vs. non-metastatic thyroid cancer. While this result is not in agreement with the reduced expression in pancreatic cell lines, there is evidence that another MAP kinase phosphatase, MKP-1, is overexpressed in prostate cancer and blocks Fas ligand (FasL)-induced apoptosis. (See Srikanth et al., Mol Cell Biochem 199(1–2):169–78 (1999)). It is possible that DUSP6 might have a similar activity in thyroid cancer.

SET binding Factor 1 (SBF1) (MTC24)

SET binding factor 1 (genBank#U93 181) was originally discovered by virtue of its interaction with a highly conserved motif, the SET domain common to protein like Suvar3–9, Enhancer-of-zeste, Trithorax, involved in epigenetic mechanisms of gene regulation. (See Cui et al., Nat Genet 18(4):331–7 (1998)). SET domains mediate highly conserved interactions with a specific family of proteins that display similarity with dual-specificity phosphatases (dsPTPases). SBF1 is a homolog of the dsPTPase myotubularin, but it lacks a functional catalytic domain which dephosphorylates phosphotyrosine and serine-containing peptides in vitro. It is possible that SBF1 acts by competing against dsPTPase for their target kinases. There is evidence that SBF1 behaves as an oncogene because overexpression of SBF1 can induce transformation or growth advantage. GENECALLING™ analysis reveals that SBF1 is down-regulated in metastatic vs non-metastatic thyroid cancer. While this result is not in agreement with the activities described above, in the context of the thyroid, SBF1 function might be to suppress the activity of DUSP6 and other dsPTPases that are important for the switch to metastatic tumor, where up-regulation of the dsPTPase DUSP6 is observed. 5-lipoxygenase (MTC25)

The enzyme 5-lipoxygenase (genBank#J03571) catalyzes 2 reactions in the formation of leukotrienes. The leukotrienes constitute a group of arachidonic acid-derived compounds with biologic activities in inflammation and immediate hypersensitivity. Recently the 5-lipoxygenase product, 5-HETE has been shown to be important for the survival of prostate cancer cells. (See Ghosh et al., Proc Natl Acad Sci USA 95(22):13182–7 (1998)). GENECALLING™ analysis reveals that 5-lipoxygenase is up-regulated in metastatic vs. non-metastatic thyroid cancer.

Calgizzarin (MTC26)

Calgizzarin (genBank#d38583) is a Ca2+-binding protein of the S100 family that has been implicated in the regulation of cytoskeletal function through its Ca2+-dependent interaction with annexin I. Calgizzarin expression was remarkably elevated in colorectal cancers, compared with expression in normal colorectal mucosa. (See Tanaka et al., Cancer Lett 89(2): 195–200 (1995)). Calgizzarin is part of the cornified envelope (CE) like periplakin and annexin I, two other genes described in this invention. GENECALLING™ analysis reveals that calgizzarin is up-regulated in metastatic vs. non-metastatic thyroid cancer, as are periplakin and annexin I. These results indicate that they might be part of a common pathway activated in metastatic cells.

Spermidine/Spermine N1-Acetyltransferase (SSAT) (MTC27)

Also known as diamine acetyltransferase and putrescine acetyltransferase (genBank#m77693). It is a rate-limiting enzyme in the catabolic pathway of polyamine metabolism. It catalyzes the N(1)-acetylation of spermidine and spermine, and, by the successive activity of polyamine oxidase, spermine can be converted to spermidine and spermidine to putrescine. It is up-regulated in prostate cancer, and this up-regulation correlates with malignancy. (Saverio et al., Cancer Res 60(l):28–3400 (2000)). GENECALLING™ analysis reveals that SSAT is up-regulated in metastatic vs. non-metastatic thyroid cancer.

Interestingly, for therapy considerations, increased transcription and ultimate superinduction of SSAT has been associated with the antineoplastic activity of several new antitumor polyamine analogues. (See Alhonen et al., Mol Pharmacol 55(4):693–8 (1999)). Potentially, polyamine analogues could have specific applications in the treatment of metastatic thyroid cancer.

Aldehyde Dehydrogenase 2 (ALDH-2) (MTC28)

Aldehyde dehydrogenase 2 (genBank#k03001) encodes the mitochondrial form of this alcohol metabolism enzyme. Inactive ALDH2 is a risk factor for multiple carcinoma of the esophagus in alcoholics due to the higher amounts of acetaldehyde produced by these individuals. It was also shown that ALDH2 is down-regulated or absent in tumor cell lines and in urethane-induced mouse liver tumors. (See Banfi et al., Mol Pharmacol 46(5):896–900(1994)). GENECALLING™ analysis reveals that ALDH-2 is down-regulated in metastatic vs. non-metastatic thyroid cancer.

Gelsolin (MTC29)

Gelsolin (genBank#X04412) severs actin filaments in the presence of submicromolar calcium concentrations. Circulating forms of gelsolin act to dissolve and then clear actin from the circulation. Plasma and cytoplasmic gelsolins are encoded by a single gene. Gelsolin is an obligate downstream effector of Rac for motility in dermal fibroblasts. It regulates phosphoinositide signaling pathways and ion channel function in vivo and acts as both a regulator and an effector of apoptosis. It is greatly decreased in many transformed cell lines and tumor tissues. This decrease correlates with malignancy in breast tumors. GENECALLING™ analysis reveals that gelsolin is up-regulated in metastatic vs. non-metastatic thyroid cancer. While this is in disagreement with the above data, at the same time, there is evidence that, in Tsc2 heterozygotic mice, renal cystadenomas develop from intercalated cells of the cortical collecting duct expressing gelsolin at high levels. (See Onda et al., J Clin Invest 104(6):687–95 (1999)).

Integrin Alpha-3 (MTC30)

Integrins encompass a family of cell-surface molecules, which play a crucial role in cell-cell and cell-extracellular matrix interactions. They are usually organized as heterodimeric transmembrane glycoproteins consisting of an alpha and beta chain. Integrin alpha-3 (genBank#AAA3612) together with beta 1 (VLA-3) functions as a receptor for fibronectin, laminin, and collagen. GENECALLING™ analysis reveals that integrin alpha-3 is up-regulated in metastatic vs. non-metastatic thyroid cancer, as is fibronectin. It is possible that the up-regulation of fibronectin and its receptor, integrin alpha-3, in metastatic thyroid cancer is important for the ability of these tumors to migrate in the extracellular matrix.

KIAA0937 (MTC31)

KIAA0937 (genBank#AB023154) is a homologue of human Deltex (DTX1), a member of the Notch signaling pathway. It contains a RING finger, which is a domain involved in protein-protein interactions or in DNA binding. Sbase indicates that it has homology to several transcription factors and to retinoic acid receptors and to serine proteases. It is possible that this protein binds a receptor-like notch, that is activated by processing and then translocated to the nucleus to activate trasncription. The putative chicken orthologue is expressed in many neural and sensory structures, such as neural tube, migrating neural crest cells, epidermal placodes, cranial ganglia, and the optic and otic vesicles. (See Frolova et al., Mech Dev 92(2):285–289 (2000)). GENECALLING™ analysis reveals that KIAA0937 is up-regulated in metastatic vs. non-metastatic thyroid cancer. SAGE analysis reveals that this gene is also expressed in colon cancer cell lines and tumors, in glioblastoma multiforne, breast cancers, and ovarian tumor cell lines. This indicates that overexpression of this gene may have a general role in tumorogenesis.

KIAA 1131 (MTC32)

KIAA1131 (genBank#AB032957) is described in Hirosawa et al., DNA Res. 6:329–336 (1999). This gene has homology to suppressor of Deltex and other ubiquitin ligase enzymes. This homology is extremely relevant to its potential role in thyroid and other metastatic cancers. In mammalian cells, notch has been shown to be important for survival and tumorogeneis. Deltex and suppressor of Deltex antagonize each other in their interaction with Notch. It is therefore likely that KIAA0937 and KIAA1131 are functional equivalent to Deltex and suppressor of Deltex. They identify a new Notch signalling pathway important for cell survival and metastatic potential. GENECALLING™ analysis reveals that KIAA1131 is down-regulated in metastatic vs. non-metastatic thyroid cancer. SAGE analysis reveals that this gene is down-regulated in prostate tumors compared with normal prostate, indicating a more general role of KIAA1131 downregulation in cancer.

Antileukoprotease (MTC33)

Antileukoprotease is also known as secretory leukocyte protease inhibitor (genBank#X04470). It is an acid-stable proteinase inhibitor with strong affinity for trypsin and chymotrypsin as well as for neutrophil lysosomal elastase and cathepsin-G. It is present in mucous fluids such as seminal plasma, cervical mucus, bronchial and nasal secretions, and tears. It was found to be expressed in lung, breast, oropharyngeal, bladder, endometrial, ovarian, and colorectal carcinomas. (See Garver et al., Gene Ther (1):46–50 (1994)). GENECALLING™ analysis reveals that antileukoprotease is up-regulated in metastatic vs. non-metastatic thyroid cancer. SAGE analysis indicate that antileukoprotease is up-regulated in ovarian tumors.

DAP12 (MTC34)

DAP12 (genBank#AF019562) is an Natural killer (NK)-cell receptor that lacks ITIM (immunoreceptor tyrosine-based inhibitory motifs) sequences. It has been proposed that DAP12 may activate, rather than inhibit, NK cells. DAP12 non-covalently associates with membrane glycoproteins of the killer-cell inhibitory receptor (KIR) family without an ITIM in their cytoplasmic domain. Crosslinking of KIR-DAP12 complexes results in cellular activation. Phosphorylated DAP12 peptides bind ZAP-70 and Syk protein tyrosine kinases, suggesting that the activation pathway is similar to that of the T- and B-cell antigen receptors. GENECALLING™ analysis reveals that DAP12 is up-regulated in metastatic vs. non-metastatic thyroid cancer. This up-regulation is likely due to lymphocyte infiltration of the metastatic thyroid cancers. SAGE analysis shows that its up-regulation is common to other cancers, like glioblastoma multiforme and ovarian tumors.

Brain-specific STE20-like Protein Kinase 3 (MST-3b) (MTC35)

The Sterile-20 (Ste20) family of serine-threonine kinases has been implicated in the activation of the stress-activated protein kinase pathways. MST3b (genBank#AAD42039) mRNA is restricted to the brain. MST3b, but not MST3, was effectively phosphorylated by the activation of cyclic AMP-dependent protein kinase (PKA) in both in vivo and in vitro assays. (See Zhou et al., J Biol Chem 275(4):2513–9 (2000)). GENECALLING™ analysis reveals that MST-3b is up-regulated in metastatic vs. non-metastatic thyroid cancer. SAGE analysis indicates that MST-3b is also up-regulated in ovarian tumors.

Peflin (MTC36)

Peflin (genBank#BAA85163) is a member of the five-EF-hand, Ca(2+)-binding protein family. It is similar to the apoptosis-linked gene 2 (ALG-2) (See Kitaura et al., Biochem. Biophys. Res. Commun. 263(1): 68–75 (1999)). ALG-2 is required for apoptosis, and ALG-2 depletion protects the mouse T cell hybridoma 3DO from programmed cell death induced by several stimuli, such as synthetic glucocorticoids, TCR, and Fas triggering. (See Lacana et al., J Immunol 158(11):5129–35 (1997)). GENECALLING™ analysis reveals that Peflin is down-regulated in metastatic vs. non-metastatic thyroid cancer. This suggests that tumor down-regulation of peflin might increase their resistance to apoptosis. SAGE analysis reveals that this down-regulation is also observed in breast, ductal carcinoma in situ vs. normal mammary epithelium and in colon cancer vs. normal colon.

Kinectin (MTC37)

Kinectin (genBank#NM_004986) is a receptor for the molecular motor kinesin, which is critically involved in microtubule-based vesicle transport and membrane trafficking. GENECALLING™ analysis reveals that kinectin is up-regulated in metastatic vs. non-metastatic thyroid cancer. It is cleaved by caspase 7 in cells subject to apoptotic stimuli. Therefore, its up-regulation might be related to survival. This hypothesis is confirmed by SAGE analysis. It is up-regulated by VEGF, a survival factor in human microvessel endothelial cells and by hypoxia. It is highly up-regulated in MDA453, from a human breast carcinoma with malignant effusion, estrogen receptor negative, obtained from a patient treated with radiation and chemotherapy. This evidence together with kinectin's up-regulation in thyroid cancer indicates a general role in promoting survival and metastatic potential.

Prostaglandin Transporter hPGT (MTC38)

Prostaglandins (PGs) play diverse and important roles in human health and disease. Specifically, elevated prostaglandin levels are associated with tumors and may promote tumor progression. PGT (genBank#u70867) is likely to have a role in the transport and/or metabolic clearance of PGs in diverse human tissues. GENECALLING™ analysis reveals that hPTG is down-regulated in metastatic vs. non-metastatic thyroid cancer. It is possible that the down-regulation of hPTG by metastatic thyroid cancer cells results in higher local concentration of prostaglandins that will favor tumor progression.

Ribophorin II (MTC39)

Ribophorin II (genBank#y00282) is part, together with ribophorin I (RI) and OST48, of the oligosaccharyltransferase (OST), which has its active site exposed on the luminal face of the endoplasmic reticulum (ER) and catalyzes the transfer of preassembled high mannose oligosaccharides onto certain asparagine residues of nascent polypeptides. Recently DAD1, the defender against apoptotic cell death was shown to be a member of this complex. DAD1 was initially identified as a negative regulator of programmed cell death indicating the possibility that OST and therefore ribophorin II have a role in cell survival. GENECALLING™ reveals that ribophorin II is up-regulated in metastatic vs. non-metastatic thyroid cancer. This result, together with the evidence that ribophorin II is overexpressed in primary colorectal cancer (See Hufton, FEBS Lett 463(1–2):77–82 (1999)), indicate that overexpression of ribophorin II promote a metastatic phenotype by increasing the ability of cells to survive.

Pro302 (MTC40)

This gene encodes a vitellogenic carboxypeptidase that is secreted protein. The pretin has anti-angiogenic activities that are useful for the treatment of cancer among other diseases. GENECALLING™ analysis reveals that Pro302 is down-regulated in metastatic vs. non-metastatic thyroid cancer. The down-regulation is in agreement with an anti-angiogenic and anti-tumor roles. Therefore, these studies indicate a specific use for Pro302 in the treatment of metastatic thyroid cancer.

Stimulated Trans-acting Factor (50 kDa) (MTC41)

Stimulated trans-acting factor (50 kDa) (Staf50) (genBank#X82200) is a member of the Ring finger family. It contains all the features of a transcriptional regulator able to initiate a second cascade of gene induction. It is induced by both type I and type II IFN in various cell lines (See Tissot et al., J Biol Chem 270(25):14891–8 (1995)). GENECALLING™ analysis reveals that Staf50 is up-regulated in metastatic vs. non-metastatic thyroid cancer. This might be a reflection of the high level of lymphocyte invasion of metastatic papillary carcinomas.

Iduronate 2-Sulfatase (MTC42)

GENECALLING™ analysis reveals that iduronate 2-sulfatase (genBank#M583420) is up-regulated in metastatic vs. non-metastatic thyroid cancer.

Mitochondrial Proteolipid 68 MP (MTC43)

Mitochondrial proteolipid 68 MP (genBank#AF054175) is expressed by human CD34(+) hematopoietic stem/progenitor cells. (See Mao et al., Proc. Natl. Acad. Sci. U.S.A. 95(14): 8175–8180 (1998)). GENECALLING™ analysis reveals that 68 MP is down-regulated in metastatic vs. non-metastatic thyroid cancer. It is likely that down-regulation of this gene indicates that cells in the metastatic tumors are losing their differentiation state and becoming similar to stem/progenitor cells.

Growth Arrest Specific Transcript 5 Gene (MTC43)

Growth arrest-specific transcript 5 (GAS5) (genBank#AF141346) was initially discovered in a screen for potential tumor suppressor genes expressed at high levels during growth arrest. GAS5 is a non-protein-coding multiple small nucleolar RNA (snoRNA) hostgene similar to UHG (U22 host gene). Encoded within the 11 introns of the mouse GAS5 gene are nine (10 in human) box C/DsnoRNAs predicted to function in the 2'-O-methylation of rRNA. In growing cells, active translation leads to rapid degradation of the spliced GAS5 RNA, whereas inhibition of translation causes the level of GAS5 transcript to rise. Likewise in growth-arrested cells, the spliced GAS5 RNA accumulates, apparently because it is sequestered in mRNP particles and is not translated. GENECALLING™ analysis reveals that GAS5 is up-regulated in metastatic vs. non-metastatic thyroid cancer. The differential expression of GAS5 in metastatic thyroid cancer may be related to an increase in the ability of these cells to survive stresses.

Lactate Dehydrogenase-A (MTC45)

GENECALLING™ analysis reveals that lactate dehydrogenase-A (genBank#X02152) is up-regulated in metastatic vs. non-metastatic thyroid cancer.

26-kDa cell surface protein TAPA-1 mRNA, complete cds.; CD81 (MTC46)

GENECALLING™ analysis reveals that CD81 (genBank#M33680) is down-regulated in metastatic vs. non-metastatic thyroid cancer.

Sodium Dependent Phosphate Transporter Isoform NaPi-3b AF 111856 (hs640_0) (MTC47)

GENECALLING™ analysis reveals that sodium dependent phosphate transporter isoform NaPi-3b (genBank#AF 111856) is up-regulated in metastatic vs. non-metastatic thyroid cancer.

Nucleic Acid Sequences Newly Described Herein

MTC48

An MTC48 nucleic acid sequence according to the invention includes the assembled sequence d0l0-145.3, or 88098062. GENECALLING™ analysis reveals that it is up-regulated in metastatic vs. non-metastatic thyroid cancer.

A human MTC48 nucleic acid sequence according to the invention (SEQ ID NO:1), along with its encoded amino acid sequence (SEQ ID NO:2), is provided below:

GGCGCCCGGGCGGTGCTGCGCTGCCA-
GAGCCCGCGCATGGTGTGGACCCAGGAC-
CGGCTGCACGACCGCCAGCGCGTGCTC-
CACTGGGACCTGCGCGGCCCCGGGGGTGGCCCC
GCGCGGCGCCTGCTGGACTTGTACTCG-
GCGGGCGAGCAGCGCGTGTACGAG-
GCGCGGGACCGCGGCCGCCTG-
GAGCTCTCGGCCTCGGCCTTCGACGACGGCAAC
TTCTCGCTGCTCATCCGCGCGGGTGGAG-
GAGACGACGCGGGGCTGTACACCTG-
CAACCTGCACCATCACTACTGCCACCTC-
TACGAGAGCCTGGCCGTCCGCCTGGAGGTCACCG
ACGGCCCCCCGGCCACCCCCGC-
CTACTGGGACGGCGAGAAGGAGGTGCTG-
GCGGTGGCGCGCGGCGCACCCGCGCT-
TCTGACCTGCGTGAACCGCGGGCACGTGTGGACC
GACCGGCACGTGGAGGAGGCTCAACAG-
GTGGTGCACTGGGACCGGCAGCCGC-

CCGGGGTCCCGCACGACCGCGCGGAC-
CGCCTGCTGGACCTCTACGCGTCGGGCGAGCGCC
GCGCCTACGGGCCCCTTTTTCTGCGC-
GACCGCGTGGCTGTGGGCGCGGATGC-
CTTTGAGCGCGGTGACTTCTCACTGCG-
TATCGAGCCGCTGGAGGTCGCCGACGAGGGCACC
TACTCCTGCCACCTGCACCACCATTACT-
GTGGCCTGCACGAACGCCGCGTCTTC-
CACCTGACGGTCGCCGAACCCACGCG-
GAGCCGCCCCCCGGGGCTCTCCGGGCAACGGCT
CCAGCCACAGCGGCGCCCAGGCCCA-
GACCCCACACTGGCGCGCGGCCA-
CAACGTCATCAATGTCATCGTC-
CCCGAGAGCCGAGCCCACTTCTTCCAGCAGCT
GGGCTACGTGCTGGCCACGCTGCT-
GCTCTTCATCCTGCTACTGGTCACTGTC-
CTCCTGGCCGCCCGCAGGCGCCGCGGAG-
GCTACGAATACTCGGACCAGAAGTCGGGAAAGT
CAAAGGGGAAGGATGTTAACTTGGCG-
GAGTTCGCTGTGGCTGCAGGGGACCA-
GATGCTTTACAGGAGTGAGGACATC-
CAGCTAGATTACAAAAACAACATCCTGAAGGAG
AGGGCGGAGCTGGCCCACAGCCCCCTGC-
CTGCCAAGTACATCGACCTAGA-
CAAAGGGTTCCGGAAGGAGAACTG-
CAAATAGGGAGGCCCTGGGCTCCTGGCTGGGCC
AGCAGCTGCACCTCTCCTGTCTG TGCTC-
CTCGGGGCATCTCCTGATGCTC-
CGGGGCTCACCCCCTTCCAGCGGCTG-
GTCCGCTTTCCTGGAATTTGGCCTGGGCGTATGC
AGAGGCCGCCTCCACACCCCT CCCCCAGGGGCT-
TGGTGGCAGCATAGCCCCCACCCCTGCG-
GCCTTTGCTCACGGGTGGGCCCTGC-
CCACCCCTGGGCACAACCAAAATCCCACTGATG
CCCAT CATGCCCTCAGACCCTTCTGGGCTCTGC-
CCGCTGGGGCCTGAAGACATTCCTG-
GAGGACACTCCCATCAGAACCTGGCAGC-
CCCAAAACTGGGGTCAGCCTCAGGGCAGGAGT
CCCACTCCTCCAGGGCTCTGCTCGTC-
CGGGGCTGGGAGATGTTCCTGGAGGAG-
GACACTCCCATCAGAACTTGGCAGCCT-
TGAAGTTGGGGTCAGCCTCGGCAGGAGTCCCACT
CCTCCTGGGGTGCTGCCTGCCACCAA-
GAGCTCCCCACCTGTACCACCATGTGG-
GACTCCAGGCACCATCTGTTCTC-
CCCAGGGACCTGCTGACTTGAATGCCAGCCCTT
GCTCCTCTGTGTTGCTTTGGGCCAC-
CTGGGGCTGCACCCCTGCCCTTTCTCT-
GCCCCATCCCTACCCTAGCCTTGCTCT-
CAGCCACCTTGATAGTCACTGGGCTCCCTGTGAC
TTCTGACCCTGACACCCCTCCCTTG-
GACTCTGCCTGGGCTG-
GAGTCTAGGGCTGGGGCTACATTTGGCT-
TCTGTACTGGCTGAGGACAGGGGAGGGAGTGAA
GTTG GTTTGGGGTGGCCTGTGTTGCCACTCT-
CAGCACCCCACATTTGCATCTGCTGGTG-
GACCTGCCACCATCACAATAAAGTC-
CCCATCTGATTTTAAAAAAAAAAAAAAAAAAAA
AAAAAAA (SEQ ID NO:1)

Amino acid sequence: (SEQ ID NO:2)
MVWTQDRLHDRQRVLHWDLRGPGGGPAR-
RLLDLYSAGEQRVYEARDRGRLELSASA-
FDDGNFSLLIRAVEETDAGLYTCNLHH-
HYCHLYESLAVRLEVTDGPPATPAYWDGEKEVLAVA
RGAPALLTCVNRGHVWTDRHVEEAQQV-
VHWDRQPPGVPHDRADRLLDLYASGER-
RAYGPLFLRDRVAVGADAFERGDFSL-
RIEPLEVADEGTYSCHLHHHYCGLHERRVFHLTVA
EPHAEPPPRGSPGNGSSHSGAPGPDPT-
LARGHNVINVIVPESRAHFFQQLGYV-
LATLLLFILLLVTVLLAARRRRGGYEYS-
DQKSGKSKGKDVNLAEFAVAAGDQMLYRSEDIQL
DYKNNILKERAELAHSPLPAKYIDLDKGFRKENCK
(SEQ ID NO:2)

A mouse MTC48 nucleic acid sequence according to the invention (SEQ ID NO:3), along with its encoded amino acid sequence (SEQ ID NO:4), is provided below:
(SEQ ID NO:3)
TTCGGCACAGGACCTGCACCATCAC-
TACTGCCACCTCGATGAGAGCATGGCT-
GTGCGCCTCGAGGTTACAGAGGATC-
CCCTATTAAGTCGCGCATACTGGGACGGTGAGAA
GGAAGTGTTGGAGGTGGCCCATG-
GCGCGCCGGCACTGATGACCTGCAT-
CAACCGTGCGCACGTGTGGACTGACCGC-
CATTTAGAGGAGGCGCAACAGGATAGACAATT
GGGACGACAGCTACCTGGGGTGTCACAC-
GACCGCGCCGACCGCCTGCATGACCTG-
TATGCATCTGGCGAGCGCCGCGC-
CTATGGGCCACCCTTCCTGCGTGATCGCGTGTCA
GTGAACACCAACGCTTTTGCACGCGGT-
GACTTCTCCCTACGCATCGATGAGCTG-
GAGCGAGCTGATGAGGGCATCTATTCCT-
GCCACCTGCACCATCACTACTGTGGCCTCCACGA
GCGCCGAGTCTTCCACCTACAGGTCACA-
GAGCCTGCCTTTGAGCCACCAGCTCGT-
GCTTCTCCTGGCAATGGGTCTGGTCA-
CAGCAGTGCTCCTAGCCCAGATCCCACCCTGA
CCCGAGGCCACAGCATCATCAATGT-
CATTTGTCCCAGAGGACCACACA-
CATTTCTTCCAGCAACTGGGCTATGTGT-
TGGCCACGCTGCTGCTCTTCATCTTGCTGCTCATC
ACTGTAGTCCT GGCTACACGATATCGTCACAGCG-
GAGGATGCAAGACGTCGGA-
CAAAAAAGCTGGGAAGTCAAAGGGGAAG-
GAATGTCGACACGATGGTGGAGTTTGCTGTAGCC
ACAAGGGATCAG GCTCCATATAGGACTGAGGA-
CATCCAGCTAGATTACAAAAACAACATC-
CTGCGGTATTCCTGGCTCTTCTCAGCG-
GCTGGTCCGACTTAC
CTAGAAACTTGGCAGAGCAGCTGCCTG-
TACTTTGCCCTTCCTAGAATCGCCAC-
CCCTCATCTTGGTGAGCAACTGTGGGT-
TCCCTAGAGACTCTGGTATAGTACGATTGCTGCCC
TTCACCTGTGCCCACTGATGGTTGTAC-
CCCCAACTTAAACACAACAAAGATCCCT-
TGTTAATATCCACCAAATG CAAAGTCCCTCGTGGC-
CTCTTACTGCTAGGGTCAGGAAGACACTTAAAAA
TTCCAGTTAAGACTCCCTAGCCACCAGT-
TAAACACATTAGCCATTGTC-
CTGGGGGGTCTCCTGAGCTGCATTGTGC-
CTGTGTACTGTTCAG (SEQ ID NO:3)

Mouse Amino Acid Sequence: (SEQ ID NO: 4)
SAQDLHHHYCHLDESMAVRLEVTED-
PLLSRAYWDGEKEVLEVAHGA-
PALMTCINRAHVWTDRHLEE-
AQQDRQLGRQLPGVSHDRADRLHDLYASGERRAY
GPPFLRDRVSVNTNAFARGDFSLRIDEL-
ERADEGIYSCHLHHHYCGLHERRVF-
HLQVTEPAFEPPARASPGNGSGH-
SSAPSPDPTLTRGHSIINVICPRGPHTFLPATGLCVGH
AAALHLAAHHCSPGYTISSQRRMQD-
VGQKSWEVKGEGMSTRWWSLL (SEQ ID NO:4)

Figure 1:
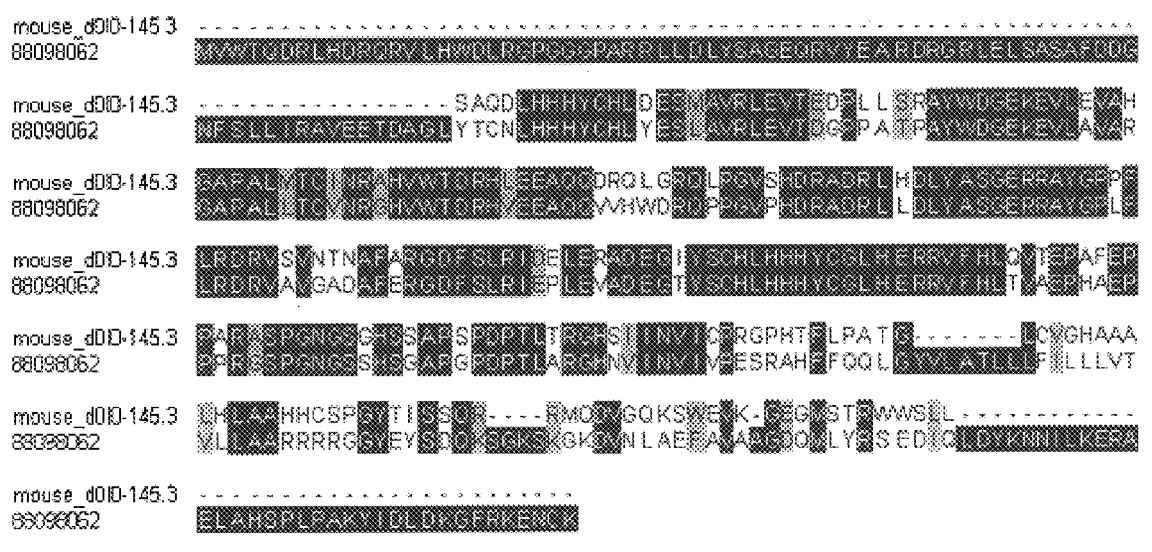

FIG. 1 shows the sequence homology between a human MTC48 amino acid sequence and a mouse MTC48 amino acid sequence according to the invention. The conserved regions in each amino acid sequence are highlighted in black.

Psort analysis indicates that this is a transmembrane protein. The values are mitochondrial inner membrane P=0.8207 and plasma membrane P=0.7000. Because the values are so similar, a definitive cellular localization cannot yet be predicted.

Pfam analysis indicates the presence of two immunoglobulin-like domains in the protein. One extends from amino acid 23 to amino acid 81, and the includes amino acid 121 to amino acid 216. These regions are also identified using Sbase analysis. Sbase analysis also indicates that the encoded MET48 polypeptide has homology to the COOH region of the HB-EGF-like family. Blocks analysis finds homology to metallo-proteins involved in oxygen carrying or electron transfer and to G-protein coupled receptors.

FIG. 2 presents a hydrophobicity analysis of a human MTC48 polypeptide. A transmembrane domain is present between amino acids 260 to 300 When exposed on the plasma membrane, this region presents a desirable target for immunotherapy. A MMTC48 is a GPCR or a protein involved in enzymatic activity, it is potentially a target for small molecule therapy.

MTC49

A MTC49 nucleic acid sequence according to the invention was assembled using sequences from AC024267, which is derived from human chromosome 17, as well as sequences expressed in thyroid glands. The assembled sequence is downregulated in metastatic vs. non-metastatic cancer cells. The presence of sequences from thyroid glands supports the hypothesis that this gene is normally expressed in the thyroid gland and that it is down-regulated in metastatic thyroid tumors.

A human MTC49 nucleic acid sequence according to the invention (SEQ ID NO:5), along with its encoded amino acid sequence (SEQ ID NO:6), is provided below:

Human MTC49 cDNA (SEQ ID NO: 5)
CCAGCGCCATCATCAGATGGCAAGNT-
CAGCCCCGGCACGTTATCCATAG-
GAAGCGCTTTAACCGTACCCTCTTTC-
CCAACCAACTCTACTGCCATGGTGGACCTCACC
AACTCACTTCGAGCATTTATGGATGT-
CAATGGAGAAATCGAGATAAATATGCTG-
GACGAGAAGCTGATCAAGTTTCTGGCCT-
TGCAGAGAATACATCAGCTTTTCCCCTCCCGGGT
CCAACCTTCACCGGGCAGTGTCGGGACA-
CATCAGCTGGCTTCTGGAGGGCACCA-
CATAGAAGNNNNJNNNNNNNNNTGTA-
CAGGCCCGAGCTGTGTTCTACCCCCTCTTAGGGTT
GGGAGGAGCTGTGAACATGTCCTATC-
GAACCCTCTACATCGGGACAGGAGCTGA-
CATGGATGTGTGCCTTACAAACTATGGT-
CACTGTAACTACGTGTCCGGGAAACATGCCTGCAT
ATTCTACGATGAGAATACCAAACATTAT-
GAGCTGTTAAACTACAGTGAGCATGGA-
CAACGGTGGACAATGTGCTGTATTCAT-
GTGACTTCTCGGAGAAGACCCCGCCAACCCCCC
AAGCAGTATTGTTGCCAAAGTGCAGAGT-
GTCATCAGGCGCCGCCGGCACCAGAAA-
CAGGACGAAGAGCCAAGTGAGGAG-
GCAGCCATGATGAGTTCCCAGGCCCAGGGGCCGC
AGCGGAGACCCTGCAATTGCAAAGCCAG-
CAGCTCGAGCTTGAT-
TGGGGGCAGTGGGGCCGGCTGG-
GAGGGCACAGCCTTACTGCACCATGGCAGCTACA
TCAAGCTGGGCTGCCTGCAGTTTGTCT-
TCAGCATCACTGAGTTTGCGACCAAA-
CAGCCCAAAGGCGATGCCAGCCTGCTG-
CAGGATGGGGTCTTGGCCGAGAAGCTCTCTCTC
AAGCCCCACCAGGGCCCTGTGCT-
GCGCTCCAACTCTGTTCCTTAGGACTG-
GCGGCTACCCCGCCACTGGCCTGTACAC-
CCACCCAAGACTCCTGCAATGCAAAAATGTACAC
AAACCAAGCCCGGGTGTTTTCTATACTC-
TACCAGAAACCCTTCAACTA-
CAATCTTTGCATGAAATGAAGAAAAC-
CTTTTGACTGTTTTTAAAAATCCTTTTTCTTTTCT
CAAGTTCTAGGGGGCATTTGCA-
CATATATTTGTACTCAACATTTCATGG-
GAAAGCGGCAGACCTGAGCTGAGGAA-
CAGCGTGGNGCAGGGAGGGAAAGACCCAGGGT
CTGGACANTTTCTCCAACACAAAANC-
CTTTCCCACCCANCTTCCTGCTTCCTTC-
CCCTTCGNGCNCCCCATTGTAAAATAAT-
CAGGAAACTTGTTCTATTTTGTGGCAGTGACAATA
GTTTATATTAA AAGAAAAAATACAGTTTTCATAAC-
CACAAATCTATTCAATATCATTGTTT-
TATTTAATATAAAGATCGCTACCCACCT-
TCCTTCCATGGTTCCCACCCTCCACGTTATTTTCC
CTTTC TGCAGCGGTTGCACTACAGGTAGCTACT-
GTGTATTATGGACAAATGAGAAATGAAT-
TCTTTTTCTGGCTGTCCATCTATTT-
TATTTCAAATAAGGAAAAGTGTATTTGGATTTTGT
GTAAATACATCTAGTGATGA-
CATTTTTTCAATGTTTTAAAAACCGTG-
TACAGTACTACATGTGGTA-
GAGCGTTTTCTCAAATTGTCTATTGTAGCAAAAAT
GTTTTTGTCGTAAACCTGTTTTGTCTC-
CTTTTTTTGTTCTCTTGCCACTTCTCTC-
CTCTTCCTCCTGCCCCTGGTTCCCTC-
CTCTCCTCCCACCCCCACAACCAGTACCAATGTA
CATAGTAATTGTAATGTTTTAGACTTTA-
CAGAAACTTTCCTGTATTCTG-
TATATAAAAACAAAAATACT-
TCAAAAAAAAAAAAAAAAAAA (SEQ ID NO:5)

Human MET49 Polypeptide (SEQ ID NO:6)
MVDLTNSLRAFMDVNGEIEINMLDEK-
LIKFLALQRIHQLFPSRVQPSPGSVGTH-
QLASGGHHIEXXXXXVQARAVFY-
PLLGLGGAVNMSYRTLYIGTGADMDVCLTNYGHC
NYVSGKHACIFYDENTKHYELLNYSEH-
GTTVDNVLYSCDFSEKTPPTPPSSI-
VAKVQSVIRRRHQKQDEEPSEE-
AAMMSSQAQGPQRRPCNCKASSSSLIGGSGAGWE
GTALLHHGSYIKLGCLQFVFSITEFAT-
KQPKGDASLLQDGVLAEKLSLKPHQGPVLRSNSVP
(SEQ ID NO:6)

A mouse MTC49 nucleic acid sequence according to the invention (SEQ ID NO:7), along with its encoded amino acid sequence (SEQ ID NO:8), is provided below:

Mouse cDNA (SEQ ID NO:7)
CCCAAATGCCACCCTGGGTGCTCACTC-
CCCCCCAGGCTGCAGGAGACAGTATCT-
TGGCCACAGGTGCCAACCAACGATTCT-
GCTCACCAGCGCCATCATCAGCTCTAGGAGTTCC
AGAGCCTGTGGGTTGAGAATCAAGAAGG-
GAACATCACCTTGGGTCCGAAATCCA-
GAACTGTCTCAACAATGGGGATTGGAC-
CGGTGGGTTTCCCTCAGGCGACCCAACTCTACTG
CCATGGTGGACCTCACCAACTCACTTC-
GAGCATTTATGGATGTCAACG-
GAGAAATCGAGATAAATATGTTGGAT-
GAGAAGCTGATCAAGTTTCTGGCCTTGCAGAGA GTACATCAGCTTTTCCCTTCCCGGGTC-
CAAGCTTCACCGGGCAATGTTGGGACA-
CATCCGCTGGCTTCTGGAGGGCACCAC-
CCAGAAGTGCAAAGAAAGGAGGTACAGGCCCGA
GCTGTGTTCTGCCCCCTCTTAGGGTTGG-
GAGGAGCTGTGAACATGTGCTATCGAAC-
CCTCTACATCGGGACAGGAGCTGACATG-
GATGTGTGCCTTACAAACTATGGTCACTGTAACTA
CGTGTCCGGGAAACATGCCTGCATATTC-
TACGATGAGAATACCAAACATTAT-
GAGCTGTTAAACTACAGTGAGCATGGGA-
CAACGGTGGACAATGTGCTGTATTCATGTGACTT
CTCTGAGAAGACCCCGCCAAC-
CCCCCCAAGCAGTATTGTTGCCAAAGTA-
CAGAGTGTCATCAGGCGCCGCGAGCAC-
CAGAAACAGGATGAAGAGCCAAGTGAGGAGGCA
GCCATGATGAGTTCCCAGGCCCAGGGgc-
CACAGCGGAGACCCTGCAATTGCAAAGC-
CAGCAGCTCAAGCTTGAT-
TGGGGGCAGTGGGGCCGGCTGGGAGGGCACAGC
ATTACTCCACCATGGCAGCTACAT-
CAAGCTGGGCTGCCTGCAGTTTGTCT-
TCAGCATCACTGAGTTTGCGACCAAA-
CAGCCCAAAGGCGATGCCAGCCTGCTGCAGGAT
GGGGTCTTGGCTGAGAAACTCTCTCT-
CAAGCCCCATCAGGGCCCTGTGCT-
GCGCTCCAACTCCGTTCCCTAGGCCAT-
TGGCCTGGACGCCCACCCAAGACTCCTGCAATGC
AAAAATGTACACGAACCAAGCCTGGGT-
GTTTTCTATACCAGAAACCCTCAACTA-
CAATCTTTGCATGAAATGAAGAAAAC-
CTTTTGACTGTTTTTTAAGACTTTTTTTCTTTTCTC
AAGTTCTAG GGGGCATTTGCACATATATTTGTACT-
CAACATTTCATGGGAAAGCGGCAGATC-
CGCGCTGAGGAGCAGCGAGGGCAGGGA-
CAGGAGGCCCTGGTCTGGACACTTCCTCCAGCAC
AATCCCTTCCCCCGCCTCCTGCTCCTC-
CCCCTCGACCGCCTGCCCACTGTTG-
TAAAATAATCAGAAACTTGTTC-
TATTTTGTGGCAGTGACAATAGTTTTATATTAAAA
GAAAAAAATACAGTTTTCATACAG-
CAAAATCTATACAATATCATTGTTT-
TATTTAATATAAAGATCGCTACCCACTC-
CTTTCCATGGTTCCCACCCTACAAGGACTTCCCC
TCTCTGCAGCAGTTGCACTACAGGTAGC-
TACTGTGTATATGGACAAATGAGAAAT-
GAATCCTTTTTTCTGGCTGTCCATC-
TATTTTATTTCAAATAAGGAAAAGTGTATTTGGA
TTTTGTGTAAATACATCTAGTGATG-
GCATTTTTTCAATGTTTTTAAAAGCTGT-
GTACAGTACATGTGGTAGAGTGTTTCT-
CAAATTGTCTATTGTAGCAAAGGCGTTTTTGTCGT
AAACCTGTTCTGTGTCCTTTTTTGTTCT-
TACCACTTCTCTTCCTCCTCACCCCA-
GATACTTCCTCTTCCCCACAACCAATG-
TACATAGTAATTGTAATGTTTAGACTTGACAG
AAACTTTCCTGTATTCTG-
TATATAAAAACCAAAAAATACTTCAAATT Mouse Peptide (SEQ ID NO: 8 )
MVDLTNSLRAFMDVNGEIEINMLDEK-
LIKFLALQRVHQLFPSRVQASPGNVGTH-
PLASGGHHPEVQRKEVQARAVFC-
PLLGLGGAVNMCYRTLYIGTGADMDVCLTNYGHC
NYVSGKHACIFYDENTKHYELLNYSEH-
GTTVDNVLYSCDFSEKTPPTPPSSI-
VAKVQSVIRRREHQKQDEEPSEE-
AAMMSSQAQGPQRRPCNCKASSSSLIGGSGAGWE
GTALLHHGSYIKLGCLQFVFSITEFAT-
KQPKGDASLLQDGVLAEKLSLKPHQGPVLRSNSVP FIG. 3 shows the sequence homology between a human MTC49 amino acid sequence and a mouse MTC49 amino acid sequence according to the invention. The conserved regions in each amino acid sequence are highlighted in black.

MTC49 most likely encodes a new transcription factor. This conclusion is supported by Psort analysis suggesting a nuclear location (nucleus P=0.6000). A nuclear location for the encoded MTC49 polypeptide is also likely in view of the homology of the encoded polypeptide to O60129 FORK HEAD PROTEIN TYPE TRANSCRIPTION FACTOR (46% ID in the region between 96 to 191aa) and weaker homology to homeobox proteins.

Also included in the invention is a nucleic acid encoding a polypeptide having an FHA domain. The FHA domain is a putative nuclear signaling domain found in protein kinases and transcription factors. This sequence is up-regulated in the GENECALLING™ analysis described herein. Its nucleotide sequence is provided in SEQ ID NO:9
AATTTATAAAGAAAAGACATTTATTTTG-
GCTCACAATTCTGCAGGCTGTACTG-
GCATGGCACCAACATTTGCTCAGCT-
TCTGGTGAGGGCCTCAGGAAGCTTACAGTAAAGGC
GGAAGGTGAAGGGGGAGCAGGCATATCA-
CATGGCGAGAAAGAGGGGAGAGGTCTCA-
GACTCTTTTAAACAACCATATCTATGT-
GAATTGAGTGAGAACTCACTCATCACCAAGGAG
ATGGTGCTGAGCCATTCATGAAGGATC-
CTCTCTCATGATCCAAATACTTCCCAC-
CAGGCTCCACTTCCAACACTGGGAATTA-
CATTTCAACATGAGATTTGGAGGGGACGAGCAT
CCAAACCATATCAGATGGTGAGACAG-
GAGAACTTTGTGTGTCCCAGCTGCACTG-
GTCTGAAGATATAACTAAGTCCCTG-
GACTTTTTCTCCCTTAATTGGAGAATTCCTAATG
TTCCATGATCAGCCTGATTGACCAGTG-
GCTGACTGGTCCTGAGAGGG-
GAGATAAAAACAGACACACAGCTTTCTC-
CATAGACAAATCTCAACACTTTC (SEQ ID NO:9)
MTC50

An MTC50 nucleic acid according to the invention was assembled and named 95199195. GENECALLING™ analysis reveals that this gene is up-regulated in metastatic vs. non-metastatic thyroid cancer. The assembled sequence is part of the genomic region assigned to inosine-5'-monophosphate dehydrogenase type II, but it represents a different gene as discussed by Zimmermann et al. (See Zimmermann et al., J Biol Chem 272(36):22913–23 (1997)). Zimmerman et al. showed that there is a 2-kb gene that is oriented tail-to-tail with respect to the IMPDH type II gene and terminates 1 kb 3 to it.

An MTC50 nucleotide sequence according to the invention that corresponds to the reverse complement (SEQ ID NO: 10) of 95199195 is provided below. The amino acid sequence (SEQ ID NO:11) of an MTC polypeptide is also provided
GGGGCTAGAAGTCTGGCACCCACCGC-
CTGGCCAGGTGTTCGGGACGCGACCAG-
GTGGGCGGTCGCCGCCCCGGGAGCGCG-
GCTTAATAGCTGAGAGCCCGGGGGCCAGGCCGC
GGCTGCGGCCCAGGCAACGCCCT-
GAGGGTGGCCACGCTGCCAGGTGTTC-
CACTCCCCCGGGACTATGGGCAAGGGC-
CGGGGCGGGGAGGGCGGCAGGTGCTGACACTGG
AGCTGCCCGGAGTCGGGGAACTCGGC- CTCCTAAGACTGAGGACACTCGCCT-
GCTGGGCCGGTCGAGCTGTGCGGTGC-
CCTCCGGACGCAGGGGGCGCTGCAGCCACGCT
GGGTCAGGCTCCGCAGGCCCTCCCAAC-
CCGGGGACTAACGGCGCCGGTGACGACT-
TCGCCGCGCGTTGGTCAGCCATGGCCAC-
CGCTCTCGCGCTACGTAGCTTGTACCGAGCGCGA
CCCTCGCTGCGCTGTCCGCCCGT-
TGAGCTTCCCTGGGCCCCGCGGC-
GAGGGCATCGGCTCTCGCCGGCGGAT-
GACGAGCTGTATCAGCGGACGCGCATCTCTCTGC
TGCAACGCGAGGCCGCTCAGGCAATGTA-
CATCGACAGCTACAACAGCCGCGGCT-
TCATGATAAACGGAAACCGCGTGCTCG-
GCCCCTGCGCTCTGCTCCCGCACTCGGTGGTGCA
GTGGAACGTGGGATCCACCAGGACAT-
CACCGAAGACAGCTTTTCCTCTTCTG-
GTTGCTGGAGCCCCCGGATAGAGATCGTG-
GTGGTGGGGACTGGAGACCGGACCGAGAGGCTG
CAGTCCCAGGTGCTTCAAGCCATGAG-
GCAGCGGGGCATTGCTGTGGAAGTGCAG-
GACACGCCCAATGCCTGTGCCACCT-
TCAACTTCCTGTGTCATGAAGGCCGAGTAACTGG
AGCT GCTCTCATCCCTCCACCAGGAGGGACT-
TCACTTACATCTTTGGGCCAAGCTGCT-
CAATGAACCGCCAGGAACTGACCTGCT-
GACTGCACTCTGCCAGGCTTCCCAATGCTTTCAC
TCTTATCTACCCTTTGGCACTTATCT-
TGCTTATCAACATAATAATTTATACACT-
TCTCCCATTTTGTATCAGGTGTGT-
TGCTGGCCAGGAGCTGATGGCTCACTGGGCTCTT
GGAGGGGAATGTGAAGAAACCAAGGAGT-
CACTTTTTCATCTAGATTACTTAGGAT-
TCCTTGACTTTTCAGAAGTCGGGAAG-
CAGTATGTTTGCCTGTTGTAGACCTACTTGCTCAC
ATGCAGATTTGAGAGGACCTCAACG-
GCTTTTCTCACAAAAAAAAA (SEQ ID NO: 10)

Amino Acid Sequence (SEQ ID NO: 11)
MATALALRSLYRARPSLRCPPVELP-
WAPRRGHRLSPADDELYQRTRIS-
LLQREAAQAMYIDSYNSRGFMINGNRV-
LGPCALLPHSVVQWNVGSHQDITEDSFSLFWLLEP
RIEIVVVGTGDRTERLQSQVLQAMRQR-
GIAVEVQDTPNACATFNFLCHEGRVT-
GAALIPPPGGTSLTSLGQAAQ The encoded MTC50 amino acid polypeptide is similar to a hypothetical protein present in public databases that is named Q9Y3Z0. Alignment of these two sequences reveals that they are identical in their COOH terminus but diverge in the first 50 amino acids (out of 190 amino acids).

Figure 4:
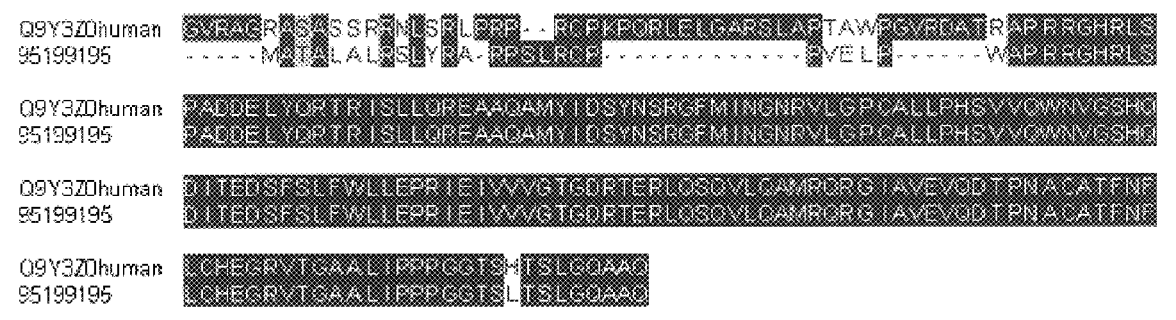

FIG. 4 shows the sequence homology between a human MTC50 amino acid sequence and the hypothetical protein Q9Y2Z0. The conserved regions in each amino acid sequence are highlighted in black.

This sequence is similar to the rat gene E3-3 (AAB54063), an entry in the database that is annotated as a novel nuclear protein that is predominantly expressed in testis. Psort puts it in the mitochondrial matrix space P=0.8414. BlastP against the database finds homology to several eukaryotic hypothetical proteins and bacterial membrane proteins. Blocks analysis shows the polypeptide has homology to acid phosphatase in the NH terminus and to CYCLOPHILIN-TYPE PPIASE FAMILY, in the COOH terminus. Sbase and Prodom finds that the NH terminus is similar to the transit peptide of FUMARATE HYDRATASE, another genomically encoded protein that is localized to the mitochondrial membrane. Sbase also shows similarity with the rat serotonin (5-HT6) receptor, a G-protein coupled receptor (48% over the length of the protein).

Figure 5:
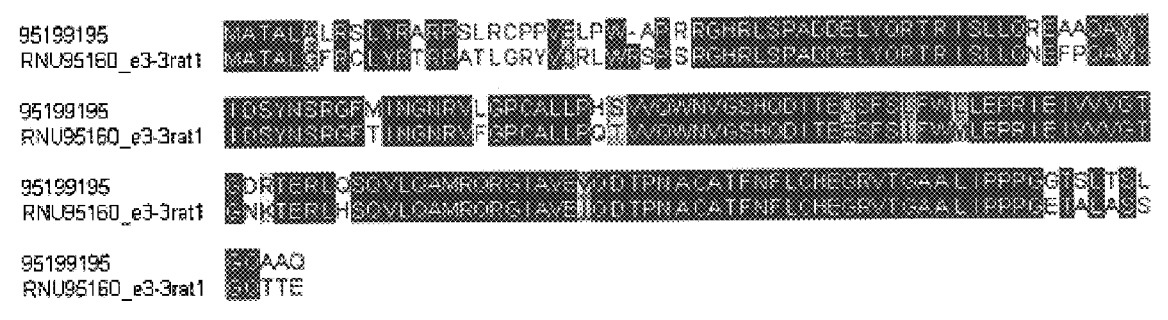

FIG. 5 shows the sequence homology between a human MTC50 amino acid sequence and the rat gene E3-3 (AAB54063). The conserved regions in each amino acid sequence are highlighted in black.

Cyclophilins are known to be involved in stress-related responses, and they are up-regulated in cancer. This sequence might represent a new member of this family that localizes to the mitochondrial membrane. Inhibition of the Ppiase activity of this protein may be useful to treat cancer.

MTC51

A nucleotide sequence of an MTC51 nucleic acid is provided below (SEQ ID NO:12). GENECALLING™ analysis reveals that it is up-regulated in metastatic vs. non-metastatic thyroid cancer. This sequence finds no match or similarity with sequences in any database.

Nucleic acid sequence (SEQ ID NO: 12)
tgtacagcagccgcttgaagtcctttaa-
gangaaatctcttttcttgncgngt-
tganccttccacggngtanttgacgtcccctggcntggttttttgatccgga Conceptual translation of this nucleic acid sequence reveals that it can code for two open reading frames ("ORFs"). This indicates the possibility that it can represent a fragment of the coding region of a novel gene.

ORF1, Frame -1 SGSKTXPGDVXYXVEG-
STRQEKRFXLKGLQAAAV (SEQ ID NO: 13)
ORF2, Frame -2 PDQKPXQGTSXTPWKXQXXKKRD-
FXLKDFKRLLY (SEQ ID NO: 14)

General Screening and Diagnostic Methods Using MTC sequences

Expression of each MTC nucleic acid sequence can be identified using the information provided above. In some embodiments, the MTC nucleic acids correspond to nucleic acids which include the various sequences (referenced above by SEQ ID NOs) that have been disclosed for each MTC sequence.

In its various aspects and embodiments, the invention includes providing a test cell population which includes at least one cell that is capable of expressing one or more of the sequences MTC1–51. By "capable of expressing" is meant that the nucleic acid sequence is present in an intact form in the cell and can be expressed. Expression of one, some, or all of the MTC sequences is detected, if present, and, preferably, measured. Using the sequence information provided by the database entries for the known sequences, or the sequence information provided herein for the previously unknown sequences, the expression of the MTC sequences can be detected, if present, and measured using techniques well known to one of ordinary skill in the art. For example, sequences within public sequence database entries for the MTC sequences or within the novel sequences disclosed herein can be used to construct probes for detecting MTC RNA sequences in, for example, northern blot hybridization analyses. Alternatively, the sequences can be used to construct primers for specifically amplifying the MTC sequences in, for example, amplification-based detection methods such as reverse transcription-based polymerase chain reaction (PCR).

The expression level(s) of one or more of the MTC sequences in the test cell population is then compared to expression levels of the sequences in one or more cells from a reference cell population. A reference cell population includes one or more cells for which the compared parameter or condition is known. The composition of the reference cell population will determine whether the comparison of gene expression profile indicates the presence or absence of the measured parameter or condition.

An alteration of the expression in the test cell population, as compared to the reference cell population, indicates that the measured parameter or condition in the test cell population is different than that of the reference cell. The absence of the alteration of expression in the test cell population, as compared to the reference cell population, indicates that the measured parameter or condition in the test cell population is the same as that of the reference cell. As an example, if the reference cell population contains noncancerous cells, a similar gene expression profile in the test cell population indicates that the test cells are also non-cancerous, whereas a different profile indicates that the test cells are cancerous. Likewise, if the reference cell population is made up of cancerous cells, a similar expression profile in the test cell population indicates that the test cell population also includes cancerous cells, and a different expression profile indicates that test cells are noncancerous.

In some embodiments, the test cell population is compared to multiple reference cell populations. Each of the multiple reference cell populations might differ in the known parameter. For example, a test cell population may be compared to a reference cell population containing nonmetastatic cancerous cells as well as a second reference cell population known to contain metastatic cancerous cells.

The test cell population may be known to contain or be suspected of containing a neoplasm. In some embodiments, the test cell will be included in a cell sample known to contain or suspected of containing a thyroid follicular adenoma. In other embodiments, the test cell sample will be derived from a region known to contain, or suspected of containing a metastatic papillary carcinoma. In other embodiments, the test cell population may be known to contain or be suspected of containing thyroid follicular adenomas and metastatic papillary carcinomas.

The test cell can be taken from a known or suspected tumor-containing sample, or it may be taken from a bodily fluid or biological fluid including blood, serum, urine, saliva, milk, ductal fluid, or tears. For many applications, e.g., categorizing a neoplasm, assessing the efficacy of treatment, or in diagnosing a neoplasm in a subject, cells present in bodily fluids can be examined instead of those from the primary lesion. Accordingly, the need for taking a biopsy from a known or suspected neoplasm may be obviated.

Preferably, cells in the reference cell population are derived from a tissue type that is as similar to the test cell population as possible. For example, the reference cell population may be derived from thyroid tissue. In some embodiments, the reference cell is derived from a region proximal to the region of origin of the test cell population.

The subject is preferably a mammal. For example, the mammal can be a human, non-human primate, mouse, rat, dog, cat, horse, or cow.

In some embodiments, the reference cell population is derived from a plurality of cells. The reference cell population can be a database of expression patterns from previously tested cells for which one of the assayed parameters or conditions is known.

In various embodiments, the expression of 1–51 or more of the sequences represented by MTC1–51 are measured. If desired, expression of these sequences can be measured along with other sequences whose expression is known to be altered according to one of the herein described parameters or conditions. By "altered" is meant that the expression of one or more nucleic acid sequences is either increased or decreased as compared to the expression levels in the reference cell population. Alternatively, the expression profile of the test cell population may be the same as that of the reference cell population.

The expression of the sequences disclosed herein can be measured at the RNA by any method known in the art. For example, northern blot hybridization analysis using probes that specifically recognize one or more of these MTC sequences can be used to determine gene expression. Alternatively, nucleic acid sequence expression can be measured using reverse transcription-based PCR assays that, for example, use primers specific for the differentially expressed sequences designated as MTCs: 1–51.

Expression can also be measured at the protein level by, for example, measuring the levels of polypeptides encoded by the gene products described herein. Methods for measuring the levels of polypeptides are well known in the art. For example, immunoassays can be designed based on antibodies to proteins encoded by the nucleic acid sequences.

When alterations in nucleic acid sequence expression are associated with gene amplification or deletion, sequence comparisons in the test and reference cell populations can be made by comparing the relative levels of examined nucleic acid sequences in both the test and reference cell populations.

Categorizing Thyroid Cancer Stage

In one aspect, the invention provides a method of categorizing the stage of thyroid cancer in a subject. By "categorizing thyroid cancer stage" is meant the determination of the metastatic stage of the thyroid cancer. In other words, determining whether a subject's thyroid cancer is metastatic as opposed to non-metastatic.

The method includes providing a cell from the subject and detecting the expression level of one or more of the nucleic acid sequences MTC: 1–51 in the cell.

The expression of the nucleic acid sequences is then compared to the level of expression in a reference cell population. In general, any reference cell population may be used as long as the thyroid cancer stage is known. In some embodiments, the reference cell population is made up of non-metastatic thyroid cancer cells. Test cell expression profiles that are similar to those of such a reference cell population indicate that the test cell population is also made up of non-metastatic thyroid cancer cells. Conversely, test cell expression profiles that are different from a non-metastatic thyroid cancer population are indicative of a metastatic thyroid cancer test cell population. In other embodiments, the reference cell population comprises metastatic thyroid cancer cells. In such an embodiment, a test cell expression profile similar to the reference cell would be indicative of metastatic thyroid cancer whereas a different expression pattern is indicative of nonmetastatic thyroid cancer.

If desired, relative expression levels within the test and reference cell populations can be normalized by reference to the expression level of a nucleic acid sequence that does not vary according to thyroid cancer stage in a subject.

Diagnosing a Neoplasm

The invention further provides a method for diagnosing a neoplasm, e.g., a thyroid carcinoma. A neoplasm is diagnosed by examining the expression of one or more MTC nucleic acid sequences from a test cell population that contain a suspected tumor. The population of test cells may contain the primary tumor, e.g., thyroid tissue, or, alternatively, may contain cells into which the primary tumor has disseminated, e.g., blood or lymphatic fluid.

The expression of one or more of the MTC sequences (MTCs: 1–51) is measured in the test cell and compared to the expression of the sequences in the reference cell population. The reference cell population must contain at least one cell whose neoplastic state is known. For example, the thyroid cancer stage of the reference cell population must be known. If the reference cell contains no neoplastic cells, than a similarity in MTC sequence expression between the test cell population and the reference cell populations indicates that the test cell population likewise does not contain any neoplastic cells. On the other hand, a difference in expression of MTC sequence between the test and reference cell population indicates that the test cell population contains a neoplastic cell.

Conversely, when the reference cell population contains at least one neoplastic cell, a similarity in MTC expression pattern indicates that the test cell population also includes a neoplastic cell. Alternatively, a differential expression pattern indicates that the test cell population contains non-neoplastic cells.

Assessing the Efficacy of a Treatment of a Neoplasm in a Subject

The differentially expressed MTC sequences identified herein also allow the course of treatment of a neoplasm, such as a thyroid carcinoma, to be monitored. In this method, a test cell population is provided from a subject who is undergoing treatment for a neoplasm. If desired, the test cell population can be taken from the subject at various times before, during, and after treatment. The expression of one or more of MTCs: 1–51 in the test cell population is then measured and compared to a reference cell population which includes cells whose neoplastic, i.e., thyroid carcinoma, stage is known. Preferably, the reference cells have not been exposed to the treatment.

If the reference cell population contains no neoplastic cells, a similarity in expression between the test and reference cell populations indicates that the treatment is efficacious. However, a difference in expression patterns indicates that the treatment is not efficacious.

By "efficacious" is meant that the treatment leads to a decrease in size or metastatic potential of a neoplasm in a subject, or a shift in a tumor stage to a less advanced stage. When the treatment is applied prophylactically, "efficacious" means that the treatment retards or prevents the formation of the neoplasm in a subject.

When the reference cell population contains neoplastic cells, a similar expression pattern indicates that the treatment is not efficacious, whereas a dissimilar expression pattern indicates that the treatment is efficacious.

Efficacy can be determined in association with any method for treating a particular neoplasm.

Identifying a Therapeutic Agent Individualized for Treating a Neoplasm

Genetic differences in individual subjects can result in different abilities to metabolize various drugs. An agent that is metabolized in a subject to act as an anti-neoplastic agent can manifest itself by inducing a change in gene expression pattern in the subject's cells from the pattern characteristic of the non-neoplastic state. Thus, the differentially expressed MTC sequences disclosed herein allow for a putative therapeutic or prophylactic anti-neoplastic agent to be tested in a cell population to determine if the agent is a suitable anti-neoplastic agent in the subject.

According to this method of the invention, a test cell population from the subject is exposed to a therapeutic agent. The expression of one or more MTC sequences is then measured.

In some embodiments, the test cell population contains the primary tumor, e.g. a thyroid carcinoma, or a bodily fluid, such as blood or lymph, into which the tumor cell has disseminated. In other embodiments, the agent is first mixed with a cell extract, for example, a liver cell extract, which contains enzymes that metabolize drugs into an active form. The activated form of the drug is then mixed with the test cell population so that gene expression can be measured. Preferably, the cell population is contacted ex vivo with the agent or its activated form.

By "individualized" is meant that the particular therapeutic agent selected takes the differences in genetic makeup of individuals into account by insuring that the selected agent is therapeutic in a particular subject.

Expression of the MTC sequences in the test cell population is then compared with the expression patterns in the reference cell population. Again, the reference cell population contains at least one cell whose neoplastic, i.e., thyroid carcinoma, stage is known. If the reference cell is non-cancerous, similar gene expression patterns indicate that the agent is suitable for treating the neoplasm in that subject. If the patterns are different, then the particular agent is not suitable for treating the neoplasm in a particular subject.

On the other hand, if the reference cell is cancerous, similar sequence expression patterns indicate that the agent is not suitable for the treatment of that subject. Conversely, differential MTC expression indicates that the agent is suitable for the treatment of that subject.

The test agent may be any compound or composition. In some embodiments, the agent may be a compound or composition known to be an anti-cancer agent. In other embodiments, the agent may be a compound or composition not previously known to be an anti-cancer agent.

Screening Assays for Identifying a Candidate Therapeutic Agent for Treating or Preventing a Neoplasm The differentially expressed MTC sequences disclosed herein can also be used to identify candidate therapeutic agents for treating a neoplasm, for example, a thyroid carcinoma. This method is based on the screening of a candidate therapeutic agent to determine if it converts an expression profile of MTCs: 1–51 that is characteristic of a cancerous state to a pattern indicative of a noncancerous state.

In this method, a test cell population is exposed to a test agent or a combination of test agents, either sequentially or simultaneously. The expression of one or more MTC sequence is measured. Next, the expression of the MTC sequences in the test cell population is compared to the expression level of the MTC sequences in a reference cell population that has not been exposed to the test agent.

An appropriate test agent candidate will increase the expression of MTC sequences that are downregulated in cancerous cells and/or will decrease the expression of those MTC sequences that are upregulated in cancerous cells.

In some embodiments, the reference cell population includes cancerous cells. When such a reference cell population is used, an alteration in expression of the nucleic acid sequences in the presence of the test agent from the expression pattern of the reference cell population in the absence of the reagent indicates that the agent is a candidate therapeutic agent for the treatment of a neoplasm.

The test agent or agents used in this method can be a compound(s) not previously described or can be a previously known compound that has not been shown to be an anti-neoplastic agent.

An agent that is effective in stimulating the expression of underexpressed genes, or in suppressing the expression of overexpressed genes can be further tested for its ability to prevent tumor growth. Such an agent is also potentially useful for the treatment of tumors. Further analysis of the clinical usefulness of a given compound can be performed using standard methods of evaluating toxicity and clinical effectiveness of anti-cancer agents.

Categorizing a Neoplasm

Comparison of MTC expression patterns in test cell populations and reference cell populations can be used to categorize neoplasms in a subject. For example, such a comparison can be used to categorize thyroid carcinoma in a subject.

This method includes providing a test cell population containing at least one neoplastic cell from a subject and measuring the expression of one or more MTC sequences in this test cell. The expression of the nucleic acid sequences in the test cell population is compared to the expression of the nucleic acid sequences in a reference cell population comprising at least one cell whose neoplastic state and category is known. A similarity in expression patterns indicates that the cancerous cell in the test cell population has the same neoplastic category as does the reference cell population.

By "category" is meant the neoplastic state of a given neoplasm. In other words, whether the neoplasm is metastatic or nonmetastatic. In the case of metastatic neoplasms, "categorizing a neoplasm" can mean determining the extent of the metastasis.

Assessing the Prognosis of a Subject with a Neoplasm

Also provided is a method of assessing the prognosis of a subject having a neoplasm, such as a thyroid carcinoma, by comparing the expression of one or more MTC sequences in a test cell population, which contains at least one cancerous cell, to the expression of the sequences in a reference cell population. By comparing the gene expression profiles of one or more MTC sequences, the prognosis of the subject can be assessed.

In alternative embodiments, the reference cell population includes primarily noncancerous or cancerous cells. When the reference cell contains primarily noncancerous cells, an increase in the expression of an MTC sequence that is overexpressed in the metastatic cancer state, or a decrease in the expression of an MTC sequence that is underexpressed in the metastatic state, suggests a less favorable prognosis. Specifically, an increase in any one or more of MTCs: 1, 3, 5–16, 18–23, 25–27, 29–31, 33–35, 37, 39, 41–42, 44–45, 48 or 50, or a decrease in any one or more of MTCs: 2, 4, 17, 24, 28, 32, 36, 38, 40, 43, or 46, compared to a noncancerous reference cell is indicative of a less favorable prognosis.

When the reference cell population contains primarily cancerous cells, a decrease in the expression of a MTC sequence that is overexpressed in the metastatic state, or an increase in the expression of a MTC sequence that is underexpressed in the metastatic state, suggests a favorable prognosis. Thus, a decrease in the expression of any one or more of MTCs: 1, 3, 5–16, 18–23, 25–27, 29–31, 33–35, 37, 39, 41–42, 44–45, 48 or 50, or an increase in the expression of any one or more of MTCs: 2, 4, 17, 24, 28, 32, 36, 38, 40, 43, or 46, compared to a cancerous reference cell population is indicative of a favorable prognosis for the subject.

Treating Metastatic Cancer

Also provided is a method of treating metastatic cancer, for example, metastatic thyroid carcinomas, in a patent suffering from or at risk for developing metastatic cancer. By "at risk for developing" is meant that the subject's prognosis is less favorable and that the subject has an increased likelihood of developing metastatic cancer. This method involves the administration of an agent that modulates the expression of one or more MTC sequences to a subject in need of treatment. Administration can be prophylactic or therapeutic.

In one embodiment, this method comprises administering to a subject, an agent that increases the expression of one or more nucleic acid sequences selected from the group consisting of MTCs: 2, 4, 17, 24, 28, 32, 36, 38, 40, 43, and 46. These MTC sequences are underexpressed in the metastatic state as compared to the nonmetastatic state. The subject is treated with an effective amount of a compound that increases the amount the underexpressed nucleic acid sequences in the subject. Administration can be systemic or local, e.g., in the immediate vicinity of the subject's cancerous cells. This agent could be, for example, the polypeptide product of the underexpressed gene or a biologically active fragment thereof, a nucleic acid encoding the underexpressed gene and having expression control elements permitting expression in the carcinoma cells, or an agent which increases the endogenous level of expression of the gene.

In another embodiment, this method comprises administering an agent that decreases the expression of one or more nucleic acid sequences selected from the group consisting of MTCs: 1, 3, 5–16, 18–23, 25–27, 29–31, 33–35, 37, 39, 41–42, 44–45, 48, and 50. These MTC sequences are overexpressed in the metastatic cancerous state. Again, the subject is treated with an effective amount of a compound that decreases the amount of the overexpressed nucleic acid sequences in the subject. As discussed above, administration can be systemic or local. Expression can be inhibited in any of several ways known in the art. For example, expression can be inhibited by administering to the subject a nucleic acid that inhibits, or antagonizes, the expression of the overexpressed gene or genes. In one embodiment, an antisense oligonucleotide can be administered to disrupt expression of the endogenous gene or genes.

In an alternative embodiment, the patient may be treated with one or more agents which decrease the expression of those MTC sequences that are overexpressed in the metastatic state alone or in combination with one or more agents which increase the expression of those MTC sequences that are underexpressed in the metastatic state.

Administration of a prophylactic agent can occur prior to the manifestation of symptoms characteristic of aberrant gene expression, such that a disease or disorder is prevented or, alternatively, delayed in its progression. Depending on the type of aberrant expression detected, the agent can be used for treating the subject. The appropriate agent can be determined based on screening assays described herein. Determination of an effective amount of a compound is within the ordinary skill of one in this art.

In some embodiments, a subject, e.g., a human, is treated with genes encoding secreted or membrane bound polypeptides, or with the encoded polypeptide. These genes include, e.g., alpha-1-antitrypsin ,Neuropilin, NET-1 , Lipocortin II integrin alpha-3 Type IV collagenase Antileukoprotease Periplakin Clusterin DAP12. These secreted or membrane bound proteins are up-regulated in metastatic thyroid cancers. Accordingly, they are also desirable candidates for antibody screening and antibody-binding therapy.

In other embodiments, the patient is treated with a gene encoding a membrane or secreted protein that is down-regulated in metastatic thyroid cancer, or its encoded polypeptide. These genes include, e.g., RIG-E, PRO302. These secreted or membrane protein that can be easily delivered back to the affected patients as recombinant soluble proteins for the treatment of metastatic thyroid cancer.

Pharmaceutical Compositions for Treating Neoplasms

In another aspect, the invention includes pharmaceutical or therapeutic compositions containing one or more therapeutic compounds described herein. Pharmaceutical formulations may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All such pharmacy methods include the steps of bringing into association the active compound with liquid carriers or finely divided solid carriers or both as needed and then, if necessary, shaping the product into the desired formulation.

Pharmaceutical formulations suitable for oral administration may conveniently be presented as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia. For intra-nasal administration the compounds of the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation the compounds are conveniently delivered from an insufflator, nebulizer, pressurized packs or other convenient means of delivering an aerosol spray. Pressurized packs may comprise a suitable propellant such as dichlorodifluoromethane, trichlorofluoromethane, dichiorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

When desired, the above-described formulations, adapted to give sustained release of the active ingredient, may be employed. The pharmaceutical compositions may also contain other active ingredients such as antimicrobial agents, immunosuppressants or preservatives.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited below, or an appropriate fraction thereof, of the active ingredient.

For each of the aforementioned conditions, the compositions may be administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The pharmaceutical composition preferably is administered orally or by injection (intravenous or subcutaneous), and the precise amount administered to a subject will be the responsibility of the attendant physician. However, the dose employed will depend upon a number of factors, including the age and sex of the subject, the precise disorder being treated, and its severity. Also the route of administration may vary depending upon the condition and its severity. Determination of the proper dose and route of administration is within the ordinary skill of those familiar with this art.

A nucleic acid molecule of the present invention, e.g., a nucleic acid molecule having the nucleotide sequence of any of MTCS:48–51, or a complement of any of these nucleotide sequences, can be isolated using standard molecular biology techniques and the sequence information provided herein. Using all or a portion of these nucleic acid sequences as a hybridization probe, MTC nucleic acid sequences can be isolated using standard hybridization and cloning techniques (e.g., as described in Sambrook et al., eds., *MOLECULAR CLONING: A LABORATORY MANUAL* $2^{nd}$ Ed., Cold Spring Harbor Laboratory Press, Cold Spring Harbor, N.Y., 1989; and Ausubel, et al., eds., *CURRENT PROTOCOLS IN MOLECULAR BIOLOGY*, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to MTC nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having at least about 10 nt and as many as 50 nt, preferably about 15 nt to 30 nt. They may be chemically synthesized and may be used as probes.

In another embodiment, an isolated nucleic acid molecule of the invention comprises a nucleic acid molecule that is a complement of the nucleotide sequence shown in MTCs: 48–51. In another embodiment, an isolated nucleic acid molecule of the invention comprises a nucleic acid molecule that is a complement of the nucleotide sequence shown in any of these sequences, or a portion of any of these nucleotide sequences. A nucleic acid molecule that is complementary to the nucleotide sequence shown in MTCs:48–51 is one that is sufficiently complementary to the nucleotide sequence shown, such that it can hydrogen bond with little or no mismatches to the nucleotide sequences shown, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of MTCs:48–51 e.g., a fragment that can be used as a probe or primer or a fragment encoding a biologically active portion of MTC. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences. that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 45%, 50%, 70%, 80%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g Ausubel, et al., *CURRENT PROTOCOLS IN MOLECULAR BIOLOGY*, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489, which in incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a MTC polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a MTC polypeptide of species other than humans, including, but not limited to, mammals, and thus can include, e.g, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding a human MTC protein. Homologous nucleic acid sequences include those nucleic acid sequences that encode conservative amino acid substitutions (see below) in a MTC polypeptide, as well as a polypeptide having a MTC activity. A homologous amino acid sequence does not encode the amino acid sequence of a human MTC polypeptide.

The nucleotide sequence determined from the cloning of human MTC genes allows for the generation of probes and primers designed for use in identifying and/or cloning MTC homologues in other cell types, e.g., from other tissues, as well as MTC homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of a nucleic acid comprising a MTC sequence, or an anti-sense strand nucleotide sequence of a nucleic acid comprising a MTC sequence, or of a naturally occurring mutant of these sequences.

Probes based on human MTC nucleotide sequences can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a MTC protein, such as by measuring a level of a MTC-encoding nucleic acid in a sample of cells from a subject e.g., detecting MTC mRNA levels or determining whether a genomic MTC gene has been mutated or deleted. "A polypeptide having a biologically active portion of MTC" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of MTC" can be prepared by isolating a portion of MTCs:48–51, that encodes a polypeptide having a MTC biological activity, expressing the encoded portion of MTC protein (e.g., by recombinant expression in vitro) and assessing the activity of the encoded portion of MTC. For example, a nucleic acid fragment encoding a biologically active portion of a MTC polypeptide can optionally include an ATP-binding domain. In another embodiment, a nucleic acid fragment encoding a biologically active portion of MTC includes one or more regions.

MTC Variants

The invention further encompasses nucleic acid molecules that differ from the disclosed or referenced MTC nucleotide sequences due to degeneracy of the genetic code. These nucleic acids thus encode the same MTC protein as that encoded by nucleotide sequence comprising a MTC nucleic acid as shown in, e.g., MTC48–51.

In addition to the MTC nucleotide sequences disclosed for MTCs:48–51, it will be appreciated by those skilled in the art that DNA sequence polymorphisms that lead to changes in the amino acid sequences of a MTC polypeptide may exist within a population (e.g., the human population). Such genetic polymorphism in the MTC gene may exist among individuals within a population due to natural allelic variation. As used herein, the terms "gene" and "recombinant gene" refer to nucleic acid molecules comprising an open reading frame encoding a MTC protein, preferably a mammalian MTC protein. Such natural allelic variations can typically result in 1–5% variance in the nucleotide sequence of the MTC gene. Any and all such nucleotide variations and resulting amino acid polymorphisms in MTC that are the result of natural allelic variation and that do not alter the functional activity of MTC are intended to be within the scope of the invention.

Moreover, nucleic acid molecules encoding MTC proteins from other species, and thus that have a nucleotide sequence that differs from the human sequence of MTC48–51, are intended to be within the scope of the invention. Nucleic acid molecules corresponding to natural allelic variants and homologues of the MTC DNAs of the invention can be isolated based on their homology to the human MTC nucleic acids disclosed herein using the human cDNAs, or a portion thereof, as a hybridization probe according to standard hybridization techniques under stringent hybridization conditions. For example, a soluble human MTC DNA can be isolated based on its homology to human membrane-bound MTC. Likewise, a membrane-bound human MTC DNA can be isolated based on its homology to soluble human MTC.

Accordingly, in another embodiment, an isolated nucleic acid molecule of the invention is at least 6 nucleotides in length and hybridizes under stringent conditions to the nucleic acid molecule comprising the nucleotide sequence of MTCs:48–51. In another embodiment, the nucleic acid is at least 10, 25, 50, 100, 250 or 500 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding MTC proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in *CURRENT PROTOCOLS IN MOLECULAR BIOLOGY*, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of MTCs:48–51 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of MTCs:48–51 or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g, Ausubel et al. (eds.), 1993, CURRENT PROTOCOLS IN MOLECULAR BIOLOGY, John Wiley & Sons, New York, and Kriegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of MTCs:48–5 or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al (eds.), 1993, CURRENT PROTOCOLS IN MOLECULAR BIOLOGY, John Wiley & Sons, New York, and Kriegler, 1990, GENE TRANSFER AND EXPRESSION, A LABORATORY MANUAL, Stockton Press, NY; Shilo et al., 1981, Proc Natl Acad Sci USA 78: 6789–6792.

Conservative Mutations

In addition to naturally-occurring allelic variants of the MTC sequence that may exist in the population, the skilled artisan will further appreciate that changes can be introduced into an MTC nucleic acid or directly into an MTC polypeptide sequence without altering the functional ability of the MTC protein. In some embodiments, the nucleotide sequence of MTCs:48–51 will be altered, thereby leading to changes in the amino acid sequence of the encoded MTC protein. For example, nucleotide substitutions that result in amino acid substitutions at various "non-essential" amino acid residues can be made in the sequence of MTCs:48–51. A "non-essential" amino acid residue is a residue that can be altered from the wild-type sequence of MTC without altering the biological activity, whereas an "essential" amino acid residue is required for biological activity. For example, amino acid residues that are conserved among the MTC proteins of the present invention, are predicted to be particularly unamenable to alteration.

In addition, amino acid residues that are conserved among family members of the MTC proteins of the present invention, are also predicted to be particularly unamenable to alteration. As such, these conserved domains are not likely to be amenable to mutation. Other amino acid residues, however, (e.g., those that are not conserved or only semi-conserved among members of the MTC proteins) may not be essential for activity and thus are likely to be amenable to alteration.

Another aspect of the invention pertains to nucleic acid molecules encoding MTC proteins that contain changes in amino acid residues that are not essential for activity. Such MTC proteins differ in amino acid sequence from the amino acid sequences of polypeptides encoded by nucleic acids containing MTCs:48–51, yet retain biological activity. In one embodiment, the isolated nucleic acid molecule comprises a nucleotide sequence encoding a protein, wherein the protein comprises an amino acid sequence at least about 45% homologous, more preferably 60%, and still more preferably at least about 70%, 80%, 90%, 95%, 98%, and most preferably at least about 99% homologous to the amino acid sequence of the amino acid sequences of polypeptides encoded by nucleic acids comprising MTCs:48–51.

An isolated nucleic acid molecule encoding a MTC protein homologous to can be created by introducing one or more nucleotide substitutions, additions or deletions into the nucleotide sequence of a nucleic acid comprising MTCs:48–51, such that one or more amino acid substitutions, additions or deletions are introduced into the encoded protein.

Mutations can be introduced into a nucleic acid comprising MTCs:48–51 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in MTC is replaced with another amino acid residue from the same side chain family. Alternatively, in another embodiment, mutations can be introduced randomly along all or part of a MTC coding sequence, such as by saturation mutagenesis, and the resultant mutants can be screened for MTC biological activity to identify mutants that retain activity. Following mutagenesis of the nucleic acid, the encoded protein can be expressed by any recombinant technology known in the art and the activity of the protein can be determined.

In one embodiment, a mutant MTC protein can be assayed for (1) the ability to form protein:protein interactions with other MTC proteins, other cell-surface proteins, or biologically active portions thereof, (2) complex formation between a mutant MTC protein and a MTC ligand; (3) the ability of a mutant MTC protein to bind to an intracellular target protein or biologically active portion thereof; (e.g., avidin proteins); (4) the ability to bind ATP; or (5) the ability to specifically bind a MTC protein antibody.

In other specific embodiments, the nucleic acid is RNA or DNA.

Antisense

Another aspect of the invention pertains to isolated antisense nucleic acid molecules that are hybridizable to or complementary to the nucleic acid molecule comprising the nucleotide sequence of a MTC sequence or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire MTC coding strand, or to only a portion thereof. Nucleic acid molecules encoding fragments, homologs, derivatives and analogs of a MTC protein, or antisense nucleic acids complementary to a nucleic acid comprising a MTC nucleic acid sequence are additionally provided.

In one embodiment, an antisense nucleic acid molecule is antisense to a "coding region" of the coding strand of a nucleotide sequence encoding MTC. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding MTC. The term "noncoding region" refers to 5' and 3' sequences which flank the coding region that are not translated into amino acids (i.e., also referred to as 5' and 3' untranslated regions).

Given the coding strand sequences encoding MTC disclosed herein, antisense nucleic acids of the invention can be designed according to the rules of Watson and Crick or Hoogsteen base pairing. The antisense nucleic acid molecule can be complementary to the entire coding region of MTC mRNA, but more preferably is an oligonucleotide that is antisense to only a portion of the coding or noncoding region of MTC mRNA. For example, the antisense oligonucleotide can be complementary to the region surrounding the translation start site of MTC mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a MTC protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave MTC mRNA transcripts to thereby inhibit translation of MTC mRNA. A ribozyme having specificity for a MTC-encoding nucleic acid can be designed based upon the nucleotide sequence of a MTC DNA disclosed herein. For example, a derivative of a Tetrahymena L-19 IVS RNA can be constructed in which the nucleotide sequence of the active site is complementary to the nucleotide sequence to be cleaved in a MTC-encoding mRNA. See, e.g., Cech et al. U.S. Pat. No. 4,987,071; and Cech et al. U.S. Pat. No. 5,116,742. Alternatively, MTC mRNA can be used to select a catalytic RNA having a specific ribonuclease activity from a pool of RNA molecules. See, e.g., Bartel et al., (1993) *Science* 261:1411–1418.

Alternatively, MTC gene expression can be inhibited by targeting nucleotide sequences complementary to the regulatory region of a MTC nucleic acid (e.g., the MTC promoter and/or enhancers) to form triple helical structures that prevent transcription of the MTC gene in target cells. See generally, Helene. (1991) *Anticancer Drug Des*. 6:569–84; Helene. et al. (1992) *Ann. N.Y. Acad. Sci*. 660:27–36; and Maher (1992) *Bioassays* 14: 807–15.

In various embodiments, the nucleic acids of MTC can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4:5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of MTC can be used in therapeutic and diagnostic applications. For example, PNAs can be used as antisense or antigene agents for sequence-specific modulation of gene expression by, e.g., inducing transcription or translation arrest or inhibiting replication. PNAs of MTC can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of MTC can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of MTC can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (.1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. W088/09810) or the blood-brain barrier (see, e.g., PCT Publication No. W089/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

MTC Polypeptides

One aspect of the invention pertains to isolated MTC polypeptides or proteins (these terms are used interchangeably herein), and biologically active portions thereof, or derivatives, fragments, analogs or homologs thereof. Also provided are polypeptide fragments suitable for use as immunogens to raise anti-MTC antibodies. In one embodiment, native MTC proteins can be isolated from cells or tissue sources by an appropriate purification scheme using standard protein purification techniques. In another embodiment, MTC proteins are produced by recombinant DNA techniques. Alternative to recombinant expression, a MTC protein or polypeptide can be synthesized chemically using standard peptide synthesis techniques.

An "isolated" or "purified" protein or biologically active portion thereof is substantially free of cellular material or other contaminating proteins from the cell or tissue source from. which the MTC protein is derived, or substantially free from chemical precursors or other chemicals when chemically synthesized. The language "substantially free of cellular material" includes preparations of MTC protein in which the protein is separated from cellular components of the cells from which it is isolated or recombinantly produced. In one embodiment, the language "substantially free of cellular material" includes preparations of MTC protein having less than about 30% (by dry weight) of non-MTC protein (also referred to herein as a "contaminating protein"), more preferably less than about 20% of non-MTC protein, still more preferably less than about 10% of non-MTC protein, and most preferably less than about 5% non-MTC protein. When the MTC protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of MTC protein in which the protein is separated from chemical precursors or other chemicals that are involved in the synthesis of the protein. In one embodiment, the language "substantially free of chemical precursors or other chemicals" includes preparations of MTC protein having less than about 30% (by dry weight) of chemical precursors or non-MTC chemicals, more preferably less than about 20% chemical precursors or non-MTC chemicals, still more preferably less than about 10% chemical precursors or non-MTC chemicals, and most preferably less than about 5% chemical precursors or non-MTC chemicals.

Biologically active portions of a MTC protein include peptides comprising amino acid sequences sufficiently homologous to or derived from the amino acid sequence of the MTC protein, e.g., the amino acid sequence encoded by a nucleic acid comprising MTC1–20 that include fewer amino acids than the full length MTC proteins, and exhibit at least one activity of a MTC protein. Typically, biologically active portions comprise a domain or motif with at least one activity of the MTC protein. A biologically active portion of a MTC protein can be a polypeptide which is, for example, 10, 25, 50, 100 or more amino acids in length.

A biologically active portion of a MTC protein of the present invention may contain at least one of the above-identified domains conserved between the MTC proteins. An alternative biologically active portion of a MTC protein may contain at least two of the above-identified domains. Another biologically active portion of a MTC protein may contain at least three of the above-identified domains. Yet another biologically active portion of a MTC protein of the present invention may contain at least four of the above-identified domains.

Moreover, other biologically active portions, in which other regions of the protein are deleted, can be prepared by recombinant techniques and evaluated for one or more of the functional activities of a native MTC protein.

In some embodiments, the MTC protein is substantially homologous to one of these MTC proteins and retains its the functional activity, yet differs in amino acid sequence due to natural allelic variation or mutagenesis, as described in detail below.

In specific embodiments, the invention includes an isolated polypeptide comprising an amino acid sequence that is 80% or more identical to the sequence of a polypeptide whose expression is modulated in a mammal to which PPARγ ligand is administered.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of a DNA sequence comprising MTCS: 48–51.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or 1, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides MTC chimeric or fusion proteins. As used herein, an MTC "chimeric protein" or "fusion protein" comprises an MTC polypeptide operatively linked to a non-MTC polypeptide. A "MTC polypeptide" refers to a polypeptide having an amino acid sequence corresponding to MTC, whereas a "non-MTC polypeptide" refers to a polypeptide having an amino acid sequence corresponding to a protein that is not substantially homologous to the MTC protein, e.g., a protein that is different from the MTC protein and that is derived from the same or a different organism. Within an MTC fusion protein the MTC polypeptide can correspond to all or a portion of an MTC protein. In one embodiment, an MTC fusion protein comprises at least one biologically active portion of an MTC protein. In another embodiment, an MTC fusion protein comprises at least two biologically active portions of an MTC protein. In yet another embodiment, an MTC fusion protein comprises at least three biologically active portions of an MTC protein. Within the fusion protein, the term "operatively linked" is intended to indicate that the MTC polypeptide and the non-MTC polypeptide are fused in-frame to each other. The non-MTC polypeptide can be fused to the N-terminus or C-terminus of the MTC polypeptide.

For example, in one embodiment an MTC fusion protein comprises an MTC domain operably linked to the extracellular domain of a second protein. Such fusion proteins can be further utilized in screening assays for compounds which modulate MTC activity (such assays are described in detail below).

In yet another embodiment, the fusion protein is a GST-MTC fusion protein in which the MTC sequences are fused to the C-terminus of the GST (i.e., glutathione S-transferase) sequences. Such fusion proteins can facilitate the purification of recombinant MTC.

In another embodiment, the fusion protein is an MTC protein containing a heterologous signal sequence at its N-terminus. For example, a native MTC signal sequence can be removed and replaced with a signal sequence from another protein. In certain host cells (e.g., mammalian host cells), expression and/or secretion of MTC can be increased through use of a heterologous signal sequence.

In yet another embodiment, the fusion protein is an MTC-immunoglobulin fusion protein in which the MTC sequences comprising one or more domains are fused to sequences derived from a member of the immunoglobulin protein family. The MTC-immunoglobulin fusion proteins of the invention can be incorporated into pharmaceutical compositions and administered to a subject to inhibit an interaction between a MTC ligand and a MTC protein on the surface of a cell, to thereby suppress MTC-mediated signal transduction in vivo. The MTC-immunoglobulin fusion proteins can be used to affect the bioavailability of an MTC cognate ligand. Inhibition of the MTC ligand/MTC interaction may be useful therapeutically for both the treatments of proliferative and differentiative disorders, as well as modulating (e.g. promoting or inhibiting) cell survival. Moreover, the MTC-immunoglobulin fusion proteins of the invention can be used as immunogens to produce anti-MTC antibodies in a subject, to purify MTC ligands, and in screening assays to identify molecules that inhibit the interaction of MTC with a MTC ligand.

An MTC chimeric or fusion protein of the invention can be produced by standard recombinant DNA techniques. For example, DNA fragments coding for the different polypeptide sequences are ligated together in-frame in accordance with conventional techniques, e.g, by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *CURRENT*

PROTOCOLS IN MOLECULAR BIOLOGY, John Wiley & Sons, 1992). Moreover, many expression vectors are commercially available that already encode a fusion moiety (e.g., a GST polypeptide). An MTC-encoding nucleic acid can be cloned into such an expression vector such that the fusion moiety is linked in-frame to the MTC protein.

MTC Agonists and Antagonists

The present invention also pertains to variants of the MTC proteins, e.g., MTC1–51, that function as either MTC agonists (mimetics) or as MTC antagonists. Variants of the MTC protein can be generated by mutagenesis, e.g., discrete point mutation or truncation of the MTC protein. An agonist of the MTC protein can retain substantially the same, or a subset of, the biological activities of the naturally occurring form of the MTC protein. An antagonist of the MTC protein can inhibit one or more of the activities of the naturally occurring form of the MTC protein by, for example, competitively binding to a downstream or upstream member of a cellular signaling cascade which includes the MTC protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the MTC proteins.

Variants of the MTC protein that function as either MTC agonists (mimetics) or as MTC antagonists can be identified by screening combinatorial libraries of mutants, e.g., truncation mutants, of the MTC protein for MTC protein agonist or antagonist activity. In one embodiment, a variegated library of MTC variants is generated by combinatorial mutagenesis at the nucleic acid level and is encoded by a variegated gene library. A variegated library of MTC variants can be produced by, for example, enzymatically ligating a mixture of synthetic oligonucleotides into gene sequences such that a degenerate set of potential MTC sequences is expressible as individual polypeptides, or alternatively, as a set of larger fusion proteins (e.g., for phage display) containing the set of MTC sequences therein. There are a variety of methods which can be used to produce libraries of potential MTC variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential MTC sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

In one embodiment, proteins having enzymatic activities are used for small molecule screening and small molecule drug therapy. These proteins include, e.g., the DUSP6 dual specificity MAP kinase phosphatase, ras GTPase-activating-like protein (IQGAP1), Ca2-activated neutral protease large subunit calpain, Cathepsin E, 5-lipoxygenase, Spermidine/spermine N1-acetyltransferase (SSAT), and STE20-like protein kinase 3 (STK3) protein phosphatase-1 gamma 1.

Polypeptide libraries

In addition, libraries of fragments of the MTC protein coding sequence can be used to generate a variegated population of MTC fragments for screening and subsequent selection of variants of an MTC protein. In one embodiment, a library of coding sequence fragments can be generated by treating a double stranded PCR fragment of a MTC coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the MTC protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of MTC proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify MTC variants (Arkin and Yourvan (1992) *PNAS* 89:7811–7815; Delgrave et al. (1993) Protein Engineering 6:327–331).

Anti-MTC Antibodies

An isolated MTC protein, or a portion or fragment thereof, can be used as an immunogen to generate antibodies that bind MTC using standard techniques for polyclonal and monoclonal antibody preparation. The full-length MTC protein can be used or, alternatively, the invention provides antigenic peptide fragments of MTC for use as immunogens. The antigenic peptide of MTC comprises at least 8 amino acid residues of the amino acid sequence encoded by a nucleic acid comprising the nucleic acid sequence shown in MTC:1–51, e.g., MTC48–51 and encompasses an epitope of MTC such that an antibody raised against the peptide forms a specific immune complex with MTC. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of MTC that are located on the surface of the protein, e.g., hydrophilic regions. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824–3828; Kyte and Doolittle 1982, J. Mol. Biol. 157: 105–142, each incorporated herein by reference in their entirety.

MTC polypeptides or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen. Such antibodies include, but are not limited to, polyclonal, monoclonal, chimeric, single chain, $F_{ab}$ and $F_{(ab')2}$ fragments, and an Fab expression library. Various procedures known within the art may be used for the production of polyclonal or monoclonal antibodies to an MTC protein sequence, or derivatives, fragments, analogs or homologs thereof. Some of these proteins are discussed below.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed MTC protein or a chemically synthesized MTC polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory agents. If desired, the antibody molecules directed against MTC can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of MTC. A monoclonal antibody composition thus typically displays a single binding affinity for a particular MTC protein with which it immunoreacts. For preparation of monoclonal antibodies directed towards a particular MTC protein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 *Nature* 256: 495–497); the trioma technique; the human B-cell hybridoma technique (see Kozbor, et al., 1983 *Immunol Today* 4: 72) and the EBV hybridoma technique to produce human monoclonal antibodies (see Cole, et al., 1985 In: *MONOCLONAL ANTIBODIES AND CANCER THERAPY*, Alan R. Liss, Inc., pp. 77–96). Human monoclonal antibodies may be utilized in the practice of the present invention and may be produced by using human hybridomas (see Cote, et al., 1983. *Proc Natl Acad Sci USA* 80: 2026–2030) or by transforming human B-cells with Epstein Barr Virus in vitro (see Cole, et al., 1985 In: *MONOCLONAL ANTIBODIES AND CANCER THERAPY*, Alan R. Liss, Inc., pp. 77–96).

According to the invention, techniques can be adapted for the production of single-chain antibodies specific to a MTC protein (see e.g., U.S. Pat. No. 4,946,778). In addition, methods can be adapted for the construction of Fab expression libraries (see e.g., Huse, et al., 1989 *Science 246: 1275–1281*) to allow rapid and effective identification of monoclonal $F_{ab}$ fragments with the desired specificity for a MTC protein or derivatives, fragments, analogs or homologs thereof. Non-human antibodies can be "humanized" by techniques well known in the art. See e.g., U.S. Pat. No. 5,225,539. Antibody fragments that contain the idiotypes to a MTC protein may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-MTC antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al.(1988) *Science* 240:1041–1043; Liu et al. (1987) *PNAS* 84:3439–3443; Liu et al. (1987) *J Immunol.* 139:3521–3526; Sun et al. (1987) *PNAS* 84:214–218; Nishimura et al. (1987) *Cancer Res* 47:999–1005; Wood et al. (1985) *Nature* 314:446–449; Shaw et al. (1988)*J Natl Cancer Inst.* 80:1553–1559); Morrison(1 985) *Science* 229:1202–1207; Oi et al. (1986) *BioTechniques* 4:214; U.S. Pat. No. 5,225,539; Jones et al. (1986) *Nature* 321:552–525; Verhoeyan et al. (1988) *Science* 239:1534; and Beidler et al. (1988) *J Immunol* 141:4053–4060.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a MTC protein is facilitated by generation of hybridomas that bind to the fragment of a MTC protein possessing such a domain. Antibodies that are specific for one or more domains within a MTC protein, e.g., domains spanning the above-identified conserved regions of MTC family proteins, or derivatives, fragments, analogs or homologs thereof, are also provided herein.

Anti-MTC antibodies may be used in methods known within the art relating to the localization and/or quantitation of a MTC protein (e.g., for use in measuring levels of the MTC protein within appropriate physiological samples, for use in diagnostic methods, for use in imaging the protein, and the like). In a given embodiment, antibodies for MTC proteins, or derivatives, fragments, analogs or homologs thereof, that contain the antibody derived binding domain, are utilized as pharmacologically-active compounds [hereinafter "Therapeutics" ].

An anti-MTC antibody (e.g., monoclonal antibody) can be used to isolate MTC by standard techniques, such as affinity chromatography or immunoprecipitation. An anti-MTC antibody can facilitate the purification of natural MTC from cells and of recombinantly produced MTC expressed in host cells. Moreover, an anti-MTC antibody can be used to detect MTC protein (e.g., in a cellular lysate or cell supernatant) in order to evaluate the abundance and pattern of expression of the MTC protein. Anti-MTC antibodies can be used diagnostically to monitor protein levels in tissue as part of a clinical testing procedure, e.g., to, for example, determine the efficacy of a given treatment regimen. Detection can be facilitated by coupling (i. e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, oracetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or 3H MTC recombinant Expression Vectors and Host Cells Another aspect of the invention pertains to vectors, preferably expression vectors, containing a nucleic acid encoding MTC protein, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *GENE EXPRESSION TECHNOLOGY: METHODS IN ENZYMOLOGY* 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., MTC proteins, mutant forms of MTC, fusion proteins, etc.).

Recombinant expression vectors of the invention can be designed for expression of MTC in prokaryotic or eukaryotic cells. For example, MTC can be expressed in bacterial cells such as *E. coli*, insect cells (using baculovirus expression vectors) yeast cells or mammalian cells. Suitable host cells are discussed further in Goeddel, *GENE EXPRESSION TECHNOLOGY: METHODS IN ENZYMOLOGY* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., *GENE EXPRESSION TECHNOLOGY: METHODS IN ENZYMOLOGY* 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, Gottesman, *GENE EXPRESSION TECHNOLOGY: METHODS IN ENZYMOLOGY* 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:21111–2118). Such alteration of nucleic acid sequences of the invention can be carried out by standard DNA synthesis techniques.

In another embodiment, the MTC expression vector is a yeast expression vector. Examples of vectors for expression in yeast *S. cerevisiae* include pYepSec 1 (Baldari, et al., (1987) *EMBO J* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, MTC can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J 6: 187–195*). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., *MOLECULAR CLONING: A LABORATORY MANUAL*. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985)*Science* 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374–379) and the α-fetoprotein promoter (Campes and Tilghman (1989) *Genes Dev* 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to MTC mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, MTC protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*MOLECULAR CLONING: A LABORATORY MANUAL*. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding MTC or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an MTC protein. Accordingly, the invention further provides methods for producing MTC protein using the host cells of the invention. In one embodiment, the method comprises culturing the host cell of invention (into which a recombinant expression vector encoding MTC has been introduced) in a suitable medium such that MTC protein is produced: In another embodiment, the method further comprises isolating MTC from the medium or the host cell.

Kits, Arrays, and Pluralities

The invention provides for a kit comprising one or more reagents for detecting two or more nucleic acid sequences selected from the group consisting of MTCs: 1–51. In various embodiments, the expression of 2, 3, 4, 5, 6, 7, 8, 9, 10, 15, 20, 25, 30, 35, 40, 45, 50, or 51 or more of the sequences represented by MTCs: 1–51 are measured. The kit can identify the enumerated nucleic acids by, e.g., having homologous nucleic acid sequences, such as oligonucleotide sequences, complementary to a portion of the recited nucleic acids, or antibodies to proteins encoded by the genes.

The invention also includes an array of probe nucleic acids. These probe nucleic acid sequences detect two or more nucleic acid sequences selected from the group consisting of MTCs: 1–51. In various embodiments, the expression of 2, 3, 4, 5, 6, 7, 8, 9, 10, 15, 20, 25, 30, 35, 40, 45, 50, or 51 or more of the sequences represented by MTCs: 1–51 are identified.

The probe nucleic acids in the array can detect the enumerated nucleic acids by, e.g., having homologous nucleic acid sequences, such as oligonucleotide sequences, complementary to a portion of the recited nucleic acids. The substrate array can be on, e.g., a solid substrate, e.g., a "chip", as described in U.S. Pat. No. 5,744,305.

The invention also includes an isolated plurality of nucleic acid sequences. The plurality typically includes two or more of the nucleic acid sequences represented by MTCs: 1–51. In various embodiments, the plurality includes 2, 3, 4, 5, 6, 7, 8, 9, 10, 15, 20, 25, 30, 35, 40, 45, 50, or 51 or more of the sequences represented by MTCs: 1–51.

An "isolated" nucleic acid molecule is one that is separated from other nucleic acid molecules, which are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, and "isolated" nucleic acid is free of sequences which naturally flank the nucleic acid (i.e., sequences located at the 5' and 3' ends of the nucleic acid) in the genomic DNA of the organism from which the nucleic acid is derived. In various embodiments, the isolated nucleic acid molecule can contain less than about 50 kb, 25 kb, 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or cultural medium when produced by recombinant techniques, or of chemical precursors or other chemicals when chemically synthesized.

Compositions Including Novel Nucleic Acids Differentially Expressed in Metastatic and Nonmetastatic Cancer The invention also provides compositions of novel nucleic acid sequences that are differentially expressed in metastatic and nonmetastic thyroid cancer. Thus, the invention includes isolated nucleic acid molecules comprising a nucleotide sequence selected from the group consisting of MTCs:48–51, or fragments thereof.

Single Nucleotide Polymorphisms in MTCX Genes

Also provided in the invention are nucleic acids corresponding to polymorphisms in MTCX genes. MTCX Single Nucleotide Polymorphisms ("SNPs") according to the invention include those shown in Table 2.

TABLE 2

| Confirmed Gene | MTCX | CSNP's found in 5'/3' UTR's | SNP's found in coding region that do not change amino acids | cSNP's found in coding region that change amino acids |
|---|---|---|---|---|
| KIAA1131 | MTC32 | G4944T; T4947C; A5060G; T5081C | | |
| Periplakin | MTC20 | T5738C; C6107A | A3521G; C4118T | G1777A (Arg—Gln); C4728G (Gln—Glu) |
| Mitochondrial proteolipid | MTC33 | A264G; G283A | | A85G (Ile—Val); T158C (Phe—Ser) |
| Phosphatase-1 gamma 1 | MTC18 | A1680G; A1951G | | |
| Prostaglandin transporter hPGT | MTC38 | A3163G; A3247G | | A1269G (Thr—Ala) |

TABLE 2-continued

| Confirmed Gene | MTCX | CSNP's found in 5'/3' UTR's | SNP's found in coding region that do not change amino acids | cSNP's found in coding region that change amino acids |
|---|---|---|---|---|
| E-cadherin | MTC4 | | C2076T | |
| Kinectin | MTC37 | T42G | | |
| Staf50 | MTC41 | C2290T; T2458C | | |
| Proteasome subunit HC5 | MTC21 | | | G534C (Gln—His) |
| Proteasome activator hPA28 subunit beta | | | | C331A (Pro—His); G374T (Val—Phe) |
| STE20-like protein kinase 3 | MTC35 | C1509T; A2216G | | |
| DUSP6 dual specificity MAP kinase phosphatase | MTC23 | | | G666A (Trp—STOP); T691G (Leu—Val); T781G (Ser—Ala) |
| Perflin | MTC36 | T905C | | |
| P8 - Candidate of metastasis 1 | MTC17 | | | C110T (Thr—Ile) |
| Lipocortin | MTC14 MTC15 | A1267T | G179A; A401G | C300T (Gln—STOP) |
| 5-lipoxygenase | MTC25 | C2328T | | |
| Type IV collagenase | MTC8 | A2196C | C1102T; A1333G; C1759T | |
| LFA-1/CR3/ P150, 95 beta-subunit | MTC6 | G2505A; G2553C | A891G | A638G (Asn—Ser) |
| Integrin alpha-3 | MTC30 | C3773T | | G2228A (Ala—Thr) |

Table 2, columns 1 and 2 provide the gene name and corresponding MTC reference number, respectively. Columns 3–5 provide the nucleotide position in which the polymorphism occurs, with the nucleotide present in the polymorphic allele following the number, and the nucleotide it replaces preceding the number. Column 3 lists polymorphisms occurring in the 5' or 3' non-translated regions of genes, while column 4 lists polymorphisms which occur in coding regions but which do not result in an altered encoded polypeptide. Column 5 lists polymorphisms which do result in a change of the encoded amino acid sequence.

In general, polymorphisms according to the invention can be identified using any nucleic acid probe which specifically identifies the polymorphic allele.

Examples of nucleic acid probes which recognize SNPs according to the invention are provided below. Listed are the gene from which the SNP is identified, with the polymorphic site indicated with an ">". The frequency with which the polymorphic nucleotide appeared in a sampled population is given in parentheseses.

KIAA1131 (gbeh__aa570716)

(SEQ ID NO:5)

CATAAGCCCTTGTAAAGTAAC A>G(2/214) CAGTGT-TCTGTGCTATATACTTGCT (SEQ ID NO:16)

CAGTGTTCTGTGCTATATAC T>C(3/214) TGCTG-GCTGGGTAGT (SEQIDNO:17)

GTGTCATTAGCATGGTGG>A(3/190) ATCATATACTTCTCTGCACACAAACAC
(SEQ ID NO:18)
AGCATGGTGGAT C>A(2/190) ATATACTTCTCTGCACACAAACA
Periplakin (af0113717)
(SEQ ID NO:19)
TTCATGCTATAAATAAA T<G(6/13) TTCCCTATTAGTTCCC
(SEQ ID NO:20)
GGTTTTAAGCCAGAA G<A(4/13) TCTGGAGAGATGTCATGCCAG
(SEQ ID NO:21)
CTCCAGCTGCAGGTTTT G>C(4/9) CCTCTCCAGCTGTAATTTGT
(SEQ ID NO:22)
GCTCTCGGCAAAGGC A>G(3/6) CTCGCCTCGGCCC
(SEQ ID NO:23)
ACGATCTCCCGCACCTTCTCCTG C>T(3/8) ACCACCACTTTGGCGTTCTCCT
(SEQ ID NO:24)
TGCTCGTATTTCCGGTTGGTGTCCTCCACC C>T(3/6)
(SEQ ID NO:25)
GGGTCCTCAGCAGGGGTGTGGTG
Mitochondrial Proteolipid (af054175)
(SEQ ID NO: 26)
GGCTTGCTGAAATTTA C>T(4/190) AGGCAGACTGACGTTTT
(SEQ ID NO:27)
ACTGACGTTTTC T>C(3/190) TTCACATGTACTCC
(SEQ ID NO:28)
ATTTTATAAACGATG A>G(3/170) AGCCCATCAGCCCCATT
(SEQ ID NO:29)
TTCATGGGGATCCATA T>C(8/44) GTTTTTAATAATACTTT
Phosphatase-1 gamma 1 (107395)
(SEQ ID NO:30)
TTTTAACTTATAAGCC T>C(2/130) CAACTTCACCGCAGAATAAAGAATGTAG
(SEQ ID NO:31)
AGAAGGCAGCATGTGTA T>C(13/45) ACAACCATACC
Prostaglandin Transporter hPGT (u70867)
(SEQ ID NO:32)
GCGCTTTGTTTTCTCTCTACAA G>A(5/11) CCATTCCCCGC
(SEQ ID NO:33)
TGCCTCCAGAGAGGTGG G>A(3/7) TGCCTGGGTTGAGAGACACAGCT
(SEQ ID NO:34)
GAGGTCATTCATCAACAAATAT A>G(4/8) TTTATTGGAGACCGACTTT
E-cadherin (z18923)
(SEQ ID NO:35)
GTGTGTGACTGTGAAGGGGCCGC C>T(2/12) GGCGTCTGTAGGAA
Kinectin (z22551)
(SEQ ID NO:36)
CAATGTGATCCTATAA A>C(3/8) ACCCTGTGCGGCCGGGAAAG
Staf50 (x82200)
(SEQ ID NO:37)
TAATTCCTTTTCTTTTCTTC T>C(3/12) TTATTTCCTCTGCCCCTT
(SEQ ID NO:38)
AAAATTAAAGCAAGAAGTCCA T>C(3/14) AGTAATTTATTTGC Proteasome Subunit HC5 (d00761)
(SEQ ID NO:39)
CAAGTGCCATGCTACA G>C(5/240) CCCCTGCTTGACAACCAGGTT
Proteasome Activator hPA28 Subunit Beta (d45248)
(SEQ ID NO:40)
TCCAGACTTCTGGCTTAA C>A(3/95) CAGGGCAAGCAGGGACAGGACTTT
(SEQID NO:41)
AAATCCACACTTA G>T(2/55) GGACTTCTTTCTTCTCC
STE20-like Protein Kinase 3 (AF083420)
(SEQ ID NO:42)
GAAAAAGGAAATCAACCTC T>C(11/62) AGGTGTACCAAAAGGGGC
(SEQ ID NO:43)
GGAGGAGGATGAAGAAGGAAAAAA G>A(3/9) GAAAAACAAAACCCCAAATGCC
DUSP6 Dual Specificity MAP Kinase Phosphatase (AB013382)
(SEQ ID NO:44)
CTCGCAATGCAGGG A>C(4/32) GAACTCGGCTTGGAA
(SEQ ID NO:45)
CTTGAGCAGCAGCCCGAGCA A>C(20/38) CGACTCGCCGCCCGTATTCTCGT
(SEQ ID NO:46)
CGCCGCCCGTATTCTCGTT C>T(2/38) CAGTCGCTGCTGCTCTCGTCGT
Peflin (gbeh_h72140)
(SEQ ID NO:47)
CTCTAAGAAGCCAGGAA A>G(2/32) GGTCCCTGGTGCACTCCACTCT
P8—Candidate of Metastasis 1 (AF069073)
(SEQ ID NO:48)
GGTTGCTGGTGGGAAG G>A(2/80) TGGCCATCGTGCCTGGC
Lipocortin (x05908)
(SEQ ID NO:49)
AAAGGTGGTCCCGGATCAGC G>A(2/60) GTGAGCCCCTATCCTACC
(SEQ ID NO:50)
TTCTAACTAAGCGAAACAATGCA C>T(2/90) AGCGTCAACAGATCAAAGCAGCATAT
(SEQ ID NO:51)
TTGAGGAGGTTGTTTT A>G( 11/60) GCTCTGCTAAAAACTCCAGCG
(SEQ ID NO:52)
AAATCATTTTTATATTATA A>T(2/60) CTCTGTATAATAGAGATAAGT
5-lipoxygenase (j03571)
(SEQ ID NO:53)
AGACATCTATCAGGGTC G>A(3/34) TGATTTGCTGTTGCTGCTT
Type IV collagenase (j03210)
(SEQ ID NO:54)
TGAAAATATCAAAG T>G(3/9) ATCTCTTTAGGGG
(SEQ ID NO:55)
CTGCGATGAGCTTGGG A>G(9/18) AAGCCAGGATCCATTTTCTT
(SEQ ID NO:56)
AGTGACAGGGCCCAG T>C(21/63) GTGGGGGTGGGGCCGGTGCCAA
(SEQ ID NO:57)
GCCCCACTTGCGGTC G>A(8/80) TCATCGTAGTTGGCTGTGGT Cell Surface Adhesion Glycoproteins LFA-1/CR3/P150, 95 Beta-subunit (m15395)
(SEQ ID NO:58)
GGAGCTGTCCCCC C>G(6/18) GACGAGCCCCAG
(SEQ ID NO:59)
CATTTGAGGG C>T(4/28) GGAAAATAACTG
(SEQ ID NO:60)
TGGCGCCCAGCTT C>T(4/12) CCGTCGCCCGCGAA
(SEQ ID NO:61)
CCTTGTTGGGGCATGGG T>C(2/16) TTCGCAGCT-TATC
Integrin Alpha-3 (m59911)
(SEQ ID NO:62)
GCCTTTTCCTCCC G>A(3/13) GCTCTGGTGGGAGG
(SEQ ID NO:63)
ATGACCTCAAAGG C>T(3/33) GATGAGCAGCT The invention also includes nucleic acid sequences that include one or more polymorphic MTC sequences. Also included are methods of identifying a base occupying a polymorphic in an MTC sequence, as well as methods of identifying an individualized therapeutic agent for treating pathologies (e.g., carcinomas, including metastatic carcinomas such as metastatic thyroid carcinomas) based on MTC sequence polymorphisms.

The nucleotide polymorphism can be a single nucleotide polymorphism (SNP). A SNP occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Polymorphic sequences according to the present invention can include those shown in Table 2. Table 2 describes nine MTC sequences for which polymorphisms have been identified. The first column of the table lists the names assigned to the sequences in which the polymorphisms occur. The second and third columns list the rat and human GenBank Accession numbers for the respective sequences. The forth column lists the position in the sequence in which the polymorphic site has been found. The fifth column lists the base occupying the polymorphic site in the sequence in the database, i.e., the wildtype. The sixth column lists the alternative base at the polymorphic site. The seventh column lists any amino acid change that occurs due to the polymorphism.

The polymorphic sequence can include one or more of the following sequences: (1) a sequence having the nucleotide denoted in Table 2, column 5 at the polymorphic site in the polymorphic sequence, and (2) a sequence having a nucleotide other than the nucleotide denoted in Table 2, column 5. An example of the latter sequence is a polymorphic sequence having the nucleotide denoted in Table 2, column 6 at the polymorphic site in the polymorphic sequence.

For example, a polymorphism according to the invention includes a sequence polymorphism in the ATP citrate lyase gene having the nucleotide sequence of GenBank Accession No. x64330, in which the cytosine at nucleotide 609 is replaced by adenosine. In some embodiments the polymorphic sequence includes a nucleotide sequence of ATP citrate gene having the GenBank Accession No. x64330, wherein the nucleotide at 609 is any nucleotide other that cytosine. In some embodiments, the polymorphic sequence includes the full length of any one of the nine genes in Table2. In other embodiments, the polymorphic sequence includes a polynucleotide that is between 10 and 100 nucleotides, 10 and 75 nucleotides, 10 and 50 nucleotides, or 10 and 25 nucleotides in length.

The invention will be further described in the following examples, which do not limit the scope of the invention described in the claims. The following examples illustrate the identification and characterization of genes differentially expressed in thyroid follicular adenomas and metastatic papillary carcinomas.

EXAMPLE 1
RNA PREPARATION

Following treatment, total cellular RNA was isolated with Trizol (GIBCO-BRL, Baltimore Md.), using one-tenth volume of bromochloropropane (Molecular Research Corp., Cincinnati Ohio) for phase separation. Contaminating DNA was removed by treatment with DNAse I (Promega, Milwaukee Wis.) in the presence of 0.01M DTT (GIBCO-BRL, Baltimore Md.) and 1 unit/$\mu$l Rnasin (Promega, Milwaukee Wis.). Following phenol/chloroform extraction, RNA quality was evaluated by spectrophotomety and formaldehyde agarose gel electrophoresis, and RNA yield was estimated by fluorometry with OliGreen (Molecular Probes, Eugene Oreg.). Poly(A)+RNA was prepared from 100 $\mu$g total RNA using oligo(dT) paramagnetic beads (PerSeptive Biosynthesis, Boston Mass.), and quantitated with fluorometry.

EXAMPLE 2
CDNA SYNTHESIS

First strand cDNA was prepared from 1.0 $\mu$g of poly(A)+ RNA with 200 pmoles oligo(dT)25V (V=A, C or G) (PerSeptive Biosynthesis, Boston Mass.) using 40 units of Superscript II (GIBCO-BRL, Baltimore Md.). Second strand synthesis was performed at 16° C. for 2 h following the addition of 10 units of E. coli DNA ligase (GIBCO-BRL, Baltimore Md.), 40 units of E. coli DNA polymerase (GIBCO-BRL, Baltimore Md.), and 3.5 units of E. coli RNase H (GIBCO-BRL, Baltimore Md.). 1 $\mu$l of T4 DNA polymerase (GIBCO-BRL, Baltimore Md.) was then added, and incubation at 16° C. was continued for 5 min. The reaction was then treated with 5 units of arctic shrimp alkaline phosphatase (USB, Chicago Ill.) at 37° C. for 30 min., and cDNA purified by phenol/chloroform extraction. The yield of cDNA was estimated using fluorometry.

EXAMPLE 3
GENECALLING™ CHEMISTRY

For all samples, triplicate GeneCalling chemistry reactions were executed in parallel for each of 96 subsequence pairs. Restriction endonuclease digestion is performed in a reaction mix containing 2.6 $\mu$l H$_2$O, 2 $\mu$l 5M betaine (Sigma, St. Louis Mo.), 1 $\mu$l 10× restriction endonuclease buffer, 0.8 $\mu$l 10 mM ATP (Pharmacia, Newark N.J.), 1 $\mu$l 25% PEG (Fluka, St. Louis Mo.), 0.2 $\mu$l Restriction enzyme 1 (NEB, Beverly Mass., or Fermentas, Amherst N.J.), 0.2 $\mu$l Restriction enzyme 2, 1 $\mu$l cDNA (Ing/$\mu$l).

Digestion of cDNA is performed with the following thermocycler program: 30 mm @ 37° C., 22 min ramp to 16° C., 1 hour @ 16° C., 15 min @ 37° C.,and 20 min @ 72° C. Following digestion 0.2 $\mu$l Ligase (BRL, Baltimore Md.) with 1 $\mu$l Primer set 1 (Genosys, The Woodlands Tex., or Amitof, Boston Mass.), 1 $\mu$l Primer set 2 are added to the mix. The reactions are then maintained at 16° C. for ligation of PCR primers. For PCR, the following reagents are added: 2 $\mu$l 10 mM dNTP (USB, Chicago Ill.), 5 $\mu$l 10×TB buffer (500 mM Tris pH 9.15, 160 mM $(NH_4)_2SO_4$, 20 mM $MgCl_2$), 0.25 µl Klentaq (Invitrogen, Carlsbad Calif.): PFU (Stratagene, Los Angeles Calif.) (16:1), 32.751 µl $H_2O$. 20 cycles of amplification (30 sec @ 96° C., 1 sec @ 57° C., 2 min @ 72° C.) were followed with 10 min @ 72° C. PCR product purification was performed using MPG streptavidin beads (CPG, Lincoln Park N.J.). After washing the beads twice with buffer 1 (3M NaCI, 10 mM TRIS, pH 7.5, 1 mM EDTA), 20 µl were mixed with the PCR product for 10 min at room temperature. separated with a magnet, and washed once with buffer 2 (10 mM TRIS, pH 8.0, 1 mM EDTA). The beads were then dried and resuspended in 3 µl of buffer 3 (80% formamide, 4 mM EDTA, 5% ROX-tagged molecular size standard (ABI, San Francisco Calif.)). In addition, every other lane received 5% TAMRA (ABI, San Francisco Calif.) as interlane bleed control. Following denaturation (96° C. for 3 min), samples were loaded onto 5% polyacrylamide, 6M urea, 1×TBE ultrathin gels (Long-Ranger, FMC, Philadelphia Pa.), and electrophoresed for 60 min at 3500 V on a Niagara™ instrument.

EXAMPLE 4
OPEN GENOME INITIATIVE™ SOFTWARE GEL INTERPRETATION

The output of the electrophoresis instruments are processed using the internet-based Open Genome Initiative™ (OGI™) software suite. Gel images are visually inspected for overall quality and each lane tracked to delineanate the path of best fit. Each lane contains a GeneCalling sample plus two sizing ladders (labeled with ROX and TAMRA fluorochrome) spanning the range from 50 to 500 bp. The ladder peaks provide a relationship between camera frames (typically collected at 1 Hz) and base pairs. After tracking, lanes are extracted and the peaks in the sizing ladder are resolved. Linear interpolation between the ladder peaks converts the GeneCalling sample traces from frames to base pairs. Each trace is evaluated and ruled out for low signal-to-noise, poor peak resolution, absent ladder peaks, and lane-to-lane bleed. Lanes that pass all criteria are submitted as point-by-point length vs. amplitude addresses to the GeneScape Oracle 8 database. Submitted traces are then organized by treatment group and fragmentation primers. The 9 traces corresponding to each treatment group/fragmentation pattern are superimposed and are manually evaluated for intertrace alignment fidelity. Misaligned traces are rejected and excluded from subsequent analyses.

EXAMPLE 5
GENE ISOLATION

1 µl of the GENECALLING™ chemistry reaction containing the peak of interest is added to 3 µl of 1×TAE buffer (Sigma, St. Louis Mo.) and 1 µl of gel loading dye (Elchrom Scientific, Lake Park Fla.) and electrophoresed on an Elchrom Mini Gel (Elchrom Scientific, Lake Park Fla.) at 55° C. 120 V for 30'–150' depending upon the size of the selected fragment. Following 15' of ethidium bromide staining, the desired band length is excised from gel lane, placed into 10 mM MgCl2, centrifuged at 3000 RPM for 5' and heated to 65° C. for 30'. Eluted fragments are PCR-amplified using J23 & R23 PCR primers (Amitof, Boston Mass.) and cDNA polymerase (Clontech. Palo Alto Calif.) for 25 cycles of 30" @96° C., 60" @57° C., 2' @72° C. 3 µl aliquot is ligated to pCR2.1 cloning vector (Invitrogen, Carlsbad Calif.) using the Fast-Link DNA ligation kit (Epicenter, Madison Wis.). Vectors are electroporated into DH10B *E. coli* with 1.8 mV pulses and cells are then plated on LB plates with ampicillin, kanamycin, and x-gal (Northeast Laboratories. Waterville Mass.). Colonies with inserts are selected for PCR amplification using 5M betaine (Sigma, St. Louis Mo.), DYN-A & DYN-RE primers (Amitof, Boston Mass.) and polymerase (Clontech, Palo Alto Calif.) for 29 cycles of 1' @96° C., 1' @72° C. PCR products are submitted to sequencing for clone identification.

EXAMPLE 6
CLONE SEQUENCING

30 µl of clone template are added to 6 µl of SPRI beads (Bangs Laboratories, Inc., Fishers Ind.) in 0.5 M EDTA pH 8.0 (Amresco, Solon Ohio) and 30 µl hybridization buffer (2.5 M NaCl, 20% PEG 8000 (Sigma, St. Louis Mo.)) in 96-well plate format. Plates are shaken for 5' at 600 rpm and settled for 2' on a magnet. The beads are washed 4× with 200 µl of 70% EtOH(AAPER, Louisville Ky.) and air dried for 2 min. 36 µl of Nanopure H20 is added to the beads. Plates are again shaken for 5' at 600 rpm and the supernatant is collected for sequencing.

3 µl of purified product is transferred to each of A (JOE-fluor). G (TAMRA-fluor), C (FAM-fluor) and T (ROX-fluor) reaction mixes (2 µl DYEnamic Direct Cycle sequencing kit: DYEnamic-M13-40ET primers, premixed dGTP, Taq polymerase(Amersham Life Sciences, Piscataway N.J.) and 1.8 ml dNTP (Amersham Life Sciences, Piscataway N.J.)) in 384-well format. Plates are placed in a thermocycler for 15 cycles of 5" @96° C., 10" @52° C., 60" @72° C. Reactions are quenched at 4° C. For each template, the four reactions are pooled into one well of a 96-well plate and 65 µl of 100% EtOH (AAPER, Louisville Ky.) are added. Plates are chilled at 4° C. for 60 mm and centrifuged at 4° C. for 30 min at 2000 rpm. The supernatant is removed and the plates are air dried to completion at 25° C. 3 µl of formamide loading dye (Amersham, Piscataway N.J.) is added to each well. In addition, 960 µl of TAMRA-spiked loading dye (10:1 formamide (Amersham, Piscataway N.J.): 55mer TAMRA (Amitof, Boston Mass.)) is added to select wells for electrophoresis quality control. Samples are electrophoresed in a 1×TBE Long Ranger (FMC, Philadelphia PA) polyacrylamide gel on the AB1377 (ABI, San Fransisco Calif.) platform for 2.5 hrs at 3000 volts.

Gel images are resolved and interpreted by the OGI software interface. Images are quality controlled for overall image fidelity arid sequence quality of individual lanes. Lanes with truncated sequences, absent signals in one or more channels, bleed and primer dimer are failed and removed from further analysis. The sequences are Base-Called and imported into GeneScape assigned to the difference peak corresponding to the sequence.

EXAMPLE 7
OLIGONUCLEOTIDE POISONING

Restriction fragments which map in end sequence and length to known rat genes are used as templates for the design of unlabeled oligonucleotide primers. An unlabeled oligonucleotide designed against one end of the restriction fragment is added in excess to the original reaction. and is re-amplified for an additional 15 cycles. This reaction is then electrophoresed and compared to a control reaction reamplified without the unlabeled oligonucleotide to evaluate the selective diminution of the peak of interest.

EXAMPLE 8
NORTHERN BLOT ANLYSIS

1 µg of Poly-A+RNA prepared as described above was transferred to Hybond plus membranes (Amersham. Piscataway N.J.) and hybridized using standard techniques. Probes for cloned fragments were reamplified from isolated *E.coli* colonies containing the appropriate insert as described above and subcloned into the pCR2.1 vector (Invitrogen). Probes for GeneCalled fragments were obtained following PCR amplification of the fragment from sample cDNA prepared as described above using primers designed from the predicted database sequence designed to overlap the restriction enzyme sites of the GeneCalled gene fragment and allow subcloning into the pCR2.1 vector. 1 ng of plasmid was combined with 0.2 uM of M13FSP6 forward and M13RT3 reverse primers and 200 uM of each dNTP in 1× PCR buffer with 0.5 ul cDNA Taq polymerase (Clontech). The mixture was subject 5' @94° C. followed by 5× of 5" @94° C./3' @72° C., 5× of 5" @94° C. /3 ' @70° C., and 15× of 5" @94° C./3' @68° C. PCR products were electrophoresed through a 1% low melting agarose gel and purified using the Qiaex II gel extraction kit (Qiagen). The RNA probe was transcribed using the Stip-EZ RNA probe synthesis kit (Ambion). 100 ng of purified probe was labelled using 25 uCi of 33P-UTP (Amersham) using either SP6 or T3 polymerase to capture the noncoding strand of the probe. Following transcription, 1 ul of DNAse I was added and incubated at 37° C. for 15. Unincorporated nucleotides were removed using ProbeQuant G-50 micro columns (Pharmacia Biotech) and the probe was quantitated using a Bioscan QC-4000 (Bioscan).

RNA probes were hybridized to the Northern blots at 65° C. in a Robbins Scientific Model 400 hybridization incubator. The blots were prehybridized at 65° C. in 10 ml of Zip-Hyb (Ambion) for 30' and then $10^6$ dpm/ml of RNA probe in 1 ml of Zip-Hyb was added to the Northern for a 2 hr incubation. Following hybridization, the buffer was removed and the blots were washed first in 2×SSC. 0.1% SDS×15' @65° C. then in 0.1×SSC. 0.1% SDS×15, @65° C. The blots were wrapped in Saran Wrap (Dow) and exposed to phosphor screens (Molecular Dynamics) overnight. The screens were scanned on a Storm 840 (Molecular Dynamics) at 50 um resolution.

EXAMPLE 9

DATABASE QUERY FOR SAGE EXPRESSION ANALYSIS

Serial Analysis of Gene Expression, or SAGE, is an experimental technique designed to gain a quantitative measure of gene expression. The SAGE technique itself includes several steps utilizing molecular biological, DNA sequencing and bioinformatics techniques. These steps (reviewed in Adams Md., "Serial analysis of gene expression: ESTs get smaller." Bioessays. 18(4):261–2 (1996)) have been used to produce 9 or 10 base "tags", which are then, in some manner, assigned gene descriptions. For experimental reasons, these tags are immediately adjacent to the 3' end of the 3'-most N1aIII restriction site in cDNA sequences. The Cancer Genome Anatomy Project, or CGAP, is an NCI-initiated and sponsored project, which hopes to delineate the molecular fingerprint of the cancer cell. It has created a database of those cancer-related projects that used SAGE analysis in order to gain insight into the initiation and development of cancer in the human body. The SAGE expression profiles reported in this invention are generated by first identifying the Unigene accession ID associated with the given MTC gene by querying the Unigene database at http://www.ncbi.nlm.nih.gov/UniGene/. This page has then a link to the SAGE:Gene to Tag mapping (htt://www.ncbi.nlm.nih.gov/SAGEcid.cgi?cid="unigeneID").

This generated the reports that are included in this application, which list the number of tags found for the given gene in a given sample along with the relative expression. This information is then used to understand whether the gene has a more general role in tumorogenesis and/or tumor progression. A list of the SAGE libraries generated by CGAP and used in the analysis can be found at http://www.ncbi.nlm.nih.gov/SAGE/sagelb.cgi.

OTHER EMBODIMENTS

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, the neoplasm described herein can be a thyroid carcinoma, a breast carcinoma, a colorectal carcinoma, and/or an ovarian carcinoma. Similarly, the methods described herein can also be used for metastatic neoplasms from non-thyroid tumors, e.g., carcinomas such as ovarian, breast, and colorectal carcinomas.

What is claimed is:

1. A method of categorizing a thyroid carcinoma in a subject, the method comprising:
   a) providing a test cell population from said subject, wherein at least one cell in said test cell population expresses the nucleic acid sequence MTC: 33;
   b) measuring the expression of MTC:33 in said test cell population;
   c) comparing the expression of MTC:33 to the expression of MTC:33 in a reference cell population comprising at least one cell whose thyroid carcinoma stage is known; and
   d) identifying a difference in expression levels of MTC33, if present, in the test cell population and reference cell population,
thereby categorizing said thyroid carcinoma in said subject.

2. The method of claim 1, wherein said carcinoma is a metastatic papillary thyroid carcinoma.

3. The method of claim 1, wherein an alteration of the expression of MTC:33 in said test cell population as compared to said reference cell population indicates that the test cell population has a different thyroid carcinoma stage than the cells in said reference cell population.

4. The method of claim 1, wherein a similar expression pattern of MTC:33 in said test cell population as compared to said reference cell population indicates that the test cell population has the same thyroid carcinoma stage as the cells in said reference cell population.

5. The method of claim 1, wherein said subject is a human.

6. The method of claim 1, wherein said reference cell population comprises a plurality of cells or a database.

7. The method of claim 1, wherein said thyroid carcinoma is a mestastic thyroid carcinoma.

* * * * *

SEQUENCE LISTING

<160> NUMBER OF SEQ ID NOS: 63

<210> SEQ ID NO 1
<211> LENGTH: 2132
<212> TYPE: DNA
<213> ORGANISM: Homo sapiens

<400> SEQUENCE: 1

```
ggcgcccggg cggtgctgcg ctgccagagc ccgcgcatgg tgtggaccca ggaccggctg      60
cacgaccgcc agcgcgtgct ccactgggac ctgcgcggcc ccggggtgg ccccgcgcgg      120 cgcctgctgg acttgtactc ggcgggcgag cagcgcgtgt acgaggcgcg ggaccgcggc      180
cgcctggagc tctcggcctc ggccttcgac gacggcaact tctcgctgct catccgcgcg      240
gtggaggaga cggacgcggg gctgtacacc tgcaacctgc accatcacta ctgccacctc      300
tacgagagcc tggccgtccg cctggaggtc accgacggcc ccccggccac ccccgcctac      360
```

-continued

```
tgggacggcg agaaggaggt gctggcggtg gcgcgcggcg cacccgcgct tctgacctgc    420
gtgaaccgcg ggcacgtgtg gaccgaccgg cacgtggagg aggctcaaca ggtggtgcac    480
tgggaccggc agccgcccgg ggtcccgcac gaccgcgcgg accgcctgct ggacctctac    540
gcgtcgggcg agcgccgcgc ctacgggccc cttttcctgc gcgaccgcgt ggctgtgggc    600
gcggatgcct ttgagcgcgg tgacttctca ctgcgtatcg agccgctgga ggtcgccgac    660
gagggcacct actcctgcca cctgcaccac cattactgtg gcctgcacga acgccgcgtc    720
ttccacctga cggtcgccga accccacgcg agccgccccc ccggggctc tccgggcaac     780 ggctccagcc acagcggcgc cccaggccca gaccccacac tggcgcgcgg ccacaacgtc    840
atcaatgtca tcgtccccga gagccgagcc cacttcttcc agcagctggg ctacgtgctg    900
gccacgctgc tgctcttcat cctgctactg gtcactgtcc tcctggccgc ccgcaggcgc    960
cgcggaggct acgaatactc ggaccagaag tcgggaaagt caaagggaa ggatgttaac     1020 ttggcggagt cgctgtggc tgcaggggac cagatgcttt acaggagtga ggacatccag     1080
ctagattaca aaacaacat cctgaaggag agggcggagc tggcccacag ccccctgcct     1140
gccaagtaca tcgacctaga caaagggttc cggaaggaga actgcaaata gggaggccct    1200
gggctcctgg ctgggccagc agctgcacct ctcctgtctg tgctcctcgg gcatctcct    1260 gatgctccgg ggctcacccc ccttccagcg gctggtcccg ctttcctgga atttggcctg    1320
ggcgtatgca gaggccgcct ccacacccct ccccaggggg cttggtggca gcatagcccc    1380
cacccctgcg gcctttgctc acgggtgggc cctgcccacc cctgggcaca accaaaatcc    1440
cactgatgcc catcatgccc tcagacccct ctgggctctg cccgctgggg gcctgaagac    1500
attcctggag gacactccca tcagaacctg gcagccccaa aactgggtc agcctcaggg     1560 caggagtccc actcctccag ggctctgctc gtccggggct gggagatgtt cctggaggag    1620
gacactccca tcagaacttg gcagccttga agttggggtc agcctcggca ggagtcccac    1680
tcctcctggg gtgctgcctg ccaccaagag ctcccccacc tgtaccacca tgtgggactc    1740
caggcaccat ctgttctccc cagggacctg ctgacttgaa tgccagccct tgctcctctg    1800
tgttgctttg ggccacctgg ggctgcaccc cctgcccttt ctctgcccca tccctaccct    1860
agccttgctc tcagccacct tgatagtcac tgggctccct gtgacttctg accctgacac    1920
ccctcccttg gactctgcct gggctggagt ctagggctgg ggctacattt ggcttctgta    1980
ctggctgagg acaggggagg gagtgaagtt ggtttgggt ggcctgtgtt gccactctca     2040
gcaccccaca tttgcatctg ctggtggacc tgccaccatc acaataaagt ccccatctga    2100 ttttttaaaaa aaaaaaaaaa aaaaaaaaaa aa                                  2132
```

<210> SEQ ID NO 2
<211> LENGTH: 384
<212> TYPE: PRT
<213> ORGANISM: Homo sapiens

<400> SEQUENCE: 2

```
Met Val Trp Thr Gln Asp Arg Leu His Asp Arg Gln Arg Val Leu His
  1               5                  10                  15

Trp Asp Leu Arg Gly Pro Gly Gly Gly Pro Ala Arg Arg Leu Leu Asp
                 20                  25                  30

Leu Tyr Ser Ala Gly Glu Gln Arg Val Tyr Glu Ala Arg Asp Arg Gly
             35                  40                  45

Arg Leu Glu Leu Ser Ala Ser Ala Phe Asp Asp Gly Asn Phe Ser Leu
         50                  55                  60
```

```
Leu Ile Arg Ala Val Glu Glu Thr Asp Ala Gly Leu Tyr Thr Cys Asn
 65                  70                  75                  80

Leu His His His Tyr Cys His Leu Tyr Glu Ser Leu Ala Val Arg Leu
                 85                  90                  95

Glu Val Thr Asp Gly Pro Pro Ala Thr Pro Ala Tyr Trp Asp Gly Glu
            100                 105                 110

Lys Glu Val Leu Ala Val Ala Arg Gly Ala Pro Ala Leu Leu Thr Cys
        115                 120                 125

Val Asn Arg Gly His Val Trp Thr Asp Arg His Val Glu Glu Ala Gln
130                 135                 140

Gln Val Val His Trp Asp Arg Gln Pro Pro Gly Val Pro His Asp Arg
145                 150                 155                 160

Ala Asp Arg Leu Leu Asp Leu Tyr Ala Ser Gly Glu Arg Arg Ala Tyr
                165                 170                 175

Gly Pro Leu Phe Leu Arg Asp Arg Val Ala Val Gly Ala Asp Ala Phe
            180                 185                 190

Glu Arg Gly Asp Phe Ser Leu Arg Ile Glu Pro Leu Glu Val Ala Asp
        195                 200                 205

Glu Gly Thr Tyr Ser Cys His Leu His His Tyr Cys Gly Leu His
210                 215                 220

Glu Arg Arg Val Phe His Leu Thr Val Ala Glu Pro His Ala Glu Pro
225                 230                 235                 240

Pro Pro Arg Gly Ser Pro Gly Asn Gly Ser Ser His Ser Gly Ala Pro
                245                 250                 255

Gly Pro Asp Pro Thr Leu Ala Arg Gly His Asn Val Ile Asn Val Ile
            260                 265                 270

Val Pro Glu Ser Arg Ala His Phe Phe Gln Gln Leu Gly Tyr Val Leu
        275                 280                 285

Ala Thr Leu Leu Leu Phe Ile Leu Leu Leu Val Thr Val Leu Leu Ala
290                 295                 300

Ala Arg Arg Arg Arg Gly Gly Tyr Glu Tyr Ser Asp Gln Lys Ser Gly
305                 310                 315                 320

Lys Ser Lys Gly Lys Asp Val Asn Leu Ala Glu Phe Ala Val Ala Ala
                325                 330                 335

Gly Asp Gln Met Leu Tyr Arg Ser Glu Asp Ile Gln Leu Asp Tyr Lys
            340                 345                 350

Asn Asn Ile Leu Lys Glu Arg Ala Glu Leu Ala His Ser Pro Leu Pro
        355                 360                 365

Ala Lys Tyr Ile Asp Leu Asp Lys Gly Phe Arg Lys Glu Asn Cys Lys
370                 375                 380

<210> SEQ ID NO 3
<211> LENGTH: 1218
<212> TYPE: DNA
<213> ORGANISM: Murinae gen. sp.

<400> SEQUENCE: 3
ttcggcacag gacctgcacc atcactactg ccacctcgat gagagcatgg ctgtgcgcct      60
cgaggttaca gaggatcccc tattaagtcg cgcatactgg gacggtgaga aggaagtgtt     120
ggaggtggcc catggcgcgc cggcactgat gacctgcatc aaccgtgcgc acgtgtggac     180
tgaccgccat ttagaggagg cgcaacagga tagacaattg gacgacagc tacctggggt     240 gtcacacgac cgcgccgacc gcctgcatga cctgtatgca tctggcgagc gccgcgccta     300
```

-continued

```
tgggccaccc ttcctgcgtg atcgcgtgtc agtgaacacc aacgcttttg cacgcggtga    360
cttctcccta cgcatcgatg agctggagcg agctgatgag ggcatctatt cctgccacct    420
gcaccatcac tactgtggcc tccacgagcg ccgagtcttc cacctacagg tcacagagcc    480
tgcctttgag ccaccagctc gtgcttctcc tggcaatggg tctggtcaca gcagtgctcc    540
tagcccagat cccaccctga cccgaggcca gcatcatc aatgtcattt gtcccagagg      600
accacacaca tttcttccag caactgggct atgtgttggc cacgctgctg ctcttcatct    660
tgctgctcat cactgtagtc ctggctacac gatatcgtca cagcggagga tgcaagacgt    720
cggacaaaaa agctgggaag tcaaggggaa aggaatgtcg acacgatggt ggagtttgct    780
gtagccacaa gggatcaggc tccatatagg actgaggaca tccagctaga ttacaaaaac    840
aacatcctgc ggtattcctg gctcttctca gcggctggtc cgacttacct agaaacttgg    900
cagagcagct gcctgtactt tgcccttcct agaatcgcca cccctcatct tggtgagcaa    960
ctgtgggttc cctagagact ctggtatagt acgattgctg cccttcacct gtgcccactg   1020
atggttgtac ccccaactta aacacaacaa agatcccttg ttaatatcca ccaaatgcaa   1080
agtccctcgt ggcctcttac tgctagggtc aggaagacac ttaaaaattc cagttaagac   1140
tccctagcca ccagttaaac acattagcca ttgtcctggg gggtctcctg agctgcattg   1200
tgcctgtgta ctgttcag                                                 1218
```

<210> SEQ ID NO 4
<211> LENGTH: 260
<212> TYPE: PRT
<213> ORGANISM: Murinae gen. sp.

<400> SEQUENCE: 4

```
Ser Ala Gln Asp Leu His His His Tyr Cys His Leu Asp Glu Ser Met
  1               5                  10                  15

Ala Val Arg Leu Glu Val Thr Glu Asp Pro Leu Leu Ser Arg Ala Tyr
             20                  25                  30

Trp Asp Gly Glu Lys Glu Val Leu Glu Val Ala His Gly Ala Pro Ala
         35                  40                  45

Leu Met Thr Cys Ile Asn Arg Ala His Val Trp Thr Asp Arg His Leu
     50                  55                  60

Glu Glu Ala Gln Gln Asp Arg Gln Leu Gly Arg Gln Leu Pro Gly Val
 65                  70                  75                  80

Ser His Asp Arg Ala Asp Arg Leu His Asp Leu Tyr Ala Ser Gly Glu
                 85                  90                  95

Arg Arg Ala Tyr Gly Pro Pro Phe Leu Arg Asp Arg Val Ser Val Asn
            100                 105                 110

Thr Asn Ala Phe Ala Arg Gly Asp Phe Ser Leu Arg Ile Asp Glu Leu
        115                 120                 125

Glu Arg Ala Asp Glu Gly Ile Tyr Ser Cys His Leu His His His Tyr
    130                 135                 140

Cys Gly Leu His Glu Arg Arg Val Phe His Leu Gln Val Thr Glu Pro
145                 150                 155                 160

Ala Phe Glu Pro Pro Ala Arg Ala Ser Pro Gly Asn Gly Ser Gly His
                165                 170                 175

Ser Ser Ala Pro Ser Pro Asp Pro Thr Leu Thr Arg Gly His Ser Ile
            180                 185                 190

Ile Asn Val Ile Cys Pro Arg Gly Pro His Thr Phe Leu Pro Ala Thr
        195                 200                 205
```

```
Gly Leu Cys Val Gly His Ala Ala Ala Leu His Leu Ala Ala His His
        210                 215                 220

Cys Ser Pro Gly Tyr Thr Ile Ser Ser Gln Arg Arg Met Gln Asp Val
225                 230                 235                 240

Gly Gln Lys Ser Trp Glu Val Lys Gly Glu Gly Met Ser Thr Arg Trp
                245                 250                 255

Trp Ser Leu Leu
        260

<210> SEQ ID NO 5
<211> LENGTH: 1896
<212> TYPE: DNA
<213> ORGANISM: Homo sapiens
<220> FEATURE:
<223> OTHER INFORMATION: Description of Artificial Sequence: Assembled
      using  sequences from AC024267
<221> NAME/KEY: misc_feature
<222> LOCATION: (25)..(1291)
<223> OTHER INFORMATION: WHerein any n is a, g, c, or t.

<400> SEQUENCE: 5
ccagcgccat catcagatgg caagntcagc cccggcacgt tatccatagg aagcgcttta      60
accgtaccct ctttcccaac caactctact gccatggtgg acctcaccaa ctcacttcga     120
gcatttatgg atgtcaatgg agaaatcgag ataaatatgc tggacgagaa gctgatcaag     180
tttctggcct tgcagagaat acatcagctt ttcccctccc gggtccaacc ttcaccgggc     240
agtgtcggga cacatcagct ggcttctgga gggcaccaca tagaagnnnn nnnnnnnnnt     300
gtacaggccc gagctgtgtt ctacccctc ttagggttgg gaggagctgt gaacatgtcc      360
tatcgaaccc tctacatcgg gacaggagct gacatggatg tgtgccttac aaactatggt     420
cactgtaact acgtgtccgg gaaacatgcc tgcatattct acgatgagaa taccaaacat     480
tatgagctgt taaactacag tgagcatggg acaacggtgg acaatgtgct gtattcatgt     540
gacttctcgg agaagacccc gccaaccccc ccaagcagta ttgttgccaa agtgcagagt     600
gtcatcaggc gccgccggca ccagaaacag gacgaagagc caagtgagga ggcagccatg     660
atgagttccc aggcccaggg gccgcagcgg agaccctgca attgcaaagc cagcagctcg     720
agcttgattg ggggcagtgg ggccggctgg gagggcacag ccttactgca ccatggcagc     780
tacatcaagc tgggctgcct gcagtttgtc ttcagcatca ctgagtttgc gaccaaacag     840
cccaaaggcg atgccagcct gctgcaggat ggggtcttgg ccgagaagct ctctctcaag     900
ccccaccagg gccctgtgct gcgctccaac tctgttcctt aggactggcg gctacccgc      960 cactggcctg tacacccacc caagactcct gcaatgcaaa aatgtacaca aaccaagccc    1020
gggtgttttc tatactctac cagaaaccct tcaactacaa tctttgcatg aaatgaagaa    1080
aaccttttga ctgttttta aaatcctttt tctttttctc aagttctagg ggcatttgc     1140 acatatattt gtactcaaca tttcatggga aagcggcaga cctgagctga ggaacagcgt    1200
ggngcaggga gggaaagacc cagggtctgg acantttctc caacacaaaa nccttttccca   1260 cccancttcc tgcttccttc cccttcgngc ncccattgt aaaataatca ggaaacttgt     1320
tctattttgt ggcagtgaca atagttttat attaaaagaa aaaatacagt tttcataacc    1380
acaaatctat tcaatatcat tgtttttattt aatataaaga tcgctaccca ccttccttcc   1440
atggttccca ccctccacgt tattttccct ttctgcagcg gttgcactac aggtagctac    1500
tgtgtattat ggacaaatga gaaatgaatt cttttttctgg ctgtccatct attttatttc   1560
aaataaggaa aagtgtattt ggattttgtg taaatacatc tagtgatgac attttttcaa    1620
```

```
tgtttttaaa aaccgtgtac agtactacat gtggtagagc gttttctcaa attgtctatt    1680
gtagcaaaaa tgttttttgtc gtaaacctgt tttgtctcct ttttttgttc tcttgccact    1740
tctctcctct tcctcctgcc cctggttccc tcctctcctc ccaccccac aaccagtacc     1800 aatgtacata gtaattgtaa tgttttagac tttacagaaa ctttcctgta ttctgtatat    1860
aaaaaacaaa aatacttcaa aaaaaaaaaa aaaaaa                               1896
```

<210> SEQ ID NO 6
<211> LENGTH: 282
<212> TYPE: PRT
<213> ORGANISM: Homo sapiens
<220> FEATURE:
<223> OTHER INFORMATION: Description of Artificial Sequence: Encoded
      amino acid sequence of SEQ ID NO. 5
<221> NAME/KEY: VARIANT
<222> LOCATION: (65)..(69)
<223> OTHER INFORMATION: Wherein Xaa is any amino acid.

<400> SEQUENCE: 6

```
Met Val Asp Leu Thr Asn Ser Leu Arg Ala Phe Met Asp Val Asn Gly
  1               5                  10                  15

Glu Ile Glu Ile Asn Met Leu Asp Glu Lys Leu Ile Lys Phe Leu Ala
             20                  25                  30

Leu Gln Arg Ile His Gln Leu Phe Pro Ser Arg Val Gln Pro Ser Pro
         35                  40                  45

Gly Ser Val Gly Thr His Gln Leu Ala Ser Gly Gly His His Ile Glu
     50                  55                  60

Xaa Xaa Xaa Xaa Xaa Val Gln Ala Arg Ala Val Phe Tyr Pro Leu Leu
 65                  70                  75                  80

Gly Leu Gly Gly Ala Val Asn Met Ser Tyr Arg Thr Leu Tyr Ile Gly
                 85                  90                  95

Thr Gly Ala Asp Met Asp Val Cys Leu Thr Asn Tyr Gly His Cys Asn
            100                 105                 110

Tyr Val Ser Gly Lys His Ala Cys Ile Phe Tyr Asp Glu Asn Thr Lys
        115                 120                 125

His Tyr Glu Leu Leu Asn Tyr Ser Glu His Gly Thr Thr Val Asp Asn
    130                 135                 140

Val Leu Tyr Ser Cys Asp Phe Ser Glu Lys Thr Pro Pro Thr Pro Pro
145                 150                 155                 160

Ser Ser Ile Val Ala Lys Val Gln Ser Val Ile Arg Arg Arg Arg His
                165                 170                 175

Gln Lys Gln Asp Glu Glu Pro Ser Glu Glu Ala Ala Met Met Ser Ser
            180                 185                 190

Gln Ala Gln Gly Pro Gln Arg Arg Pro Cys Asn Cys Lys Ala Ser Ser
        195                 200                 205

Ser Ser Leu Ile Gly Gly Ser Gly Ala Gly Trp Glu Gly Thr Ala Leu
    210                 215                 220

Leu His His Gly Ser Tyr Ile Lys Leu Gly Cys Leu Gln Phe Val Phe
225                 230                 235                 240

Ser Ile Thr Glu Phe Ala Thr Lys Gln Pro Lys Gly Asp Ala Ser Leu
                245                 250                 255

Leu Gln Asp Gly Val Leu Ala Glu Lys Leu Ser Leu Lys Pro His Gln
            260                 265                 270

Gly Pro Val Leu Arg Ser Asn Ser Val Pro
        275                 280
```

<210> SEQ ID NO 7
<211> LENGTH: 1969
<212> TYPE: DNA
<213> ORGANISM: Murine MTC49

<400> SEQUENCE: 7

```
cccaaatgcc accctgggtg ctcactcccc cccaggctgc aggagacagt atcttggcca      60
caggtgccaa ccaacgattc tgctcaccag cgccatcatc agctctagga gttccagagc     120
ctgtgggttg agaatcaaga agggaacatc accttgggtc cgaaatccag aactgtctca     180
acaatggggg attggaccgg tgggtttccc tcaggcgacc caactctact gccatggtgg     240
acctcaccaa ctcacttcga gcatttatgg atgtcaacgg agaaatcgag ataaatatgt     300
tggatgagaa gctgatcaag tttctggcct tgcagagagt acatcagctt ttcccttccc     360
gggtccaagc ttcaccgggc aatgttggga cacatccgct ggcttctgga gggcaccacc     420
cagaagtgca agaaaggag gtacaggccc gagctgtgtt ctgcccctc ttagggttgg       480
gaggagctgt gaacatgtgc tatcgaaccc tctacatcgg acaggagct gacatggatg      540
tgtgccttac aaactatggt cactgtaact acgtgtccgg gaaacatgcc tgcatattct     600
acgatgagaa taccaaacat tatgagctgt taaactacag tgagcatggg acaacggtgg     660
acaatgtgct gtattcatgt gacttctctg agaagacccc gccaacccc caagcagta      720
ttgttgccaa agtacagagt gtcatcaggc gccgcgagca ccagaaacag gatgaagagc     780
caagtgagga ggcagccatg atgagttccc aggcccaggg gccacagcgg agaccctgca     840
attgcaaagc cagcagctca agcttgattg ggggcagtgg ggccggctgg gagggcacag     900
cattactcca ccatgcagc tacatcaagc tgggctgcct gcagtttgtc ttcagcatca     960
ctgagtttgc gaccaaacag cccaaaggcg atgccagcct gctgcaggat ggggtcttgg    1020
ctgagaaact ctctctcaag ccccatcagg gccctgtgct cgcgctccaac tccgttccct    1080
aggccattgg cctggacgcc cacccaagac tcctgcaatg caaaaatgta cacgaaccaa    1140
gcctgggtgt tttctatacc agaaaccctc aactacaatc tttgcatgaa atgaagaaaa    1200
cctttttgact gtttttttaag actttttttc ttttctcaag ttctagggg catttgcaca    1260
tatatttgta ctcaacatt catgggaaag cggcagatcc gcgctgagga gcagcgaggg    1320
cagggacagg aggccctggt ctggacactt cctccagcac aatcccttcc cccgcctcct    1380
gctcctcccc ctcgaccgcc tgcccactgt tgtaaataa tcagaaactt gttctatttt     1440
gtggcagtga caatagtttt atattaaaag aaaaaaatac agttttcata cagcaaaatc    1500
tatacaatat cattgtttta tttaatataa agatcgctac ccactccttt ccatggttcc    1560
caccctacaa ggacttcccc tctctgcagc agttgcacta caggtagcta ctgtgtatat    1620
ggacaaatga gaaatgaatc ctttttttctg gctgtccatc tatttattt caaataagga   1680
aaagtgtatt tggattttgt gtaaatacat ctagtgatgg catttttttca atgttttaa    1740
aagctgtgta cagtacatgt ggtagagtgt ttctcaaatt gtctattgta gcaaaggcgt    1800
ttttgtcgta aacctgttct gtgtcctttt tgttcttac cacttctctt cctcctcacc    1860
ccagatactt cctcttcccc acaaccaatg tacatagtaa ttgtaatgtt ttagacttga    1920
cagaaacttt cctgtattct gtatataaaa accaaaaata cttcaaatt               1969
```

<210> SEQ ID NO 8
<211> LENGTH: 282
<212> TYPE: PRT
<213> ORGANISM: Murinae gen. sp.

<400> SEQUENCE: 8

```
Met Val Asp Leu Thr Asn Ser Leu Arg Ala Phe Met Asp Val Asn Gly
  1               5                  10                  15
Glu Ile Glu Ile Asn Met Leu Asp Glu Lys Leu Ile Lys Phe Leu Ala
             20                  25                  30
Leu Gln Arg Val His Gln Leu Phe Pro Ser Arg Val Gln Ala Ser Pro
         35                  40                  45
Gly Asn Val Gly Thr His Pro Leu Ala Ser Gly Gly His His Pro Glu
     50                  55                  60
Val Gln Arg Lys Glu Val Gln Ala Arg Ala Val Phe Cys Pro Leu Leu
 65                  70                  75                  80
Gly Leu Gly Gly Ala Val Asn Met Cys Tyr Arg Thr Leu Tyr Ile Gly
                 85                  90                  95
Thr Gly Ala Asp Met Asp Val Cys Leu Thr Asn Tyr Gly His Cys Asn
            100                 105                 110
Tyr Val Ser Gly Lys His Ala Cys Ile Phe Tyr Asp Glu Asn Thr Lys
        115                 120                 125
His Tyr Glu Leu Leu Asn Tyr Ser Glu His Gly Thr Thr Val Asp Asn
    130                 135                 140
Val Leu Tyr Ser Cys Asp Phe Ser Glu Lys Thr Pro Pro Thr Pro Pro
145                 150                 155                 160
Ser Ser Ile Val Ala Lys Val Gln Ser Val Ile Arg Arg Arg Glu His
                165                 170                 175
Gln Lys Gln Asp Glu Glu Pro Ser Glu Glu Ala Ala Met Met Ser Ser
            180                 185                 190
Gln Ala Gln Gly Pro Gln Arg Arg Pro Cys Asn Cys Lys Ala Ser Ser
        195                 200                 205
Ser Ser Leu Ile Gly Gly Ser Gly Ala Gly Trp Glu Gly Thr Ala Leu
    210                 215                 220
Leu His His Gly Ser Tyr Ile Lys Leu Gly Cys Leu Gln Phe Val Phe
225                 230                 235                 240
Ser Ile Thr Glu Phe Ala Thr Lys Gln Pro Lys Gly Asp Ala Ser Leu
                245                 250                 255
Leu Gln Asp Gly Val Leu Ala Glu Lys Leu Ser Leu Lys Pro His Gln
            260                 265                 270
Gly Pro Val Leu Arg Ser Asn Ser Val Pro
        275                 280
```

<210> SEQ ID NO 9
<211> LENGTH: 555
<212> TYPE: DNA
<213> ORGANISM: Artificial Sequence
<220> FEATURE:
<223> OTHER INFORMATION: Description of Artificial Sequence: FHA domain

<400> SEQUENCE: 9

```
aatttataaa gaaaagacat ttattttggc tcacaattct gcaggctgta ctggcatggc      60
accaacattt gctcagcttc tggtgagggc ctcaggaagc ttacagtaaa ggcggaaggt     120
gaagggggag caggcatatc acatggcgag aaagagggga gaggtctcag actcttttaa     180
acaaccatat ctatgtgaat tgagtgagaa ctcactcatc accaaggaga tggtgctgag     240
ccattcatga aggatcctct ctcatgatcc aaatacttcc caccaggctc cacttccaac     300
actgggaatt acatttcaac atgagatttg gaggggacga gcatccaaac catatcagat     360
```

```
ggtgagacag gagaactttg tgtgtcccag ctgcactggt ctgaagatat aactaagtcc    420
ctggactttt tctcccttaa ttggagaatt cctaatgttc catgatcagc ctgattgacc    480
agtggctgac tggtcctgag aggggagata aaaacagaca cacagctttc tccatagaca    540
aatctcaaca ctttc                                                     555
```

<210> SEQ ID NO 10
<211> LENGTH: 1289
<212> TYPE: DNA
<213> ORGANISM: Artificial Sequence
<220> FEATURE:
<223> OTHER INFORMATION: Description of Artificial Sequence: corresponds
      to the reverse complement of the MTC50 nucleotide sequence.

<400> SEQUENCE: 10

```
ggggctagaa gtctggcacc caccgcctgg ccaggtgttc gggacgcgac caggtgggcg     60
gtcgccgccc cgggagcgcg gcttaatagc tgagagcccg ggggccaggc cgcggctgcg    120
gcccaggcaa cgccctgagg gtggccacgc tgccaggtgt tccactcccc cgggactatg    180
ggcaagggcc ggggcgggga gggcggcagg tgctgacact ggagctgccc ggagtcgggg    240
aactcggcct cctaagactg aggacactcg cctgctgggc cggtcgagct gtgcggtgcc    300
ctccggacgc aggggggcgct gcagccacgc tgggtcaggc tccgcaggcc ctcccaaccc    360
ggggactaac ggcgccggtg acgacttcgc cgcgcgttgg tcagccatgg ccaccgctct    420
cgcgctacgt agcttgtacc gagcgcgacc ctcgctgcgc tgtccgcccg ttgagcttcc    480
ctgggccccg cggcgagggc atcggctctc gccggcggat gacgagctgt atcagcggac    540
gcgcatctct ctgctgcaac gcgaggccgc tcaggcaatg tacatcgaca gctacaacag    600
ccgcggcttc atgataaacg gaaccgcgt gctcggcccc tgcgctctgc tcccgcactc    660
ggtggtgcag tggaacgtgg atcccacca ggacatcacc gaagacagct ttccctctt    720 ctggttgctg agccccgga tagagatcgt ggtggtgggg actggagacc ggaccgagag    780
gctgcagtcc caggtgcttc aagccatgag gcagcgggc attgctgtgg aagtgcagga    840
cacgcccaat gcctgtgcca ccttcaactt cctgtgtcat gaaggccgag taactggagc    900
tgctctcatc cctccaccag gagggacttc acttacatct ttgggccaag ctgctcaatg    960
aaccgccagg aactgacctg ctgactgcac tctgccaggc ttcccaatgc tttcactctt   1020 atctacccttt tggcacttat cttgcttatc aacataataa tttatacact tctcccattt   1080
tgtatcaggt gtgttgctgg ccaggagctg atggctcact gggctcttgg aggggaatgt   1140
gaagaaacca aggagtcact ttttcatcta gattacttag gattccttga cttttcagaa   1200
gtcgggaagc agtatgtttg cctgttgtag acctacttgc tcacatgcag atttgagagg   1260
acctcaacgg ctttctcac aaaaaaaaa                                      1289
```

<210> SEQ ID NO 11
<211> LENGTH: 184
<212> TYPE: PRT
<213> ORGANISM: Artificial Sequence
<220> FEATURE:
<223> OTHER INFORMATION: Description of Artificial Sequence: amino acid
      sequence which corresponds to SEQ ID NO. 10

<400> SEQUENCE: 11

```
Met Ala Thr Ala Leu Ala Leu Arg Ser Leu Tyr Arg Ala Arg Pro Ser
  1               5                  10                  15

Leu Arg Cys Pro Pro Val Glu Leu Pro Trp Ala Pro Arg Arg Gly His
             20                  25                  30
```

```
Arg Leu Ser Pro Ala Asp Asp Glu Leu Tyr Gln Arg Thr Arg Ile Ser
         35                  40                  45

Leu Leu Gln Arg Glu Ala Ala Gln Ala Met Tyr Ile Asp Ser Tyr Asn
 50                  55                  60

Ser Arg Gly Phe Met Ile Asn Gly Asn Arg Val Leu Gly Pro Cys Ala
 65                  70                  75                  80

Leu Leu Pro His Ser Val Val Gln Trp Asn Val Gly Ser His Gln Asp
                 85                  90                  95

Ile Thr Glu Asp Ser Phe Ser Leu Phe Trp Leu Leu Glu Pro Arg Ile
            100                 105                 110

Glu Ile Val Val Val Gly Thr Gly Asp Arg Thr Glu Arg Leu Gln Ser
        115                 120                 125

Gln Val Leu Gln Ala Met Arg Gln Arg Gly Ile Ala Val Glu Val Gln
130                 135                 140

Asp Thr Pro Asn Ala Cys Ala Thr Phe Asn Phe Leu Cys His Glu Gly
145                 150                 155                 160

Arg Val Thr Gly Ala Ala Leu Ile Pro Pro Pro Gly Gly Thr Ser Leu
                165                 170                 175

Thr Ser Leu Gly Gln Ala Ala Gln
            180
```

<210> SEQ ID NO 12
<211> LENGTH: 104
<212> TYPE: DNA
<213> ORGANISM: Mus sp.
<220> FEATURE:
<221> NAME/KEY: misc_feature
<222> LOCATION: (31)..(88)
<223> OTHER INFORMATION: Wherein any n is a, g, c, or t.

<400> SEQUENCE: 12
tgtacagcag ccgcttgaag tcctttaaga ngaaatctct tttcttgncg ngttgancct    60
tccacggngt anttgacgtc ccctggcntg gtttttgatc cgga                   104

<210> SEQ ID NO 13
<211> LENGTH: 34
<212> TYPE: PRT
<213> ORGANISM: Mus sp.
<220> FEATURE:
<221> NAME/KEY: VARIANT
<222> LOCATION: (6)..(25)
<223> OTHER INFORMATION: Wherein Xaa is any amino acid.

<400> SEQUENCE: 13

```
Ser Gly Ser Lys Thr Xaa Pro Gly Asp Val Xaa Tyr Xaa Val Glu Gly
 1               5                  10                  15

Ser Thr Arg Gln Glu Lys Arg Phe Xaa Leu Lys Gly Leu Gln Ala Ala
             20                  25                  30

Ala Val
```

<210> SEQ ID NO 14
<211> LENGTH: 34
<212> TYPE: PRT
<213> ORGANISM: Mus sp.
<220> FEATURE:
<221> NAME/KEY: VARIANT
<222> LOCATION: (6)..(25)
<223> OTHER INFORMATION: Wherein Xaa is any amino acid.

<400> SEQUENCE: 14

```
Pro Asp Gln Lys Pro Xaa Gln Gly Thr Ser Xaa Thr Pro Trp Lys Xaa
 1               5                  10                  15

Gln Xaa Xaa Lys Lys Arg Asp Phe Xaa Leu Lys Asp Phe Lys Arg Leu
             20                  25                  30

Leu Tyr
```

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 15
cataagccct tgtaaagtaa crcagtgttc tgtgctatat acttgct                47

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 16
cagtgttctg tgctatatac ytgctggctg ggtagt                            36

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 17
gtgtcattag catggtgrat catatacttc tctgcacaca aacac                  45

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 18
agcatggtgg atmatatact tctctgcaca caaaca                            36

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 19
ttcatgctat aaataaaktt ccctattagt tccc                              34

<210> SEQ ID NO 20
<211> LENGTH: 37
<212> TYPE: DNA
<213> ORGANISM: Artificial Sequence
<220> FEATURE:

```
<223> OTHER INFORMATION: Description of Artificial Sequence: chemically
      synthesized probe

<400> SEQUENCE: 20
ggttttaagc cagaartctg gagagatgtc atgccag                                37

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 21
ctccagctgc aggttttscc tctccagctg taatttgt                               38

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 22
gctctcggca aaggcrctcg cctcggccc                                         29

<210> SEQ ID NO 23
<211> LENGTH: 46
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 23
acgatctccc gcaccttctc ctgyaccacc actttggcgt tctcct                      46

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 24
tgctcgtatt tccggttggt gtcctccacc y                                      31

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 25
gggtcctcag cagggtgtg gtg                                                23

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: chemically
``` synthesized probe

<400> SEQUENCE: 26
ggcttgctga aatttayagg cagactgacg tttt                                34

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 27
actgacgttt tcyttcacat gtactcc                                        27

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 28
attttataaa cgatgragcc catcagcccc att                                 33

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 29
ttcatgggga tccataygtt tttaataata cttt                                34

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 30
ttttaactta taagccycaa cttcaccgca gaataaagaa tgtag                    45

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 31
agaaggcagc atgtgtayac aaccatacc                                      29

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 32
gcgctttgtt ttctctctac aarccattcc ccgc         34

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 33
tgcctccaga gaggtggrtg cctgggttga gagacacagc t         41

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 34
gaggtcattc atcaacaaat atrtttattg gagaccgact tt         42

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 35
gtgtgtgact gtgaaggggc cgcyggcgtc tgtaggaa         38

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 36
caatgtgatc ctataamacc ctgtgcggcc gggaaag         37

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 37 taattcctttt tcttttcttc yttatttcct ctgcccctt         39

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 38
aaaattaaag caagaagtcc ayagtaattt atttgc                                    36

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 39
caagtgccat gctacasccc ctgcttgaca accaggtt                                  38

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 40
tccagacttc tggcttaamc agggcaagca gggacaggac ttt                            43

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 41
aaatccacac ttakggactt ctttcttctc c                                         31

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 42 gaaaaggaa atcaacctcy aggtgtacca aaaggggc                                   38

<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 43
ggaggaggat gaagaaggaa aaargaaaa acaaaacccc aaatgcc                         47

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 44
ctcgcaatgc agggmgaact cggcttggaa                                      30

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 45
cttgagcagc agcccgagca mcgactcgcc gcccgtattc tcgt                       44

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 46
cgccgcccgt attctcgtty cagtcgctgc tgctctcgtc gt                         42

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 47
ctctaagaag ccaggaaggg tccctggtgc actccactct                            40

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 48
ggttgctggt gggaagrtgg ccatcgtgcc tggc                                  34

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 49
aaaggtggtc ccggatcagc rgtgagcccc tatcctacc                             39

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 50
ttctaactaa gcgaaacaat gcayagcgtc aacagatcaa agcagcatat        50

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 51
ttgaggaggt tgttttrgct ctgctaaaaa ctccagcg        38

<210> SEQ ID NO 52
<211> LENGTH: 41
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 52
aaatcatttt tatattataw ctctgtataa tagagataag t        41

<210> SEQ ID NO 53
<211> LENGTH: 37
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 53
agacatctat cagggtcrtg atttgctgtt gctgctt        37

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 54
tgaaaatatc aaagkatctc tttaggg        28

<210> SEQ ID NO 55
<211> LENGTH: 37
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 55
ctgcgatgag cttgggraag ccaggatcca ttttctt        37

<210> SEQ ID NO 56
<211> LENGTH: 38
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 56
agtgacaggg cccagygtgg gggtggggcc ggtgccaa        38

<210> SEQ ID NO 57
<211> LENGTH: 36
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 57
gccccacttg cggtcrtcat cgtagttggc tgtggt                          36

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 58
ggagctgtcc cccsgacgag cccccag                                    27

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 59
cattttgagg gyggaaaata actg                                       24

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 60
tggcgcccag cttyccgtcg cccgcgaa                                   28

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 61
ccttgttggg gcatgggytt cgcagcttat c                               31

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: chemically
      synthesized probe

<400> SEQUENCE: 62
gccttttcct cccrgctctg gtgggagg                                   28

```
<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence:  chemically
      synthesized probe

<400> SEQUENCE: 63
atgacctcaa aggygatgag cagct                                            25
```